United States Patent
Xie et al.

(10) Patent No.: US 7,399,619 B2
(45) Date of Patent: Jul. 15, 2008

(54) SITE SPECIFIC INCORPORATION OF HEAVY ATOM-CONTAINING UNNATURAL AMINO ACIDS INTO PROTEINS FOR STRUCTURE DETERMINATION

(75) Inventors: Jianming Xie, San Diego, CA (US); Lei Wang, San Diego, CA (US); Ning Wu, Boston, MA (US); Peter G. Schultz, La Jolla, CA (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 11/137,850

(22) Filed: May 24, 2005

(65) Prior Publication Data

US 2005/0272121 A1 Dec. 8, 2005

Related U.S. Application Data

(60) Provisional application No. 60/574,554, filed on May 25, 2004, provisional application No. 60/602,048, filed on Aug. 16, 2004.

(51) Int. Cl.
*C12P 21/06* (2006.01)
*C07H 21/04* (2006.01)
*C12N 9/00* (2006.01)
*C12N 1/21* (2006.01)
*G06F 19/00* (2006.01)
*G01N 33/48* (2006.01)
*G01N 33/50* (2006.01)

(52) U.S. Cl. .................. 435/183; 435/193; 435/69.1; 435/252.33; 435/488; 530/350; 536/23.1; 536/23; 536/24.1

(58) Field of Classification Search .................. 435/183, 435/193, 69.1, 252.33, 488; 536/23.1, 23, 536/24.1; 530/350
See application file for complete search history.

(56) References Cited

U.S. PATENT DOCUMENTS

| | | | |
|---|---|---|---|
| 6,927,042 | B2 | 8/2005 | Schultz et al. |
| 7,045,337 | B2 | 5/2006 | Schultz et al. |
| 7,083,970 | B2 | 8/2006 | Schultz et al. |
| 7,129,333 | B2 | 10/2006 | Schultz et al. |
| 7,183,082 | B2 | 2/2007 | Schultz et al. |
| 7,199,222 | B2 | 4/2007 | Shultz et al. |
| 7,217,809 | B2 | 5/2007 | Schultz et al. |
| 7,238,510 | B2 | 7/2007 | Schultz et al. |
| 7,262,040 | B2 | 8/2007 | Schultz et al. |
| 2003/0082575 | A1 | 5/2003 | Schultz et al. |
| 2004/0198637 | A1 | 10/2004 | Schultz et al. |
| 2004/0265952 | A1 | 12/2004 | Deiters et al. |
| 2005/0009049 | A1 | 1/2005 | Chin et al. |
| 2005/0136513 | A1 | 6/2005 | Zhang et al. |
| 2005/0208536 | A1 | 9/2005 | Schultz et al. |
| 2005/0227318 | A1 | 10/2005 | Alfonta et al. |
| 2006/0063244 | A1 | 3/2006 | Schultz et al. |
| 2006/0068478 | A1 | 3/2006 | Schultz et al. |
| 2006/0160175 | A1 | 7/2006 | Anderson et al. |
| 2006/0177900 | A1 | 8/2006 | Anderson et al. |
| 2006/0234367 | A1 | 10/2006 | Schultz et al. |
| 2006/0246509 | A1 | 11/2006 | Deiters et al. |
| 2007/0009990 | A1 | 1/2007 | Alfonta et al. |
| 2007/0020634 | A1 | 1/2007 | Anderson et al. |
| 2007/0042461 | A1 | 2/2007 | Anderson et al. |
| 2007/0111193 | A1 | 5/2007 | Zhang et al. |
| 2007/0154952 | A1 | 7/2007 | Chin et al. |
| 2007/0166791 | A1 | 7/2007 | Chin et al. |
| 2007/0172915 | A1 | 7/2007 | Schultz et al. |
| 2007/0184517 | A1 | 8/2007 | Schultz et al. |

FOREIGN PATENT DOCUMENTS

| | | |
|---|---|---|
| WO | WO 02/085923 | 10/2002 |
| WO | WO 02/086075 | 10/2002 |
| WO | WO 2004/035743 | 4/2004 |
| WO | WO 2004/094593 | 4/2004 |
| WO | WO 2005/019415 | 3/2005 |

OTHER PUBLICATIONS

Branden et al. ("Introduction to Protein Structure Second Edition", Garland Publishing Inc., New York, 1999.*
Drenth ("Principles of X-ray Crystallography," Springer, New York, 1995) p. 1-.*
Anderson et al. (2002) "Exploring the limits of codon and anticodon size" Chemistry and Biology 9:237-244.
Boles et al. (1994) "Bio-incorporation of telluromethionine into buried residues of dihydrofolate reductase" Nat. Struct. Biol. 1:283-284.
Budisa et al. (1997) "Bioincorporation of telluromethionine into proteins: a promising new approach for X-ray structure analysis of proteins" J. Mol. Biol. 270:616-623.
Chin et al. (2003) "An expanded eukaryotic genetic code" Science 301:964-967.

(Continued)

*Primary Examiner*—Kagnew H. Gebreyesus
(74) *Attorney, Agent, or Firm*—Quine Intellectual Property Law Group, P.C.; Monica Elrod-Erickson

(57) ABSTRACT

Translation systems and other compositions including orthogonal aminoacyl tRNA-synthetases that preferentially charge an orthogonal tRNA with an iodinated or brominated amino acid are provided. Nucleic acids encoding such synthetases are also described, as are methods and kits for producing proteins including heavy atom-containing amino acids, e.g., brominated or iodinated amino acids. Methods of determining the structure of a protein, e.g., a protein into which a heavy atom has been site-specifically incorporated through use of an orthogonal tRNA/aminoacyl tRNA-synthetase pair, are also described.

35 Claims, 10 Drawing Sheets
(5 of 10 Drawing Sheet(s) Filed in Color)

OTHER PUBLICATIONS

Chin et al., (2002) "Addition of a photocrosslinking amino acid to the genetic code of *Escherichia coli*" Proc. Natl. Acad. Sci. U. S. A., 99:11020-11024.

Chin and Schultz, (2002) "In vivo photocrosslinking with unnatural amino acid mutagenesis" ChemBioChem, 3:1135-1137.

Feng et al., (2003) "Expanding tRNA recognition of a tRNA synthetase by a single amino acid change" PNAS 100(10):5676-5681.

Forster et al., (2003) "Programming peptidomimetic synthetases by translating genetic codes designed de novo" PNAS 100(11):6353-6357.

Furter (1998) "Expansion of the genetic code: site-directed *p*-fluoro-phenylalanine incorporation in *Escherichia coli*" Protein Sci., 7:419-426.

Hirao, et al. (2002) "An unnatural base pair for incorporating amino acid analogues into protein" Nature Biotechnology, 20:177-182.

Hohsaka et al. (1999) "Efficient incoporation of nonnatural amino acids with large aromatic groups into streptavidin in in vitro protein synthesizing systems" *J. Am. Chem. Soc.* 121:34-40.

Hohsaka et al. (1999) "Incorporation of two different nonnatural amino acids independently into a single protein through extension of the genetic code" J. Am. Chem. Soc. 121:12194.

Ibba, P. Kast and H. Hennecke, (1994) "Substrate specificity is determined by amino acid binding pocket size in *Escherichia coli* phenylalanyl-tRNA synthetase" Biochemistry, 33:7107.

Ibba and H. Hennecke, (1995) "Relaxing the substrate specificity of an aminoacyl-tRNA synthetase allows in vitro and in vitro synthesis of proteins containing unnatural amino acid" *FEBS Lett.*, 364:272.

Kirshenbaum et al. (2002) "Biosynthesis of proteins incorporating a versatile set of phenylalanine analogues" ChemBioChem 3:235-237.

Kowal and Oliver, (1997) "Exploiting unassigned codons in *Micrococcus luteus* for tNRA-based amino acid mutagenesis" Nucl. Acid. Res., 25:4685-4689.

Liu, D.R. and Schultz, P.G. (1999) "Progress toward the evolution of an organism with an expanded genetic code" PNAS United States 96:4780-4785.

Ma et al., (1993) "In vitro protein engineering using synthetic tRNA$^{Ala}$ with different anticodons" Biochemistry 32:7939-7945.

Magliery (2001) "Expanding the genetic code: selection of efficient suppressors of four-base codons and identification of 'shifty' four-base codons with a library approach in *Escherichia coli*" J. Mol. Biol. 307:755-769.

Moore et al. (2000) "Quadruplet codons: implications for code expansion and the specification of translation step size" J. Mol. Biol. 298-195.

Sakamoto et al. (2002) "Site-specific incorporation of an unnatural amino acid into proteins in mammalian cells" Nucleic Acids Res 30:4692-4699.

Sharma, R. et al., "Efficient introduction of aryl bromide functionality into proteins in vivo" *FEBS Lett.*, 467:37 (2000).

Wang et al., (2000) "A new functional suppressor tRNA/aminoacyl-tRNA synthetase pair for the in vivo incorporation of unnatural amino acids into proteins" J. Am. Chem. Soc., 122:5010-5011.

Wang et al., (2001) "Expanding the genetic code of *Escherichia coli*" Science, 292:498-500.

Wang (2003) "Unnatural amino acid mutagenesis of green fluorescent protein" J. Org. Chem. 68:174-176.

Wang et al., (2003) "Addition of the keto functional group to the genetic code of *Escherichia coli*" Proc. Natl. Acad. Sci. U. S. A., 100:56-61.

Wang (2003) "Expanding the genetic code" Science 302:584-585.

Wu, Y., et al. (2002) "Enzynmatic phosphorylation of unnatural nucleosides" J. Am. Chem. Soc. 124:14626-14630.

Xie et al. (2004) "The site-specific incorporation of p-iodo-L-phenylalanine into proteins for structure determination" Nature Biotechnology 22:1297-1301.

\* cited by examiner

IodoPheRS #1:

DNA sequence:
atggacgaatttgaaatgataaagagaaacacatctgaaattatcagcgaggaagagttaa
gagaggttttaaaaaaagatgaaaaatctgctCTGataggttttgaaccaagtggtaaaat
acatttagggcattatctccaaataaaaaagatgattgatttacaaaatgctggatttgat
ataattatattgttggctgatttacacgcctatttaaaccagaaaggagagttggatgaga
ttagaaaaataggagattataacaaaaaagttttttgaagcaatggggttaaaggcaaaata
tgtttatggaagtTCGttccagcttgataaggattatacactgaatgtctatagattggct
ttaaaaactaccttaaaaagagcaagaaggagtatggaacttatagcaagagaggatgaaa
atccaaaggttgctgaagttatctatccaataatgcaggttaatCCTCTTcattatGAGgg
cgttgatgttgcagttggagggatggagcagagaaaaatacacatgttagcaagggagctt
ttaccaaaaaaggttgtttgtattcacaaccctgtcttaacgggtttggatggagaaggaa
agatgagttcttcaaaagggaattttatagctgttgatgactctccagaagagattagggc
taagataaagaaagcatactgcccagctggagttgttgaaggaaatccaataatggagata
gctaaatacttccttgaatatcctttaaccataaaaaggccagaaaaatttggtggagatt
tgacagttaatagctatgaggagttagagagtttatttaaaaataaggaattgcatccaat
ggatttaaaaaatgctgtagctgaagaacttataaagatttttagagccaattagaaagaga
ttataa

Protein sequence:
MDEFEMIKRNTSEIISEEELREVLKKDEKSALIGFEPSGKIHLGHYLQIKKMIDLQNAGFD
IIILLADLHAYLNQKGELDEIRKIGDYNKKVFEAMGLKAKYVYGSSFQLDKDYTLNVYRLA
LKTTLKRARRSMELIAREDENPKVAEVIYPIMQVNPLHYEGVDVAVGGMEQRKIHMLAREL
LPKKVVCIHNPVLTGLDGEGKMSSSKGNFIAVDDSPEEIRAKIKKAYCPAGVVEGNPIMEI
AKYFLEYPLTIKRPEKFGGDLTVNSYEELESLFKNKELHPMDLKNAVAEELIKILEPIRKR
L

Fig. 4A

IodoPheRS #2:

DNA sequence:
```
atggacgaatttgaaatgataaagagaaacacatctgaaattatcagcgaggaagagttaa
gagaggttttaaaaaaagatgaaaaGtctgctCTGataggttttgaaccaagtggtaaaat
acatttagggcattatctccaaataaaaaagatgattgatttacaaaatgctggatttgat
ataattatattgttggctgatttacacgcctatttaaaccagaaaggagagttggatgaga
ttagaaaaataggagattataacaaaaagttttgaagcaatggggttaaaggcaaaata
tgtttatggaagtgaattccagcttgataaggattatacactgaatgtctatagattggct
ttaaaaactaccttaaaaagagcaagaaggagtatggaacttatagcaagagaggatgaaa
atccaaaggttgctgaagttatctatccaataatgcaggttaatCCTCGTcattatCGTgg
cgttgatgttgcagttggagggatggagcagagaaaaatacacatgttagcaagggagctt
ttaccaaaaaaggttgtttgtattcacaaccctgtcttaacgggtttggatggagaaggaa
agatgagttcttcaaaagggaatttttatagctgttgatgactctccagaagagattagggc
taagataaagaaagcatactgcccagctggagttgttgaaggaaatccaataatggagata
gctaaatacttccttgaatatcctttaaccataaaaaggccagaaaaatttggtggagatt
tgacagttaatagctatgaggagttagagagtttatttaaaaataaggaattgcatccaat
ggatttaaaaaatgctgtagctgaagaacttataaagatttagagccaattagaaagaga
ttataa
```

Protein sequence:
```
MDEFEMIKRNTSEIISEEELREVLKKDEKSALIGFEPSGKIHLGHYLQIKKMIDLQNAGFD
IIILLADLHAYLNQKGELDEIRKIGDYNKKVFEAMGLKAKYVYGSEFQLDKDYTLNVYRLA
LKTTLKRARRSMELIAREDENPKVAEVIYPIMQVNPRHYRGVDVAVGGMEQRKIHMLAREL
LPKKVVCIHNPVLTGLDGEGKMSSSKGNFIAVDDSPEEIRAKIKKAYCPAGVVEGNPIMEI
AKYFLEYPLTIKRPEKFGGDLTVNSYEELESLFKNKELHPMDLKNAVAEELIKILEPIRKR
L
```

Fig. 4B

Mutant tRNA:

CCGGCGGUAGUUCAGCagGGcAGAACGGCGGACUcUAaAUCCGCAUGgCGCU
GGUUCAAAUCCGGCCCGCCGGA

Fig. 5

SEQUENCE LISTING

<160> NUMBER OF SEQ ID NOS: 9

<210> SEQ ID NO 1
<211> LENGTH: 921
<212> TYPE: DNA
<213> ORGANISM: Artificial
<220> FEATURE:
<223> OTHER INFORMATION: mutant synthetase

<400> SEQUENCE: 1

```
atggacgaat tgaaatgat aaagagaaac acatctgaaa ttatcagcga ggaagagtta      60
agagaggttt taaaaaaaga tgaaaaatct gctctgatag gttttgaacc aagtggtaaa     120
atacatttag gcattatct ccaaataaaa aagatgattg atttacaaaa tgctggattt      180
gatataatta tattgttggc tgatttacac gcctatttaa accagaaagg agagttggat     240
gagattagaa aaataggaga ttataacaaa aaagtttttg aagcaatggg gttaaaggca     300
aaatatgttt atggaagttc gttccagctt gataaggatt atacactgaa tgtctataga     360
ttggctttaa aaactacctt aaaaagagca agaaggagta tggaacttat agcaagagag     420
gatgaaaatc caaggttgc tgaagttatc tatccaataa tgcaggttaa tcctcttcat      480
tatgagggcg ttgatgttgc agttggaggg atggagcaga gaaaaataca catgttagca     540
agggagcttt taccaaaaaa ggttgtttgt attcacaacc ctgtcttaac gggtttggat     600
ggagaaggaa agatgagttc ttcaaaaggg aattttatag ctgttgatga ctctccagaa     660
gagattaggg ctaagataaa gaaagcatac tgcccagctg gagttgttga aggaaatcca     720
ataatggaga tagctaaata cttccttgaa tatcctttaa ccataaaaag gccagaaaaa     780
tttggtggag atttgacagt taatagctat gaggagttag agagtttatt taaaaataag     840
gaattgcatc caatggattt aaaaaatgct gtagctgaag aacttataaa gattttagag     900
ccaattagaa agagattata a                                               921
```

<210> SEQ ID NO 2
<211> LENGTH: 921
<212> TYPE: DNA
<213> ORGANISM: Artificial

<220> FEATURE:
<223> OTHER INFORMATION: mutant synthetase

<400> SEQUENCE: 2

```
atggacgaat tgaaatgat aagagaaac acatctgaaa ttatcagcga ggaagagtta      60
agagaggttt taaaaaaga tgaaaagtct gctctgatag gttttgaacc aagtggtaaa     120
atacatttag gcattatct ccaaataaaa aagatgattg atttacaaaa tgctggattt     180
gatataatta tattgttggc tgatttacac gcctatttaa accagaaagg agagttggat     240
gagattagaa aataggaga ttataacaaa aagttttg aagcaatggg gttaaaggca       300
aaatatgttt atggaagtga attccagctt gataaggatt atacactgaa tgtctataga    360
ttggctttaa aaactacctt aaaaagagca agaaggagta tggaacttat agcaagagag    420
gatgaaaatc caaggttgc tgaagttatc tatccaataa tgcaggttaa tcctcgtcat    480
tatcgtggcg ttgatgttgc agttggaggg atggagcaga aaaaatata catgttagca     540
agggagcttt taccaaaaaa ggttgtttgt attcacaacc ctgtcttaac gggtttggat    600
ggagaaggaa agatgagttc ttcaaaaggg aattttatag ctgttgatga ctctccagaa    660
gagattaggg ctaagataaa gaaagcatac tgcccagctg gagttgttga aggaaatcca    720
ataatggaga tagctaaata cttccttgaa tatccttaa ccataaaaag gccagaaaaa    780
tttggtggag atttgacagt taatagctat gaggagttag agagtttatt taaaaataag    840
gaattgcatc caatggattt aaaaatgct gtagctgaag aacttataaa gattttagag     900
ccaattagaa agagattata a                                              921
```

<210> SEQ ID NO 3
<211> LENGTH: 306
<212> TYPE: PRT
<213> ORGANISM: Artificial
<220> FEATURE:
<223> OTHER INFORMATION: mutant synthetase

<400> SEQUENCE: 3

```
Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Leu
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Ser Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Pro Leu His
145                 150                 155                 160

Tyr Glu Gly Val Asp Val Ala Val Gly Gly Met Glu Gln Arg Lys Ile
                165                 170                 175
```

```
His Met Leu Ala Arg Glu Leu Leu Pro Lys Lys Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305

<210> SEQ ID NO 4
<211> LENGTH: 306
<212> TYPE: PRT
<213> ORGANISM: Artificial
<220> FEATURE:
<223> OTHER INFORMATION: mutant synthetase

<400> SEQUENCE: 4

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Leu
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Pro Arg His
145                 150                 155                 160

Tyr Arg Gly Val Asp Val Ala Val Gly Gly Met Glu Gln Arg Lys Ile
                165                 170                 175

His Met Leu Ala Arg Glu Leu Leu Pro Lys Lys Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220
```

```
Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
290                 295                 300

Arg Leu
305

<210> SEQ ID NO 5
<211> LENGTH: 74
<212> TYPE: RNA
<213> ORGANISM: Artificial
<220> FEATURE:
<223> OTHER INFORMATION: mutant tRNA

<400> SEQUENCE: 5
ccggcgguag uucagcaggg cagaacggcg gacucuaaau ccgcauggcg cugguucaaa    60
uccggcccgc cgga                                                     74

<210> SEQ ID NO 6
<211> LENGTH: 306
<212> TYPE: PRT
<213> ORGANISM: Artificial
<220> FEATURE:
<223> OTHER INFORMATION: mutant synthetase

<400> SEQUENCE: 6

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala His
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Lys Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Pro Cys His
145                 150                 155                 160

Tyr His Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190
```

```
Asn Pro Val Leu Thr Gly Leu Asp Gly Glu Gly Lys Met Ser Ser Ser
            195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
            245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305
```

```
<210> SEQ ID NO 7
<211> LENGTH: 424
<212> TYPE: PRT
<213> ORGANISM: Artificial
<220> FEATURE:
<223> OTHER INFORMATION: mutant synthetase

<400> SEQUENCE: 7

Met Ala Ser Ser Asn Leu Ile Lys Gln Leu Gln Glu Arg Gly Leu Val
1               5                   10                  15

Ala Gln Val Thr Asp Glu Glu Ala Leu Ala Glu Arg Leu Ala Gln Gly
            20                  25                  30

Pro Ile Ala Leu Val Cys Gly Phe Asp Pro Thr Ala Asp Ser Leu His
        35                  40                  45

Leu Gly His Leu Val Pro Leu Leu Cys Leu Lys Arg Phe Gln Gln Ala
    50                  55                  60

Gly His Lys Pro Val Ala Leu Val Gly Gly Ala Thr Gly Leu Ile Gly
65                  70                  75                  80

Asp Pro Ser Phe Lys Ala Ala Glu Arg Lys Leu Asn Thr Glu Glu Thr
                85                  90                  95

Val Gln Glu Trp Val Asp Lys Ile Arg Lys Gln Val Ala Pro Phe Leu
            100                 105                 110

Asp Phe Asp Cys Gly Glu Asn Ser Ala Ile Ala Ala Asn Asn Tyr Asp
        115                 120                 125

Trp Phe Gly Asn Met Asn Val Leu Thr Phe Leu Arg Asp Ile Gly Lys
    130                 135                 140

His Phe Ser Val Asn Gln Met Ile Asn Lys Glu Ala Val Lys Gln Arg
145                 150                 155                 160

Leu Asn Arg Glu Asp Gln Gly Ile Ser Phe Thr Glu Phe Ser Tyr Asn
                165                 170                 175

Leu Leu Gln Gly Tyr Ser Tyr Ala Cys Leu Asn Lys Gln Tyr Gly Val
            180                 185                 190

Val Leu Gln Ile Gly Gly Ser Asp Gln Trp Gly Asn Ile Thr Ser Gly
        195                 200                 205

Ile Asp Leu Thr Arg Arg Leu His Gln Asn Gln Val Phe Gly Leu Thr
    210                 215                 220

Val Pro Leu Ile Thr Lys Ala Asp Gly Thr Lys Phe Gly Lys Thr Glu
225                 230                 235                 240
```

Gly Gly Ala Val Trp Leu Asp Pro Lys Lys Thr Ser Pro Tyr Lys Phe
            245                 250                 255

Tyr Gln Phe Trp Ile Asn Thr Ala Asp Ala Asp Val Tyr Arg Phe Leu
        260                 265                 270

Lys Phe Phe Thr Phe Met Ser Ile Glu Glu Ile Asn Ala Leu Glu Glu
    275                 280                 285

Glu Asp Lys Asn Ser Gly Lys Ala Pro Arg Ala Gln Tyr Val Leu Ala
290                 295                 300

Glu Gln Val Thr Arg Leu Val His Gly Glu Glu Gly Leu Gln Ala Ala
305                 310                 315                 320

Lys Arg Ile Thr Glu Cys Leu Phe Ser Gly Ser Leu Ser Ala Leu Ser
                325                 330                 335

Glu Ala Asp Phe Glu Gln Leu Ala Gln Asp Gly Val Pro Met Val Glu
            340                 345                 350

Met Glu Lys Gly Ala Asp Leu Met Gln Ala Leu Val Asp Ser Glu Leu
        355                 360                 365

Gln Pro Ser Arg Gly Gln Ala Arg Lys Thr Ile Ala Ser Asn Ala Ile
    370                 375                 380

Thr Ile Asn Gly Glu Lys Gln Ser Asp Pro Glu Tyr Phe Phe Lys Glu
385                 390                 395                 400

Glu Asp Arg Leu Phe Gly Arg Phe Thr Leu Leu Arg Arg Gly Lys Lys
                405                 410                 415

Asn Tyr Cys Leu Ile Cys Trp Lys
            420

<210> SEQ ID NO 8
<211> LENGTH: 424
<212> TYPE: PRT
<213> ORGANISM: Artificial
<220> FEATURE:
<223> OTHER INFORMATION: mutant synthetase

<400> SEQUENCE: 8

Met Ala Ser Ser Asn Leu Ile Lys Gln Leu Gln Glu Arg Gly Leu Val
1               5                   10                  15

Ala Gln Val Thr Asp Glu Glu Ala Leu Ala Glu Arg Leu Ala Gln Gly
            20                  25                  30

Pro Ile Ala Leu Ile Cys Gly Phe Asp Pro Thr Ala Asp Ser Leu His
        35                  40                  45

Leu Gly His Leu Val Pro Leu Leu Cys Leu Lys Arg Phe Gln Gln Ala
    50                  55                  60

Gly His Lys Pro Val Ala Leu Val Gly Gly Ala Thr Gly Leu Ile Gly
65                  70                  75                  80

Asp Pro Ser Phe Lys Ala Ala Glu Arg Lys Leu Asn Thr Glu Glu Thr
                85                  90                  95

Val Gln Glu Trp Val Asp Lys Ile Arg Lys Gln Val Ala Pro Phe Leu
            100                 105                 110

Asp Phe Asp Cys Gly Glu Asn Ser Ala Ile Ala Ala Asn Asn Tyr Asp
        115                 120                 125

Trp Phe Gly Asn Met Asn Val Leu Thr Phe Leu Arg Asp Ile Gly Lys
    130                 135                 140

His Phe Ser Val Asn Gln Met Ile Asn Lys Glu Ala Val Lys Gln Arg
145                 150                 155                 160

Leu Asn Arg Glu Asp Gln Gly Ile Ser Phe Thr Glu Phe Ser Tyr Asn
                165                 170                 175

Leu Leu Gln Gly Tyr Ser Met Ala Cys Leu Asn Lys Gln Tyr Gly Val
            180                 185                 190

Val Leu Gln Ile Gly Gly Ser Asp Gln Trp Gly Asn Ile Thr Ser Gly
        195                 200                 205

Ile Asp Leu Thr Arg Arg Leu His Gln Asn Gln Val Phe Gly Leu Thr
    210                 215                 220

Val Pro Leu Ile Thr Lys Ala Asp Gly Thr Lys Phe Gly Lys Thr Glu
225                 230                 235                 240

Gly Gly Ala Val Trp Leu Asp Pro Lys Lys Thr Ser Pro Tyr Lys Phe
                245                 250                 255

Tyr Gln Phe Trp Ile Asn Thr Ala Asp Ala Asp Val Tyr Arg Phe Leu
            260                 265                 270

Lys Phe Phe Thr Phe Met Ser Ile Glu Glu Ile Asn Ala Leu Glu Glu
        275                 280                 285

Glu Asp Lys Asn Ser Gly Lys Ala Pro Arg Ala Gln Tyr Val Leu Ala
    290                 295                 300

Glu Gln Val Thr Arg Leu Val His Gly Glu Gly Leu Gln Ala Ala
305                 310                 315                 320

Lys Arg Ile Thr Glu Cys Leu Phe Ser Gly Ser Leu Ser Ala Leu Ser
                325                 330                 335

Glu Ala Asp Phe Glu Gln Leu Ala Gln Asp Gly Val Pro Met Val Glu
            340                 345                 350

Met Glu Lys Gly Ala Asp Leu Met Gln Ala Leu Val Asp Ser Glu Leu
        355                 360                 365

Gln Pro Ser Arg Gly Gln Ala Arg Lys Thr Ile Ala Ser Asn Ala Ile
    370                 375                 380

Thr Ile Asn Gly Glu Lys Gln Ser Asp Pro Glu Tyr Phe Phe Lys Glu
385                 390                 395                 400

Glu Asp Arg Leu Phe Gly Arg Phe Thr Leu Leu Arg Arg Gly Lys Lys
                405                 410                 415

Asn Tyr Cys Leu Ile Cys Trp Lys
            420

<210> SEQ ID NO 9
<211> LENGTH: 424
<212> TYPE: PRT
<213> ORGANISM: Artificial
<220> FEATURE:
<223> OTHER INFORMATION: mutant synthetase

<400> SEQUENCE: 9

Met Ala Ser Ser Asn Leu Ile Lys Gln Leu Gln Glu Arg Gly Leu Val
1               5                   10                  15

Ala Gln Val Thr Asp Glu Glu Ala Leu Ala Glu Arg Leu Ala Gln Gly
            20                  25                  30

Pro Ile Ala Leu Val Cys Gly Phe Asp Pro Thr Ala Asp Ser Leu His
        35                  40                  45

Leu Gly His Leu Val Pro Leu Leu Cys Leu Lys Arg Phe Gln Gln Ala
    50                  55                  60

Gly His Lys Pro Val Ala Leu Val Gly Gly Ala Thr Gly Leu Ile Gly
65                  70                  75                  80

Asp Pro Ser Phe Lys Ala Ala Glu Arg Lys Leu Asn Thr Glu Glu Thr
                85                  90                  95

Val Gln Glu Trp Val Asp Lys Ile Arg Lys Gln Val Ala Pro Phe Leu
            100                 105                 110

```
Asp Phe Asp Cys Gly Glu Asn Ser Ala Ile Ala Ala Asn Asn Tyr Asp
            115                 120                 125

Trp Phe Gly Asn Met Asn Val Leu Thr Phe Leu Arg Asp Ile Gly Lys
            130                 135                 140

His Phe Ser Val Asn Gln Met Ile Asn Lys Glu Ala Val Lys Gln Arg
145                 150                 155                 160

Leu Asn Arg Glu Asp Gln Gly Ile Ser Phe Thr Glu Phe Ser Tyr Asn
                165                 170                 175

Leu Leu Gln Gly Tyr Ser Met Ala Cys Ala Asn Lys Gln Tyr Gly Val
            180                 185                 190

Val Leu Gln Ile Gly Gly Ser Asp Gln Trp Gly Asn Ile Thr Ser Gly
            195                 200                 205

Ile Asp Leu Thr Arg Arg Leu His Gln Asn Gln Val Phe Gly Leu Thr
            210                 215                 220

Val Pro Leu Ile Thr Lys Ala Asp Gly Thr Lys Phe Gly Lys Thr Glu
225                 230                 235                 240

Gly Gly Ala Val Trp Leu Asp Pro Lys Lys Thr Ser Pro Tyr Lys Phe
                245                 250                 255

Tyr Gln Phe Trp Ile Asn Thr Ala Asp Ala Asp Val Tyr Arg Phe Leu
            260                 265                 270

Lys Phe Phe Thr Phe Met Ser Ile Glu Glu Ile Asn Ala Leu Glu Glu
            275                 280                 285

Glu Asp Lys Asn Ser Gly Lys Ala Pro Arg Ala Gln Tyr Val Leu Ala
            290                 295                 300

Glu Gln Val Thr Arg Leu Val His Gly Glu Glu Gly Leu Gln Ala Ala
305                 310                 315                 320

Lys Arg Ile Thr Glu Cys Leu Phe Ser Gly Ser Leu Ser Ala Leu Ser
                325                 330                 335

Glu Ala Asp Phe Glu Gln Leu Ala Gln Asp Gly Val Pro Met Val Glu
            340                 345                 350

Met Glu Lys Gly Ala Asp Leu Met Gln Ala Leu Val Asp Ser Glu Leu
            355                 360                 365

Gln Pro Ser Arg Gly Gln Ala Arg Lys Thr Ile Ala Ser Asn Ala Ile
            370                 375                 380

Thr Ile Asn Gly Glu Lys Gln Ser Asp Pro Glu Tyr Phe Phe Lys Glu
385                 390                 395                 400

Glu Asp Arg Leu Phe Gly Arg Phe Thr Leu Leu Arg Arg Gly Lys Lys
                405                 410                 415

Asn Tyr Cys Leu Ile Cys Trp Lys
            420
```

SITE SPECIFIC INCORPORATION OF HEAVY ATOM-CONTAINING UNNATURAL AMINO ACIDS INTO PROTEINS FOR STRUCTURE DETERMINATION

CROSS-REFERENCE TO RELATED APPLICATIONS

This application is a non-provisional utility patent application claiming priority to and benefit of the following prior provisional patent applications: U.S. Ser. No. 60/574,554, filed May 25, 2004, entitled "SITE SPECIFIC INCORPORATION OF HEAVY ATOM-CONTAINING UNNATURAL AMINO ACIDS INTO PROTEINS FOR STRUCTURE DETERMINATION" by Jianming Xie et al., and U.S. Ser. No. 60/602,048, filed Aug. 16, 2004, entitled "SITE SPECIFIC INCORPORATION OF HEAVY ATOM-CONTAINING UNNATURAL AMINO ACIDS INTO PROTEINS FOR STRUCTURE DETERMINATION" by Jianming Xie et al., each of which is incorporated herein by reference in its entirety for all purposes.

STATEMENT AS TO RIGHTS TO INVENTIONS MADE UNDER FEDERALLY SPONSORED RESEARCH AND DEVELOPMENT

This invention was made with United States Government support from National Institutes of Health Grant Number GM62159 and grant number DE-FG02-03ER46051 from the Department of Energy. As such, the Government may have certain rights to the invention.

FIELD OF THE INVENTION

The invention is in the field of translation biochemistry. The invention relates to compositions of orthogonal aminoacyl-tRNA synthetases, and pairs of orthogonal aminoacyl-tRNA synthetases and orthogonal tRNAs, that incorporate unnatural amino acids, e.g., heavy atom-containing amino acids, into proteins in response to selector codons such as stop selector codons. The invention also relates to methods of producing proteins in cells using such pairs and to related kits. In addition, the invention pertains to novel compositions and methods for the determination of protein crystal structure using unnatural amino acids that are incorporated into the protein under study.

BACKGROUND OF THE INVENTION

Anomalous signals within proteins can be used to derive phase information for crystal structure determination by single wavelength anomalous dispersion (SAD) experiments (Hendrickson and Teeter (1981) "Structure of the hydrophobic protein crambin determined directly from the anomalous scattering of sulfur" Nature 290:107-113 and Debreczeni et al. (2003) "In-house measurement of the sulfur anomalous signal and its use for phasing" Acta Crystallogr D 59:688-696). Unfortunately, the weak anomalous signals derived from sulfur or other atoms present in proteins result in the stringent need for highly redundant data (Dauter et al. (1999) "Can anomalous signal of sulfur become a tool for solving protein crystal structures?" J Mol Biol 289:83-92), which has limited the use of in-house SAD phasing. Heavy atoms, such as U, Ba, Xe, Te, and I, have strong anomalous signals at the CuK$\alpha$ wavelength, but it is generally difficult to place them at precise positions in a protein.

The anomalous signal ($\delta f''$) of iodine at the CuK$\alpha$ wavelength typically used with in-house generators (1.5418 Å) is 6.85e$^-$, six times of that of selenium (1.14e$^-$) and twelve times of that of sulfur (0.56e$^-$) (Dauter et al. (2002) "Jolly SAD" Acta Crystallogr D 58:494-506). Therefore, the selective introduction of an iodine atom into proteins can reduce the high data redundancy and high-solvent content necessary for selenium or sulfur phasing (Dauter et al. (1999) J Mol Biol 289:83-92). The genetic incorporation of heavy atoms as described herein (e.g., genetic incorporation of iodoPhe) offers a number of advantages over current approaches for introducing heavy atoms for SAD phasing. One such method involves substituting bound water molecules at the surface of the protein with either halides or metal ions by soaking the crystal in a solution containing the relevant ions (Dauter et al. (2000) "Novel approach to phasing proteins: derivatization by short cryo-soaking with halides" Acta Crystallogr D 56(Pt 2):232-237 and Nagem et al. (2001) "Protein crystal structure solution by fast incorporation of negatively and positively charged anomalous scatterers" Acta Crystallogr D 57:996-1002). Unfortunately, this approach can produce a number of low occupancy sites whose positions must be determined before phases can be derived. Another method, telluromethionine (TeMet) incorporation (Boles et al. (1994) "Bio-incorporation of telluromethionine into buried residues of dihydrofolate reductase" Nat Struct Biol 1:283-284 and Budisa et al. (1997) "Bioincorporation of telluromethionine into proteins: a promising new approach for X-ray structure analysis of proteins" J Mol Biol 270:616-623), provides a significant anomalous signal at the CuK$\alpha$ wavelength ($\delta f''$=6.4 e$^-$), but is limited by the extreme sensitivity of TeMet to oxidation, toxicity to the host organism, and difficulty in achieving quantitative replacement of Met with TeMet.

Among other benefits, the present invention provides compositions and methods that overcome the above noted difficulties by enabling site-specific, high efficiency incorporation of heavy atoms into proteins. For example, by genetically encoding iodoPhe with a unique codon, tRNA, and aminoacyl-tRNA synthetase, this amino acid can be quantitatively and efficiently incorporated at any desired site in a protein. Furthermore, the substitution of large hydrophobic residues with iodoPhe, at either surface or internal sites, is likely to cause minimal perturbation of the protein structure. A complete understanding of the invention will be obtained upon review of the following.

SUMMARY OF THE INVENTION

The present invention provides novel orthogonal amino acyl tRNA-synthetases that preferentially charge an orthogonal tRNA with a heavy atom-containing amino acid, e.g., iodoPhe or bromoPhe. The invention also provides novel translation systems that produce protein products using the orthogonal amino acyl tRNA-synthetases and orthogonal tRNAs. Related kits and methods for producing proteins including heavy atom-containing amino acids, e.g., brominated or iodinated amino acids, are also described. These techniques and compositions find a number of uses as described herein, particularly in protein structure determination.

In one aspect, the invention provides a translation system that includes an orthogonal aminoacyl-tRNA synthetase (O-RS). In one class of embodiments, the O-RS comprises an amino acid sequence of SEQ ID NO:3 or SEQ ID NO:4 or an amino acid sequence encoded by a polynucleotide sequence selected from the group consisting of SEQ ID NOs:1-2 and a complementary polynucleotide sequence thereof. In certain embodiments, the O-RS comprises an amino acid sequence that is at least 90% identical to that of a naturally occurring tyrosyl aminoacyl-tRNA synthetase (TyrRS) and that includes two or more (e.g., three or more, four or more, or five) amino acids selected from the group consisting of: leucine at a position corresponding to Tyr32 of *M. jannaschii* TyrRS, serine or glutamate at a position corresponding to Glu107 of *M. jannaschii* TyrRS, proline at a position corresponding to Asp158 of *M. jannaschii* TyrRS, leucine or arginine at a position corresponding to Ile159 of *M. jannaschii* TyrRS, and glutamate or arginine at a position corresponding to Leu162 of *M. jannaschii* TyrRS. The O-RS is optionally derived from a *M. jannaschii* aminoacyl-tRNA synthetase. In certain embodiments, the O-RS preferentially aminoacylates an orthogonal tRNA with an efficiency of at least 50% of the efficiency of a polypeptide comprising an amino acid sequence of SEQ ID NO:3 or SEQ ID NO:4 with a brominated or iodinated amino acid, with the proviso that the orthogonal aminoacyl-tRNA synthetase does not comprise any one of SEQ ID NOs:6-9. The brominated or iodinated amino acid can be, e.g., L-2-iodophenylalanine, L-3-iodophenylalanine, L-2-iodotyrosine, L-3-iodotyrosine, L-2-bromophenylalanine, L-3-bromophenylalanine, L-2-bromotyrosine, or L-3-bromotyrosine. In a preferred class of embodiments, the brominated or iodinated amino acid is L-4-bromophenylalanine (bromoPhe) or L-4-iodophenylalanine (iodoPhe).

In one class of embodiments, the translation system is in a cell, for example, an *E. coli* cell. The O-RS is optionally encoded by one or more nucleic acids in the cell. Similarly, the orthogonal tRNA (O-tRNA) preferentially charged by the O-RS is optionally also encoded by one or more nucleic acids in the cell. In other embodiments, the translation system comprises an in vitro translation system, e.g., a cellular extract.

The translation system typically also includes an orthogonal tRNA, e.g., an O-tRNA preferentially charged by the O-RS with a brominated or iodinated amino acid. In some embodiments, the O-tRNA comprises or is encoded by the polynucleotide sequence of SEQ ID NO:5 or a conservative variant thereof. The O-tRNA optionally recognizes (i.e., includes a recognition sequence for) a selector codon that is a stop codon, e.g., an amber codon.

The translation system optionally includes a target nucleic acid that comprises a selector codon recognized by the O-tRNA preferentially charged by the O-RS, e.g., with a brominated or iodinated amino acid. The translation system can also include a protein encoded by the target nucleic acid, which protein comprises the brominated or iodinated amino acid (e.g., bromoPhe or iodoPhe).

One general class of embodiments provides a composition including an orthogonal aminoacyl-tRNA synthetase comprising an amino acid sequence of SEQ ID NO:3 or SEQ ID NO:4 or a conservative variant thereof. The composition optionally also includes an orthogonal tRNA preferentially aminoacylated by the O-RS with a brominated or iodinated amino acid (e.g., iodoPhe or bromoPhe). For example, the O-tRNA can comprise or be encoded by the polynucleotide sequence of SEQ ID NO:5 or a conservative variant thereof.

The composition can include a cell (e.g., a eukaryotic or non-eukaryotic cell, e.g., an *E. coli* cell), for example, a cell in which the O-RS is present. The O-RS is optionally encoded by one or more nucleic acids in the cell. The composition can incorporate a translation system. In compositions that incorporate a cell and where the O-RS is encoded by one or more nucleic acids in the cell, the cell can further include an orthogonal-tRNA (O-tRNA) that recognizes a selector codon and a brominated or iodinated amino acid, e.g., where the O-RS preferentially aminoacylates the O-tRNA with the brominated or iodinated amino acid. In some embodiments, the cell includes a target nucleic acid that encodes a protein of interest, where the target nucleic acid encodes the selector codon that is recognized by the O-tRNA. The cell can also include the protein encoded by the target nucleic acid, which protein comprises the brominated or iodinated amino acid.

A related general class of embodiments provides a nucleic acid comprising a polynucleotide sequence that encodes an amino acid sequence of SEQ ID NO:3 or SEQ ID NO:4 or a conservative variant thereof or a polynucleotide sequence of SEQ ID NO:1 or SEQ ID NO:2 or a complementary polynucleotide sequence thereof. A vector (e.g., an expression vector) can comprise or encode a nucleic acid of the invention.

Kits are also a feature of the invention. For example, a kit for producing a protein with a brominated or iodinated amino acid at a specified position is provided, where the kit includes a cell comprising an orthogonal tRNA that functions in the cell and recognizes a selector codon and an orthogonal aminoacyl-tRNA synthetase, packaged in one or more containers. The orthogonal aminoacyl-tRNA synthetase includes an amino acid sequence that is at least 90% identical to that of a naturally occurring tyrosyl aminoacyl-tRNA synthetase (TyrRS) and that comprises two or more (e.g., three or more, four or more, or five) amino acids selected from the group consisting of: leucine at a position corresponding to Tyr32 of *M. jannaschii* TyrRS, serine or glutamate at a position corresponding to Glu107 of *M. jannaschii* TyrRS, proline at a position corresponding to Asp158 of *M. jannaschii* TyrRS, leucine or arginine at a position corresponding to Ile159 of *M. jannaschii* TyrRS, and glutamate or arginine at a position corresponding to Leu162 of *M. jannaschii* TyrRS. In one embodiment, the kit further includes the brominated or iodinated amino acid (e.g., bromoPhe or iodoPhe), instructional materials for producing the protein, an appropriate cell growth medium, reagents for introducing a target nucleic acid encoding the protein of interest and including the selector codon into the cell, and/or the like.

Methods of producing a protein in a cell (e.g., a non-eukaryotic cell, such as an *E. coli* cell or the like, or a eukaryotic cell) with a heavy atom-containing amino acid (e.g., a brominated or iodinated amino acid, e.g., bromoPhe or iodoPhe) at a specified position are also a feature of the invention. For example, the methods can include providing a cell comprising a nucleic acid that comprises at least one selector codon and that encodes the protein, an orthogonal tRNA that functions in the cell and recognizes the selector codon, and an orthogonal aminoacyl-tRNA synthetase. The O-RS comprises an amino acid sequence that is at least 90% identical to that of a naturally occurring tyrosyl aminoacyl-tRNA synthetase (TyrRS) and comprises two or more (e.g., three or more, four or more, or five) amino acids selected from the group consisting of: leucine at a position corresponding to Tyr32 of *M. jannaschii* TyrRS, serine or glutamate at a position corresponding to Glu107 of *M. jannaschii* TyrRS, proline at a position corresponding to Asp158 of *M. jannaschii* TyrRS, leucine or arginine at a position corresponding to Ile159 of *M. jannaschii* TyrRS, and glutamate or arginine at a position corresponding to Leu162 of *M. jannaschii* TyrRS. The O-RS optionally comprises an amino acid sequence which includes any one of SEQ ID NOs:3-4. Similarly, the O-tRNA optionally comprises or is encoded by a polynucleotide sequence as set forth in SEQ ID NO:5, or a conservative variant thereof. The cell is grown in an appropriate medium. The brominated or iodinated amino acid (or other heavy atom-containing amino acid) is provided and incorporated into the specified position in the protein during translation of the nucleic acid with the at least one selector codon, thereby producing the protein.

In one aspect, the invention provides methods of determining a protein structure. In the methods, a protein with a heavy atom-containing amino acid at a specified position is provided by expressing the protein in a translation system that includes an orthogonal tRNA and an orthogonal aminoacyl-tRNA synthetase which preferentially aminoacylates the orthogonal tRNA with the heavy atom-containing amino acid. The protein including the heavy atom-containing amino acid is crystallized, thereby creating a heavy atom-containing protein crystal. The structure of the protein is determined by a process that comprises collecting diffraction data from the heavy atom-containing protein crystal at a single wavelength (e.g., 1.5418 Å) and measuring anomalous differences between Friedel mates.

The protein can be expressed in an in vivo or in vitro translation system, e.g., as described herein. In certain embodiments, the orthogonal aminoacyl-tRNA synthetase comprises an amino acid sequence of SEQ ID NO:3 or SEQ ID NO:4 or a conservative variant thereof. Similarly, the orthogonal-tRNA can comprise a polynucleotide sequence of SEQ ID NO:5 or a conservative variant thereof.

The heavy atom-containing amino acid can be essentially any suitable heavy atom-containing amino acid, e.g., one whose introduction is not predicted to significantly perturb the protein's structure. For example, the heavy atom-containing amino acid can be a brominated or iodinated amino acid. In a preferred class of embodiments, the brominated or iodinated amino acid is L-4-bromophenylalanine or L-4-iodophenylalanine.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 4 provides the nucleotide (DNA) and corresponding amino acid sequences of two aminoacyl-tRNA-synthetase mutant genes (IodoPheRS #1, Panel A, and IodoPheRS #2, Panel B) that have the ability to work in a tRNA/synthetase orthogonal pair and charge a mutant tRNA and result in the incorporation of p-iodo-phenylalanine (or p-bromo-phenylalanine) into a nascent protein, e.g., in vivo as described herein. IodoPheRS #1 nucleotide and amino acid sequences are SEQ ID NOs:1 and 3, respectively; IodoPheRS #2 nucleotide and amino acid sequences are SEQ ID NOs:2 and 4, respectively.

FIG. 5 provides the nucleotide sequence of a mutant tRNA (SEQ ID NO:5) that can work in an orthogonal pair of the invention for the incorporation of p-iodo-phenylalanine (or p-bromo-phenylalanine) into proteins, e.g., in vivo.

DEFINITIONS

Figure 1:
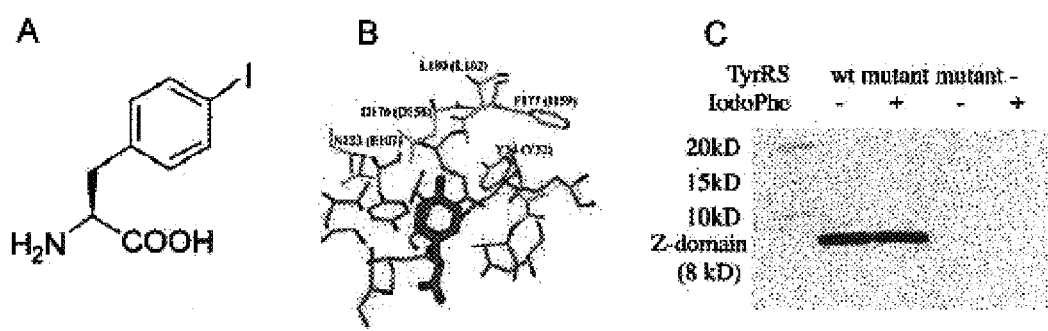
FIG. 1 Panel A shows the structure of p-iodo-L-phenylalanine (iodoPhe). Panel B illustrates a portion of the crystal structure of the *B. stearothermophilus* TyrRS-tyrosyl adenylate complex. The five residues of *M. jannaschii* TyrRS which were randomized are in parenthesis (i.e., $Tyr^{32}$, $Glu^{107}$, $Asp^{158}$, $Ile^{159}$ and $Leu^{162}$). Residues were selected based on observed contacts between the homologous *B. stearothermophilus* TyrRS residues ($Tyr^{34}$, $Asn^{123}$, $Asp176$, $Phe^{177}$ and $Leu^{180}$) and tyrosyl adenylate in the crystal structure. Panel C is a photograph of a gel, illustrating verification of iodoPhe incorporation in response to an amber codon by SDS-PAGE and silver staining of the expressed amber mutant Z-domain protein. Proteins were purified by $Ni^{2+}$ affinity chromatography.

Unless defined otherwise, all technical and scientific terms used herein have the same meaning as commonly understood by one of ordinary skill in the art to which the invention pertains. The following definitions supplement those in the art and are directed to the current application and are not to be imputed to any related or unrelated case, e.g., to any commonly owned patent or application. Although any methods and materials similar or equivalent to those described herein can be used in the practice for testing of the present invention, the preferred materials and methods are described herein. Accordingly, the terminology used herein is for the purpose of describing particular embodiments only, and is not intended to be limiting.

As used in this specification and the appended claims, the singular forms "a", "an" and "the" include plural referents unless the content clearly dictates otherwise. Thus, for example, reference to "a cell" includes a combination of two or more cells; reference to "bacteria" includes mixtures of bacteria, and the like.

Orthogonal tRNA: As used herein, an orthogonal tRNA (O-tRNA) is a tRNA that is orthogonal to a translation system of interest. The O-tRNA can exist charged with an amino acid, or in an uncharged state. It will be appreciated that an O-tRNA of the invention is advantageously used to insert essentially any amino acid, whether natural or unnatural, into a growing polypeptide, during translation, in response to a selector codon.

Orthogonal amino acid synthetase: As used herein, an orthogonal amino acid synthetase (O-RS) is an enzyme that preferentially aminoacylates an O-tRNA with an amino acid in a translation system of interest.

Orthogonal: As used herein, the term "orthogonal" refers to a molecule (e.g., an orthogonal tRNA (O-tRNA) and/or an orthogonal aminoacyl tRNA synthetase (O-RS)) that functions with endogenous components of a cell or other translation system with reduced efficiency as compared to a corresponding molecule that is endogenous to the cell or translation system, or that fails to function when paired with endogenous components of the cell or translation system. In the context of tRNAs and aminoacyl-tRNA synthetases, orthogonal refers to an inability or reduced efficiency (e.g., less than 20% efficiency, less than 10% efficiency, less than 5% efficiency, or less than 1% efficiency), of an orthogonal tRNA to function with an endogenous tRNA synthetase compared to the ability of an appropriate (e.g., homologous or analogous) endogenous tRNA to function when paired with the endogenous complementary tRNA synthetase; or of an orthogonal aminoacyl-tRNA synthetase to function with an endogenous tRNA as compared to the ability of an appropriate endogenous tRNA synthetase to function when paired with the endogenous complementary tRNA. The orthogonal molecule lacks a functionally normal naturally occurring endogenous complementary molecule in the cell or translation system. For example, an orthogonal tRNA in a cell is aminoacylated by any endogenous RS of the cell with reduced or even undetectable efficiency, when compared to aminoacylation of an endogenous tRNA by the endogenous RS. In another example, an orthogonal RS aminoacylates any endogenous tRNA in a cell of interest with reduced or even undetectable efficiency, as compared to aminoacylation of the endogenous tRNA by a complementary endogenous RS. A second orthogonal molecule can be introduced into the cell that functions when paired with the first orthogonal molecule. For example, an orthogonal tRNA/RS pair includes introduced complementary components that function together in the cell with an efficiency (e.g., 45% efficiency, 50% efficiency, 60% efficiency, 70% efficiency, 75% efficiency, 80% efficiency, 90% efficiency, 95% efficiency, or 99% or more efficiency) as compared to that of a control, e.g., a corresponding (e.g., analogous) tRNA/RS endogenous pair, or an active orthogonal pair (e.g., a tryptophanyl or a tyrosyl orthogonal tRNA/RS pair).

Cognate: The term "cognate" refers to components that function together, e.g., an orthogonal tRNA and an orthogonal aminoacyl-tRNA synthetase that preferentially aminoacylates the orthogonal tRNA. The components can also be referred to as being "complementary."

Preferentially aminoacylates: An O-RS "preferentially aminoacylates" a cognate O-tRNA when the O-RS charges the O-tRNA with an amino acid more efficiently than it charges any endogenous tRNA in an expression system. That is, when the O-tRNA and any given endogenous tRNA are present in a translation system in approximately equal molar ratios, the O-RS will charge the O-tRNA more frequently than it will charge the endogenous tRNA. Preferably, the relative ratio of O-tRNA charged by the O-RS to endogenous tRNA charged by the O-RS is high, preferably resulting in the O-RS charging the O-tRNA exclusively, or nearly exclusively, when the O-tRNA and endogenous tRNA are present in equal molar concentrations in the translation system. The relative ratio between O-tRNA and endogenous tRNA that is charged by the O-RS, when the O-tRNA and O-RS are present at equal molar concentrations, is greater than 1:1, preferably at least about 2:1, more preferably 5:1, still more preferably 10:1, yet more preferably 20:1, still more preferably 50:1, yet more preferably 75:1, and still more preferably 95:1, 98:1, 99:1, 100:1, 500:1, 1,000:1, 5,000:1 or higher.

The O-RS "preferentially aminoacylates an O-tRNA with an unnatural amino acid" when (a) the O-RS preferentially aminoacylates the O-tRNA compared to an endogenous tRNA, and (b) where that aminoacylation is specific for the unnatural amino acid, as compared to aminoacylation of the O-tRNA by the O-RS with any natural amino acid. That is, when the unnatural and natural amino acids are present in equal molar amounts in a translation system comprising the O-RS and O-tRNA, the O-RS will load the O-tRNA with the unnatural amino acid more frequently than with the natural amino acid. Preferably, the relative ratio of O-tRNA charged with the unnatural amino acid to O-tRNA charged with the natural amino acid is high. More preferably, O-RS charges the O-tRNA exclusively, or nearly exclusively, with the unnatural amino acid. The relative ratio between charging of the O-tRNA with the unnatural amino acid and charging of the O-tRNA with the natural amino acid, when both the natural and unnatural amino acids are present in the translation system in equal molar concentrations, is greater than 1:1, preferably at least about 2:1, more preferably 5:1, still more preferably 10:1, yet more preferably 20:1, still more preferably 50:1, yet more preferably 75:1, and still more preferably 95:1, 98:1, 99:1, 100:1, 500:1, 1,000:1, 5,000:1 or higher.

Selector codon: The term "selector codon" refers to a codon recognized by the O-tRNA in the translation process and not typically recognized by an endogenous tRNA. The O-tRNA anticodon loop recognizes the selector codon on the mRNA and incorporates its amino acid, e.g., an unnatural amino acid, such as a heavy atom-containing amino acid, at this site in the polypeptide. Selector codons can include, e.g., nonsense codons, such as stop codons (e.g., amber, ochre, and opal codons), four or more base codons, rare codons, codons derived from natural or unnatural base pairs, and/or the like.

Suppressor tRNA: A suppressor tRNA is a tRNA that alters the reading of a messenger RNA (mRNA) in a given translation system, e.g., by providing a mechanism for incorporating an amino acid into a polypeptide chain in response to a selector codon. For example, a suppressor tRNA can read through, e.g., a stop codon, a four base codon, a rare codon, etc.

Suppression activity: As used herein, the term "suppression activity" refers, in general, to the ability of a tRNA (e.g., a suppressor tRNA) to allow translational read-through of a codon (e.g. a selector codon that is an amber codon or a 4-or-more base codon) that would otherwise result in the termination of translation or mistranslation (e.g., frame-shifting). Suppression activity of a suppressor tRNA can be expressed as a percentage of translational read-through activity observed compared to a second suppressor tRNA, or as compared to a control system, e.g., a control system lacking an O-RS.

The present invention provides various means by which suppression activity can be quantitated. Percent suppression of a particular O-tRNA and O-RS against a selector codon (e.g., an amber codon) of interest refers to the percentage of activity of a given expressed test marker (e.g., LacZ), that includes a selector codon, in a nucleic acid encoding the expressed test marker, in a translation system of interest, where the translation system of interest includes an O-RS and an O-tRNA, as compared to a positive control construct, where the positive control lacks the O-tRNA, the O-RS and the selector codon. Thus, for example, if an active positive control marker construct that lacks a selector codon has an observed activity of X in a given translation system, in units relevant to the marker assay at issue, then percent suppression of a test construct comprising the selector codon is the percentage of X that the test marker construct displays under essentially the same environmental conditions as the positive control marker was expressed under, except that the test marker construct is expressed in a translation system that also includes the O-tRNA and the O-RS. Typically, the translation system expressing the test marker also includes an amino acid that is recognized by the O-RS and O-tRNA. Optionally, the percent suppression measurement can be refined by comparison of the test marker to a "background" or "negative" control marker construct, which includes the same selector codon as the test marker, but in a system that does not include the O-tRNA, O-RS and/or relevant amino acid recognized by the O-tRNA and/or O-RS. This negative control is useful in normalizing percent suppression measurements to account for background signal effects from the marker in the translation system of interest.

Suppression efficiency can be determined by any of a number of assays known in the art. For example, a β-galactosidase reporter assay can be used, e.g., a derivatized lacZ plasmid (where the construct has a selector codon n the lacZ nucleic acid sequence) is introduced into cells from an appropriate organism (e.g., an organism where the orthogonal components can be used) along with plasmid comprising an O-tRNA of the invention. A cognate synthetase can also be introduced (either as a polypeptide or a polynucleotide that encodes the cognate synthetase when expressed). The cells are grown in media to a desired density, e.g., to an $OD_{600}$ of about 0.5, and β-galactosidase assays are performed, e.g., using the BetaFluor™ β-Galactosidase Assay Kit (Novagen). Percent suppression can be calculated as the percentage of activity for a sample relative to a comparable control, e.g., the value observed from the derivatized lacZ construct, where the construct has a corresponding sense codon at desired position rather than a selector codon.

Translation system: The term "translation system" refers to the components that incorporate an amino acid into a growing polypeptide chain (protein). Components of a translation system can include, e.g., ribosomes, tRNAs, synthetases, mRNA, and the like. The O-tRNA and/or the O-RSs of the invention can be added to or be part of an in vitro or in vivo translation system, e.g., in a non-eukaryotic cell, e.g., a bacterium (such as *E. coli*), or in a eukaryotic cell, e.g., a yeast cell, a mammalian cell, a plant cell, an algae cell, a fungus cell, an insect cell, and/or the like.

Unnatural amino acid: As used herein, the term "unnatural amino acid" refers to any amino acid, modified amino acid, and/or amino acid analog, such as a heavy atom-containing amino acid, that is not one of the 20 common naturally occurring amino acids or the rare natural amino acids selenocysteine or pyrrolysine.

Derived from: As used herein, the term "derived from" refers to a component that is isolated from or made using a specified molecule or organism or information from the specified molecule or organism.

Positive selection or screening marker: As used herein, the term "positive selection or screening marker" refers to a marker that when present, e.g., expressed, activated, or the like, results in identification of a cell that comprises a trait corresponding to the marker, e.g., cells with the positive selection marker, from those without the trait.

Negative selection or screening marker: As used herein, the term "negative selection or screening marker" refers to a marker that, when present, e.g., expressed, activated, or the like, allows identification of a cell that does not comprise a selected property or trait (e.g., as compared to a cell that does possess the property or trait).

Reporter: As used herein, the term "reporter" refers to a component that can be used to identify and/or select target components of a system of interest. For example, a reporter can include a protein, e.g., an enzyme, that confers antibiotic resistance or sensitivity (e.g., β-lactamase, chloramphenicol acetyltransferase (CAT), and the like), a fluorescent screening marker (e.g., green fluorescent protein (e.g., (GFP), YFP, EGFP, RFP, etc.), a luminescent marker (e.g., a firefly luciferase protein), an affinity based screening marker, or positive or negative selectable marker genes such as lacZ, β-gal/lacZ (β-galactosidase), Adh (alcohol dehydrogenase), his3, ura3, leu2, lys2, or the like.

Eukaryote: As used herein, the term "eukaryote" refers to organisms belonging to the phylogenetic domain Eucarya, such as animals (e.g., mammals, insects, reptiles, birds, etc.), ciliates, plants (e.g., monocots, dicots, algae, etc.), fungi, yeasts, flagellates, microsporidia, protists, etc.

Non-eukaryote: As used herein, the term "non-eukaryote" refers to non-eukaryotic organisms. For example, a non-eukaryotic organism can belong to the Eubacteria (e.g., *Escherichia coli, Thermus thermophilus, Bacillus stearothermophilus*, etc.) phylogenetic domain, or the Archaea (e.g., *Methanococcus jannaschii* (Mj), *Methanosarcina mazei* (Mm), *Methanobacterium thermoautotrophicum* (Mt), *Methanococcus maripaludis, Methanopyrus kandleri, Halobacterium* such as *Haloferax volcanii* and *Halobacterium* species NRC-1, *Archaeoglobus fulgidus* (Af),*Pyrococcus furiosus* (Pf), *Pyrococcus horikoshii* (Ph), *Pyrobaculum aerophilum, Pyrococcus abyssi, Sulfolobus solfataricus* (Ss), *Sulfolobus tokodaii, Aeuropyrum pernix* (Ap), *Thermoplasma acidophilum, Thermoplasma volcanium*, etc.) phylogenetic domains.

Conservative variant: As used herein, the term "conservative variant," in the context of a translation component, refers to a translation component, e.g., a conservative variant O-tRNA or a conservative variant O-RS, that functionally performs similarly to a base component that the conservative variant is similar to, e.g., an O-tRNA or O-RS, having variations in the sequence as compared to a reference O-tRNA or O-RS. For example, an O-RS will aminoacylate a complementary O-tRNA or a conservative variant O-tRNA with an unnatural amino acid, e.g., a heavy atom-containing amino acid, although the O-tRNA and the conservative variant O-tRNA do not have the same sequence. The conservative variant can have, e.g., one variation, two variations, three variations, four variations, or five or more variations in sequence, as long as the conservative variant is complementary to the corresponding O-tRNA or O-RS.

Selection or screening agent: As used herein, the term "selection or screening agent" refers to an agent that, when present, allows for selection/screening of certain components from a population. For example, a selection or screening agent can be, but is not limited to, e.g., a nutrient, an antibiotic, a wavelength of light, an antibody, an expressed polynucleotide, or the like. The selection agent can be varied, e.g., by concentration, intensity, etc.

In response to: As used herein, the term "in response to" refers to the process in which a tRNA of the invention recognizes a selector codon and incorporates a relevant amino acid, e.g., an unnatural amino acid such as a heavy atom-containing amino acid, which is carried by the tRNA into the growing polypeptide chain.

Encode: As used herein, the term "encode" refers to any process whereby the information in a polymeric macromolecule or sequence string is used to direct the production of a second molecule or sequence string that is different from the first molecule or sequence string. As used herein, the term is used broadly, and can have a variety of applications. In one aspect, the term "encode" describes the process of semi-conservative DNA replication, where one strand of a double-stranded DNA molecule is used as a template to encode a newly synthesized complementary sister strand by a DNA-dependent DNA polymerase.

In another aspect, the term "encode" refers to any process whereby the information in one molecule is used to direct the production of a second molecule that has a different chemical nature from the first molecule. For example, a DNA molecule can encode an RNA molecule (e.g., by the process of transcription incorporating a DNA-dependent RNA polymerase enzyme). Also, an RNA molecule can encode a polypeptide, as in the process of translation. When used to describe the process of translation, the term "encode" also extends to the triplet codon that encodes an amino acid. In some aspects, an RNA molecule can encode a DNA molecule, e.g., by the process of reverse transcription incorporating an RNA-dependent DNA polymerase. In another aspect, a DNA molecule can encode a polypeptide, where it is understood that "encode" as used in that case incorporates both the processes of transcription and translation.

Heavy atom: A "heavy atom" is an atom whose presence in a crystal can produce a measurable difference in the diffraction pattern of the crystal as compared to the diffraction pattern of a corresponding crystal lacking the heavy atom. For example, a heavy atom for use in SAD or MAD phasing techniques typically has a resonance signal at an energy that is easily accessible to standard x-ray sources, and that therefore produces an anomalous signal at a convenient wavelength. As another example, a heavy atom for use in single or multiple isomorphous replacement phasing techniques typically has an atomic number that is considerably greater than the atomic numbers of the other atoms present, e.g., an atomic number greater than the C, N, O, and S atoms present in a protein or protein crystal.

Friedel mates: "Friedel mates" are the members of a Bijvoet pair and are identified by indices h,k,l and -h,-k,-l.

Nucleic acid: The term "nucleic acid" or "polynucleotide" encompasses any physical string of monomer units that can be corresponded to a string of nucleotides, including a polymer of nucleotides (e.g., a typical DNA or RNA polymer), PNAs, modified oligonucleotides (e.g., oligonucleotides comprising nucleotides that are not typical to biological RNA or DNA, such as 2'-O-methylated oligonucleotides), and the like. A nucleic acid can be e.g., single-stranded or double-stranded. Unless otherwise indicated, a particular nucleic acid sequence of this invention optionally comprises or encodes complementary sequences, in addition to any sequence explicitly indicated.

Polypeptide: A "polypeptide" is a polymer comprising two or more amino acid residues (e.g., a peptide or a protein). The polymer can additionally comprise non-amino acid elements such as labels, quenchers, blocking groups, or the like and can optionally comprise modifications such as glycosylation or the like. The amino acid residues of the polypeptide can be natural or non-natural and can be unsubstituted, unmodified, substituted or modified.

Amino acid sequence: An "amino acid sequence" is a polymer of amino acid residues (a protein, polypeptide, etc.) or a character string representing an amino acid polymer, depending on context.

Polynucleotide sequence: A "polynucleotide sequence" or "nucleotide sequence" is a polymer of nucleotides (an oligonucleotide, a DNA, a nucleic acid, etc.) or a character string representing a nucleotide polymer, depending on context. From any specified polynucleotide sequence, either the given nucleic acid or the complementary polynucleotide sequence (e.g., the complementary nucleic acid) can be determined.

Numbering of a given amino acid or nucleotide polymer "corresponds to numbering" of a selected amino acid polymer or nucleic acid when the position of any given polymer component (amino acid residue, incorporated nucleotide, etc.) is designated by reference to the same residue position in the selected amino acid or nucleotide, rather than by the actual position of the component in the given polymer.

A variety of additional terms are defined or otherwise characterized herein.

DETAILED DESCRIPTION OF THE INVENTION

Although, with few exceptions, the genetic codes of all known organisms encode the same twenty amino acids, all that is required to add a new amino acid to the repertoire of an organism is a unique tRNA/aminoacyl-tRNA synthetase pair, a source of the amino acid, and a unique selector codon that specifies the amino acid (Furter (1998) Protein Sci., 7:419-426). Previously, we have shown that the amber nonsense codon, TAG, together with orthogonal *M. jannaschii* and *E. coli* tRNA/synthetase pairs can be used to genetically encode a variety a variety of amino acids with novel properties in *E. coli* (Wang et al., (2000) J. Am. Chem. Soc.,122:5010-5011; Wang et al., (2001) Science, 292:498-500; Wang et al., (2003) Proc. Natl. Acad. Sci. U. S. A.,100:56-61; Chin et al., (2002) Proc. Natl. Acad. Sci. U. S. A., 99:11020-11024), and yeast (Chin and Schultz, (2002) ChemBioChem, 3:1135-1137; Chin et al. (2003) Science 301:964-967), respectively.

In order to add additional synthetic amino acids, such as heavy atom-containing amino acids, to the genetic code, in vivo, new orthogonal pairs of an aminoacyl-tRNA synthetase and a tRNA are needed that can function efficiently in the translational machinery, but that are "orthogonal" to the translation system at issue, meaning that the pairs function independently of the synthetases and tRNAs endogenous to the translation system. Desired characteristics of an orthologous pair include a tRNA that decodes or recognizes only a specific new codon, e.g., a selector codon, that is not decoded by any endogenous tRNA, and an aminoacyl-tRNA synthetase that preferentially aminoacylates (or charges) its cognate tRNA with only a specific non-natural amino acid, e.g., a heavy atom-containing amino acid. The O-tRNA is also desirably not aminoacylated by endogenous synthetases. For example, in *E. coli*, an orthogonal pair will include an aminoacyl-tRNA synthetase that does not substantially aminoacylate any of the endogenous tRNAs, e.g., of which there are 40 in *E. coli*, and an orthogonal tRNA that is not substantially aminoacylated by any of the endogenous synthetases, e.g., of which there are 21 in *E. coli*.

Here we report the generation of new orthogonal synthetase/tRNA pairs that efficiently and selectively incorporate the heavy atom-containing amino acids iodoPhe and bromoPhe into proteins in response to the amber codon.

In one aspect, this invention provides compositions and kits including orthogonal tRNA synthetases and orthogonal tRNA-aminoacyl-tRNA synthetase pairs, e.g., O-tRNA/O-

RS pairs that can be used to incorporate unnatural amino acids, e.g., heavy atom-containing amino acids, into proteins of interest. Related methods are also described. An example orthogonal aminoacyl-tRNA synthetase of the invention preferentially aminoacylates (or charges) its O-tRNA with iodoPhe or bromoPhe. The O-tRNA/O-RS pair is capable of mediating incorporation of the iodoPhe or bromoPhe into a protein that is encoded by a polynucleotide which comprises a selector codon that is recognized by the O-tRNA, e.g., in vivo. The anticodon loop of the O-tRNA recognizes the selector codon on an mRNA and incorporates its amino acid, e.g., iodoPhe or bromoPhe, at the corresponding site in the polypeptide.

Site-specific, efficient incorporation of heavy atom-containing amino acids (e.g., iodoPhe or bromoPhe) into proteins facilitates solution of protein structures by x-ray crystallography. Derivatization of proteins with heavy atoms is commonly used to permit phase determination, and site-specific incorporation of heavy atoms using the methods and compositions of the present invention provides flexibility in choosing derivatization site and heavy atom numbers. In addition, production of heavy atom-containing proteins in vivo by the methods described herein can improve yield of derivatized protein.

For example, iodoPhe can be incorporated using the O-tRNA/O-RS pairs described herein, facilitating SAD phasing. Thus, the invention also provides methods of determining a protein structure, in which an O-tRNA/O-RS pair is used to incorporate a heavy atom into the protein. The heavy atom is used in phase determination, e.g., by SAD.

Orthogonal tRNAs, Orthogonal Aminoacyl-tRNA Synthetases, and Pairs thereof

Translation systems that are suitable for making proteins that include one or more unnatural amino acids are described, e.g., in International Publication Numbers WO 2002/086075, entitled "Methods and composition for the production of orthogonal tRNA-aminoacyl-tRNA synthetase pairs" and WO 2002/085923, entitled "In vivo incorporation of unnatural amino acids." In addition, see International application No. PCT/US2004/011786, filed Apr. 16, 2004. Each of these applications is incorporated herein by reference in its entirety. Such translation systems generally comprise cells (which can be non-eukaryotic cells such as *E. coli*, or eukaryotic cells such as yeast) that include an orthogonal tRNA (O-tRNA), an orthogonal aminoacyl tRNA-synthetase (O-RS), and an unnatural amino acid (in the present invention, heavy atom-containing amino acids such as iodoPhe or bromoPhe are examples of such unnatural amino acids), where the O-RS aminoacylates the O-tRNA with the unnatural amino acid. An orthogonal pair of the invention includes an O-tRNA, e.g., a suppressor tRNA, a frameshift tRNA, or the like, and an O-RS. Individual components are also provided in the invention.

In general, when an orthogonal pair recognizes a selector codon and loads an amino acid in response to the selector codon, the orthogonal pair is said to "suppress" the selector codon. That is, a selector codon that is not recognized by the translation system's (e.g., cell's) endogenous machinery is not ordinarily translated, which can result in blocking production of a polypeptide that would otherwise be translated from the nucleic acid. An O-tRNA of the invention recognizes a selector codon and includes at least about, e.g., a 45%, a 50%, a 60%, a 75%, a 80%, or a 90% or more suppression efficiency in the presence of a cognate synthetase in response to a selector codon as compared to an O-tRNA comprising or encoded by a polynucleotide sequence as set forth in the sequence listing herein (e.g., SEQ ID NO:5). The O-RS aminoacylates the O-tRNA with an unnatural amino acid of interest, such as a heavy atom-containing amino acid. The translation system (e.g., cell) uses the O-tRNA/O-RS pair to incorporate the unnatural amino acid into a growing polypeptide chain, e.g., via a nucleic acid that comprises a polynucleotide that encodes a polypeptide of interest, where the polynucleotide comprises a selector codon that is recognized by the O-tRNA.

In certain embodiments of the invention, the translation system comprises a cell (such as an *E. coli* cell) that includes an orthogonal aminoacyl-tRNA synthetase (O-RS), and optionally also an orthogonal tRNA (O-tRNA), a heavy atom-containing amino acid (e.g., a brominated or iodinated amino acid), and a nucleic acid that comprises a polynucleotide that encodes a polypeptide of interest, where the polynucleotide comprises the selector codon that is recognized by the O-tRNA. The translation system can also be a cell-free system, e.g., any of a variety of commercially available "in vitro" transcription/translation systems in combination with an O-tRNA/O-RS pair and an unnatural amino acid as described herein.

In one embodiment, the suppression efficiency of the O-RS and the O-tRNA together is about, e.g., 5 fold, 10 fold, 15 fold, 20 fold, or 25 fold or more greater than the suppression efficiency of the O-tRNA lacking the O-RS. In one aspect, the suppression efficiency of the O-RS and the O-tRNA together is at least about, e.g., 35%, 40%, 45%, 50%, 60%, 75%, 80%, or 90% or more of the suppression efficiency of an orthogonal synthetase pair as set forth in the sequence listing herein.

The cell or other translation system optionally includes multiple O-tRNA/O-RS pairs, which allows incorporation of more than one unnatural amino acid, e.g., a brominated or iodinated amino acid and another unnatural amino acid (e.g., another heavy atom containing amino acid, or a different type of unnatural amino acid). For example, the cell can further include an additional different O-tRNA/O-RS pair and a second unnatural amino acid, where this additional O-tRNA recognizes a second selector codon and this additional O-RS preferentially aminoacylates the O-tRNA with the second unnatural amino acid. For example, a cell that includes an O-tRNA/O-RS pair (where the O-tRNA recognizes, e.g., an amber selector codon) can further comprise a second orthogonal pair, where the second O-tRNA recognizes a different selector codon (e.g., an opal codon, four-base codon, or the like). Desirably, the different orthogonal pairs are derived from different sources, which can facilitate recognition of different selector codons.

The O-tRNA and/or the O-RS can be naturally occurring or can be, e.g., derived by mutation of a naturally occurring tRNA and/or RS, e.g., by generating libraries of tRNAs and/or libraries of RSs, from any of a variety of organisms and/or by using any of a variety of available mutation strategies. For example, one strategy for producing an orthogonal tRNA/aminoacyl-tRNA synthetase pair involves importing a heterologous (to the host cell) tRNA/synthetase pair from, e.g., a source other than the host cell, or multiple sources, into the host cell. The properties of the heterologous synthetase candidate include, e.g., that it does not charge any host cell tRNA, and the properties of the heterologous tRNA candidate include, e.g., that it is not aminoacylated by any host cell synthetase. A second strategy for generating an orthogonal pair involves generating mutant libraries from which to screen and/or select an O-tRNA or O-RS. These strategies can also be combined.

Orthogonal tRNA (O-tRNA)

An orthogonal tRNA (O-tRNA) of the invention desirably mediates incorporation of an unnatural amino acid, such as a heavy atom-containing amino acid (e.g., a brominated or iodinated amino acid), into a protein that is encoded by a polynucleotide that comprises a selector codon that is recognized by the O-tRNA, e.g., in vivo or in vitro. In certain embodiments, an O-tRNA of the invention includes at least about, e.g., a 45%, a 50%, a 60%, a 75%, a 80%, or a 90% or more suppression efficiency in the presence of a cognate synthetase in response to a selector codon as compared to an O-tRNA comprising or encoded by a polynucleotide sequence as set forth in the O-tRNA sequence in the sequence listing herein (e.g., SEQ ID NO:5).

Suppression efficiency can be determined by any of a number of assays known in the art. For example, a β-galactosidase reporter assay can be used, e.g., a derivatized lacZ plasmid (where the construct has a selector codon n the lacZ nucleic acid sequence) is introduced into cells from an appropriate organism (e.g., an organism where the orthogonal components can be used) along with plasmid comprising an O-tRNA of the invention. A cognate synthetase can also be introduced (either as a polypeptide or a polynucleotide that encodes the cognate synthetase when expressed). The cells are grown in media to a desired density, e.g., to an $OD_{600}$ of about 0.5, and β-galactosidase assays are performed, e.g., using the BetaFluor™ β-Galactosidase Assay Kit (Novagen). Percent suppression can be calculated as the percentage of activity for a sample relative to a comparable control, e.g., the value observed from the derivatized lacZ construct, where the construct has a corresponding sense codon at desired position rather than a selector codon.

An example O-tRNA of the invention is set forth in the sequence listing herein. See also, the examples and figures herein for sequences of exemplary O-tRNA and O-RS molecules. See also, the section entitled "Nucleic Acid and Polypeptide Sequence and Variants" herein. In an RNA molecule, such as an O-RS mRNA, or O-tRNA molecule, Thymine (T) is replaced with Uracil (U) relative to a given sequence (or vice versa for a coding DNA), or complement thereof. Additional modifications to the bases can also be present.

The invention also includes conservative variations of O-tRNAs corresponding to particular O-tRNAs herein. For example, conservative variations of an O-tRNA include those molecules that function like the particular O-tRNA, e.g., as in the sequence listing herein, and that maintain the tRNA L-shaped structure by virtue of appropriate self-complementarity, but that do not have a sequence identical to those, e.g., in the sequence listing, figures or examples herein (and, desirably, are other than wild type tRNA molecules). See also, the section herein entitled "Nucleic Acid and Polypeptide Sequence and Variants."

A composition comprising an O-tRNA can further include an orthogonal aminoacyl-tRNA synthetase (O-RS), where the O-RS preferentially aminoacylates the O-tRNA with an unnatural amino acid such as a heavy atom-containing amino acid (e.g., a brominated or iodinated amino acid). In certain embodiments, a composition including an O-tRNA can further include a translation system (e.g., in vitro or in vivo). A nucleic acid that comprises a polynucleotide that encodes a polypeptide of interest, where the polynucleotide comprises a selector codon that is recognized by the O-tRNA, or a combination of one or more of these, can also be present in the translation system. See also, the section herein entitled "Orthogonal aminoacyl-tRNA synthetase."

Methods of producing a recombinant orthogonal tRNA (O-tRNA) have been described and can be found, e.g., in international patent applications WO 2002/086075, entitled "Methods and compositions for the production of orthogonal tRNA-aminoacyl tRNA-synthetase pairs," PCT/US2004/022187 entitled "Compositions of orthogonal lysyl-tRNA and aminoacyl-tRNA synthetase pairs and uses thereof," and U.S. Ser. No. 60/479,931 and 60/496,548 entitled "Expanding the Eukaryotic Genetic Code." See also Forster et al., (2003) "Programming peptidomimetic synthetases by translating genetic codes designed de novo" PNAS 100(11):6353-6357, and Feng et al., (2003) "Expanding tRNA recognition of a tRNA synthetase by a single amino acid change" PNAS 100(10):5676-5681.

Orthogonal Aminoacyl-tRNA Synthetase (O-RS)

An O-RS of the invention preferentially aminoacylates an O-tRNA with an unnatural amino acid such as a heavy atom-containing amino acid (e.g., a brominated or iodinated amino acid, e.g., bromoPhe or iodoPhe), in vitro or in vivo. An O-RS of the invention can be provided to the translation system, e.g., a cell, by a polypeptide that includes an O-RS and/or by a polynucleotide that encodes an O-RS or a portion thereof. For example, an example O-RS comprises an amino acid sequence as set forth in the sequence listing (e.g., SEQ ID NOs:3-4) and examples herein, or a conservative variation thereof. In another example, an O-RS, or a portion thereof, is encoded by a polynucleotide sequence that encodes an amino acid comprising sequence in the sequence listing or examples herein, or a complementary polynucleotide sequence thereof. See also, the section entitled "Nucleic Acid and Polypeptide Sequence and Variants" herein.

A composition comprising an orthogonal aminoacyl-tRNA synthetase (O-RS) can further include an O-tRNA, where the O-RS preferentially aminoacylates the O-tRNA with an unnatural amino acid such as a brominated or iodinated amino acid (e.g., bromoPhe or iodoPhe). In certain embodiments, a composition including an O-RS can further include a translation system (e.g., in vitro or in vivo). A nucleic acid that comprises a polynucleotide that encodes a polypeptide of interest, where the polynucleotide comprises a selector codon that is recognized by the O-tRNA, or a combination of one or more of these can also be present in the translation system.

Any of a number of assays can be used to determine aminoacylation. These assays can be performed in vitro or in vivo. For example, in vitro aminoacylation assays are described in, e.g., Hoben and Soll (1985) Methods Enzymol. 113:55-59. Aminoacylation can also be determined by using a reporter along with orthogonal translation components and detecting the reporter in a cell expressing a polynucleotide comprising at least one selector codon that encodes a protein. See also, WO 2002/085923, entitled "In vivo incorporation of unnatural amino acids" and International Application No. PCT/US2004/011786, filed Apr. 16, 2004.

Methods for identifying an orthogonal aminoacyl-tRNA synthetase (O-RS) for use with an O-tRNA are described in the examples herein. In brief, an example method includes subjecting to selection, e.g., positive selection, a population of cells of a first species, where the cells individually comprise: 1) a member of a plurality of aminoacyl-tRNA synthetases (RSs) (e.g., the plurality of RSs can include mutant RSs, RSs derived from a species other than the first species or both mutant RSs and RSs derived from a species other than the first species); 2) the orthogonal tRNA (O-tRNA) (e.g., from one or more species); and 3) a polynucleotide that encodes a (e.g., positive) selection marker and comprises at least one selector codon. Cells are selected or screened for those that show an enhancement in suppression efficiency compared to cells lacking or with a reduced amount of the member of the plurality of RSs. Suppression efficiency can be measured by techniques known in the art and as described herein. Cells having an enhancement in suppression efficiency comprise an active RS that aminoacylates the O-tRNA. A level of aminoacylation (in vitro or in vivo) by the active RS of a first set of tRNAs from the first species is compared to the level of aminoacylation (in vitro or in vivo) by the active RS of a second set of tRNAs from the second species. The level of aminoacylation can be determined by a detectable substance (e.g., a labeled amino acid or unnatural amino acid, e.g., a labeled brominated or iodinated amino acid). The active RS that more efficiently aminoacylates the second set of tRNAs compared to the first set of tRNAs is typically selected, thereby providing an efficient (optimized) orthogonal aminoacyl-tRNA synthetase for use with the O-tRNA.

Identified O-RS can be further manipulated to alter substrate specificity of the synthetase, so that only a desired unnatural amino acid, e.g., a heavy atom-containing amino acid, but not any of the common 20 amino acids, are charged to the O-tRNA. Methods to generate an orthogonal aminoacyl tRNA-synthetase with a substrate specificity for an unnatural amino acid include mutating the synthetase, e.g., at the active site in the synthetase, at the editing mechanism site in the synthetase, at different sites by combining different domains of synthetases, or the like, and applying a selection process. A strategy based on a combination of a positive selection followed by a negative selection is optionally used. In the positive selection, suppression of the selector codon introduced at a nonessential position(s) of a positive marker allows cells to survive under positive selection pressure. In the presence of both natural and unnatural amino acids, survivors thus encode active synthetases charging the orthogonal suppressor tRNA with either a natural or unnatural amino acid. In the negative selection, suppression of a selector codon introduced at a nonessential position(s) of a negative marker removes synthetases with natural amino acid specificities. Survivors of the negative and positive selection encode synthetases that aminoacylate (charge) the orthogonal suppressor tRNA with unnatural amino acids only. These synthetases can then be subjected to further mutagenesis, e.g., DNA shuffling or other recursive mutagenesis methods.

A library of mutant O-RSs can be generated using various mutagenesis techniques known in the art. For example, the mutant RSs can be generated by site-specific mutations, random point mutations, homologous recombination, DNA shuffling or other recursive mutagenesis methods, chimeric construction or any combination thereof. For example, a library of mutant RSs can be produced from two or more other, e.g., smaller, less diverse "sub-libraries." Chimeric libraries of RSs are also included in the invention. It should be noted that libraries of tRNA synthetases from various organisms (e.g., microorganisms such as eubacteria or archaebacteria), such as libraries that comprise natural diversity (see, e.g., U.S. Pat. No. 6,238,884 to Short et al; U.S. Pat. No. 5,756,316 to Schallenberger et al; U.S. Pat. No. 5,783,431 to Petersen et al; U.S. Pat. No. 5,824,485 to Thompson et al; U.S. Pat. No. 5,958,672 to Short et al), are optionally constructed and screened for orthogonal pairs.

Once the synthetases are subjected to the positive and negative selection/screening strategy, these synthetases can then be subjected to further mutagenesis. For example, a nucleic acid that encodes the O-RS can be isolated; a set of polynucleotides that encode mutated O-RSs (e.g., by random mutagenesis, site-specific mutagenesis, recombination or any combination thereof) can be generated from the nucleic acid; and, these individual steps or a combination of these steps can be repeated until a mutated O-RS is obtained that preferentially aminoacylates the O-tRNA with the unnatural amino acid, e.g., a heavy atom-containing amino acid. In one aspect of the invention, the steps are performed multiple times, e.g., at least two times.

Additional levels of selection/screening stringency can also be used in the methods of the invention, for producing O-tRNA, O-RS, or pairs thereof. The selection or screening stringency can be varied on one or both steps of the method to produce an O-RS. This could include, e.g., varying the amount of selection/screening agent that is used, etc. Additional rounds of positive and/or negative selections can also be performed. Selecting or screening can also comprise one or more of a change in amino acid permeability, a change in translation efficiency, a change in translational fidelity, etc. Typically, the one or more change is based upon a mutation in one or more gene in an organism in which an orthogonal tRNA-tRNA synthetase pair is used to produce protein.

Additional general details for producing O-RS, and altering the substrate specificity of the synthetase, can be found, e.g., in WO 2002/086075 entitled "Methods and compositions for the production of orthogonal tRNA-aminoacyltRNA synthetase pairs," and International Application No. PCT/US2004/011786, filed Apr. 16, 2004, and PCT/US2004/022187 entitled "Compositions of orthogonal lysyl-tRNA and aminoacyl-tRNA synthetase pairs and uses thereof", filed Jul. 7, 2004.

Source And Host Organisms

The translational components of the invention can be derived from non-eukaryotic organisms. For example, the orthogonal O-tRNA can be derived from a non-eukaryotic organism (or a combination of organisms), e.g., an archaebacterium, such as *Methanococcus jannaschii, Methanobacterium thermoautotrophicum, Halobacterium* such as *Haloferax volcanii* and *Halobacterium* species NRC-1, *Archaeoglobus fulgidus, Pyrococcus furiosus, Pyrococcus horikoshii, Aeuropyrum pernix, Methanococcus maripaludis, Methanopyrus kandleri, Methanosarcina mazei, Pyrobaculum aerophilum, Pyrococcus abyssi, Sulfolobus solfataricus, Sulfolobus tokodaii, Thermoplasma acidophilum, Thermoplasma volcanium*, or the like, or a eubacterium, such as *Escherichia coli, Thermus thermophilus, Bacillus stearothermphilus*, or the like, while the orthogonal O-RS can be derived from a non-eukaryotic organism (or a combination of organisms), e.g., an archaebacterium, such as *Methanococcus jannaschii, Methanobacterium thermoautotrophicum, Halobacterium* such as *Haloferax volcanii* and *Halobacterium* species NRC-1, *Archaeoglobus fulgidus, Pyrococcus furiosus, Pyrococcus horikoshii, Aeuropyrum pernix, Methanococcus maripaludis, Methanopyrus kandleri, Methanosarcina mazei, Pyrobaculum aerophilum, Pyrococcus abyssi, Sulfolobus solfataricus, Sulfolobus tokodaii, Thermoplasma acidophilum, Thermoplasma volcanium*, or the like, or a eubacterium, such as *Escherichia coli, Thermus thermophilus, Bacillus stearothermphilus*, or the like. In one embodiment, eukaryotic sources, e.g., plants, algae, protists, fungi, yeasts, animals (e.g., mammals, insects, arthropods, etc.), or the like, can also be used as sources of O-tRNAs and O-RSs.

The individual components of an O-tRNA/O-RS pair can be derived from the same organism or different organisms. In one embodiment, the O-tRNA/O-RS pair is from the same organism. Alternatively, the O-tRNA and the O-RS of the O-tRNA/O-RS pair are from different organisms.

The O-tRNA, O-RS or O-tRNA/O-RS pair can be selected or screened in vivo or in vitro and/or used in a cell, e.g., a non-eukaryotic cell or a eukaryotic cell, to produce a polypeptide with a brominated or iodinated amino acid or other unnatural amino acid of interest. A non-eukaryotic cell can be from any of a variety of sources, e.g., a eubacterium, such as *Escherichia coli, Thermus thermophilus, Bacillus stearothermphilus*, or the like, or an archaebacterium, such as *Methanococcus jannaschii, Methanobacterium thermoautotrophicum, Halobacterium* such as *Haloferax volcanii* and *Halobacterium* species NRC-1, *Archaeoglobus fulgidus, Pyrococcus furiosus, Pyrococcus horikoshii, Aeuropyrum pernix, Methanococcus maripaludis, Methanopyrus kandleri, Methanosarcina mazei, Pyrobaculum aerophilum, Pyrococcus abyssi, Sulfolobus solfataricus, Sulfolobus tokodaii, Thermoplasma acidophilum, Thermoplasma volcanium*, or the like. A eukaryotic cell can be from any of a variety of sources, e.g., a plant (e.g., complex plants such as monocots or dicots), an algae, a protist, a fungus, a yeast (e.g., *Saccharomyces cerevisiae*), an animal (e.g., a mammal, an insect, an arthropod, etc.), or the like. For example, suitable insect host cells include, but are not limited to, *Lepidopteran, Spodoptera frugiperda, Bombyx mori, Heliothis virescens, Heliothis zea, Mamestra brassicas, Estigmene acrea*, and *Trichoplusia ni* insect cells; exemplary insect cell lines include BT1-TN-5B1-4 (High Five), BTI-TN-MG1, Sf9, Sf21, TN-368, D.Mel-2, and Schneider S-2 cells, among many others. To express a protein incorporating a heavy atom-containing amino acid, such insect cells are optionally infected with a recombinant baculovirus vector encoding the protein and a selector codon. A variety of baculovirus expression systems are known in the art and/or are commercially available, e.g., BaculoDirect™ (Invitrogen, Carlsbad, Calif.) and BD BaculoGold™ Baculovirus Expression Vector System (BD Biosciences, San Jose, Calif.). Compositions of cells with translational components of the invention are also a feature of the invention.

See also, International Application No. PCT/US2004/011786, filed Apr. 16, 2004, for screening O-tRNA and/or O-RS in one species for use in another species.

Selector Codons

Selector codons of the invention expand the genetic codon framework of the protein biosynthetic machinery. For example, a selector codon includes, e.g., a unique three base codon, a nonsense codon, such as a stop codon, e.g., an amber codon (UAG), or an opal codon (UGA), an unnatural codon, at least a four base codon (e.g., AGGA), a rare codon, or the like. A number of selector codons can be introduced into a desired gene, e.g., one or more, two or more, more than three, etc. By using different selector codons, multiple orthogonal tRNA/synthetase pairs can be used that allow the simultaneous site-specific incorporation of multiple different unnatural amino acids, using these different selector codons. Similarly, more than one copy of a given selector codon can by introduced into a desired gene to allow the site-specific incorporation of a given unnatural amino acid at multiple sites (e.g., two or more, three or more, etc.).

In one embodiment, the methods involve the use of a selector codon that is a stop codon for the incorporation of a heavy atom-containing amino acid, e.g., in vivo in a cell. For example, an O-tRNA is produced that recognizes a stop selector codon and is aminoacylated by an O-RS with a heavy atom-containing amino acid. This O-tRNA is not recognized by the translation system's endogenous aminoacyl-tRNA synthetases. Conventional site-directed mutagenesis can be used to introduce the selector codon at the site of interest in a target polynucleotide encoding a polypeptide of interest. See also, e.g., Sayers, J. R., et al. (1988) "5', 3' Exonuclease in phosphorothioate-based oligonucleotide-directed mutagenesis" Nucleic Acids Res 791-802. When the O-RS, O-tRNA and the nucleic acid that encodes a polypeptide of interest are combined, e.g., in vivo, the heavy atom-containing amino acid is incorporated in response to the selector codon to give a polypeptide containing the heavy atom-containing amino acid at the specified position.

The incorporation of unnatural amino acids such as heavy atom-containing amino acids in vivo can be done without significant perturbation of the host cell. For example, in non-eukaryotic cells, such as *Escherichia coli*, because the suppression efficiency of a stop selector codon, e.g., the UAG codon, depends upon the competition between the O-tRNA, e.g., the amber suppressor tRNA, and release factor 1 (RF1) (which binds to the UAG codon and initiates release of the growing peptide from the ribosome), the suppression efficiency can be modulated by, e.g., either increasing the expression level of O-tRNA, e.g., the suppressor tRNA, or using an RF1 deficient strain. In eukaryotic cells, because the suppression efficiency for a UAG codon depends upon the competition between the O-tRNA, e.g., the amber suppressor tRNA, and a eukaryotic release factor (e.g., eRF) (which binds to a stop codon and initiates release of the growing peptide from the ribosome), the suppression efficiency can be modulated by, e.g., increasing the expression level of O-tRNA, e.g., the suppressor tRNA. In addition, additional compounds can also be present that modulate release factor action, e.g., reducing agents such as dithiothreitol (DTT).

Unnatural amino acids, including, e.g., heavy atom-containing amino acids, can also be encoded with rare codons. For example, when the arginine concentration in an in vitro protein synthesis reaction is reduced, the rare arginine codon, AGG, has proven to be efficient for insertion of Ala by a synthetic tRNA acylated with alanine. See, e.g., Ma et al., Biochemistry, 32:7939 (1993). In this case, the synthetic tRNA competes with the naturally occurring tRNA$_{Arg}$, which exists as a minor species in *Escherichia coli*. In addition, some organisms do not use all triplet codons. An unassigned codon AGA in *Micrococcus luteus* has been utilized for insertion of amino acids in an in vitro transcription/translation extract. See, e.g., Kowal and Oliver, Nucl. Acid. Res., 25:4685 (1997). Components of the invention can be generated to use these rare codons in vivo.

Selector codons can also comprise extended codons, e.g., four or more base codons, such as four, five, six or more base codons. Examples of four base codons include, e.g., AGGA, CUAG, UAGA, CCCU, and the like. Examples of five base codons include, e.g., AGGAC, CCCCU, CCCUC, CUAGA, CUACU, UAGGC, and the like. Methods of the invention can include using extended codons based on frameshift suppression. Four or more base codons can insert, e.g., one or multiple unnatural amino acids into the same protein. In other embodiments, the anticodon loops can decode, e.g., at least a four-base codon, at least a five-base codon, or at least a six-base codon or more. Since there are 256 possible four-base codons, multiple unnatural amino acids can be encoded in the same cell using a four or more base codon. See also, Anderson et al. (2002) "Exploring the Limits of Codon and Anticodon Size" Chemistry and Biology 9:237-244 and Magliery (2001) "Expanding the Genetic Code: Selection of Efficient Suppressors of Four-base Codons and Identification of "Shifty" Four-base Codons with a Library Approach in *Escherichia coli*" J. Mol. Biol. 307:755-769.

For example, four-base codons have been used to incorporate unnatural amino acids into proteins using in vitro biosynthetic methods. See, e.g., Ma et al. (1993) Biochemistry 32:7939, and Hohsaka et al. (1999) J. Am. Chem. Soc. 121: 34. CGGG and AGGU were used to simultaneously incorporate 2-naphthylalanine and an NBD derivative of lysine into streptavidin in vitro with two chemically acylated frameshift suppressor tRNAs. See, e.g., Hohsaka et al. (1999) J. Am. Chem. Soc. 121:12194. In an in vivo study, Moore et al. examined the ability of tRNA$^{Leu}$ derivatives with NCUA anti-codons to suppress UAGN codons (N can be U, A, G, or C), and found that the quadruplet UAGA can be decoded by a tRNA$^{Leu}$ with a UCUA anticodon with an efficiency of 13 to 26% with little decoding in the 0 or −1 frame. See Moore et al. (2000) J. Mol. Biol. 298:195. In one embodiment, extended codons based on rare codons or nonsense codons can be used in the invention, which can reduce missense readthrough and frameshift suppression at other unwanted sites.

For a given system, a selector codon can also include one of the natural three base codons, where the endogenous system does not use (or rarely uses) the natural base codon. For example, this includes a system that is lacking a tRNA that recognizes the natural three base codon, and/or a system where the three base codon is a rare codon.

Selector codons optionally include unnatural base pairs. These unnatural base pairs further expand the existing genetic alphabet. One extra base pair increases the number of triplet codons from 64 to 125. Properties of third base pairs include stable and selective base pairing, efficient enzymatic incorporation into DNA with high fidelity by a polymerase, and the efficient continued primer extension after synthesis of the nascent unnatural base pair. Descriptions of unnatural base pairs which can be adapted for methods and compositions include, e.g., Hirao, et al. (2002) "An unnatural base pair for incorporating amino acid analogues into protein" Nature Biotechnology, 20:177-182. See also Wu, Y., et al. (2002) J. Am. Chem. Soc. 124:14626-14630. Other relevant publications are listed below.

For in vivo usage, the unnatural nucleoside is membrane permeable and is phosphorylated to form the corresponding triphosphate. In addition, the increased genetic information is stable and not destroyed by cellular enzymes. Previous efforts by Benner and others took advantage of hydrogen bonding patterns that are different from those in canonical Watson-Crick pairs, the most noteworthy example of which is the iso-C:iso-G pair. See, e.g., Switzer et al. (1989) J. Am. Chem. Soc. 111:8322; Piccirilli et al. (1990) Nature 343:33; and Kool (2000) Curr. Opin. Chem. Biol. 4:602. These bases in general mispair to some degree with natural bases and cannot be enzymatically replicated. Kool and co-workers demonstrated that hydrophobic packing interactions between bases can replace hydrogen bonding to drive the formation of base pair. See Kool, (2000) Curr. Opin. Chem. Biol. 4:602; and Guckian and Kool (1998) Angew. Chem. Int. Ed. Engl. 36:2825. In an effort to develop an unnatural base pair satisfying all the above requirements, Schultz, Romesberg and co-workers have systematically synthesized and studied a series of unnatural hydrophobic bases. A PICS:PICS self-pair is found to be more stable than natural base pairs, and can be efficiently incorporated into DNA by Klenow fragment of Escherichia coli DNA polymerase I (KF). See, e.g., McMinn et al. (1999) J. Am. Chem. Soc. 121:11586; and Ogawa et al. (2000) J. Am. Chem. Soc. 122:3274. A 3MN:3MN self-pair can be synthesized by KF with efficiency and selectivity sufficient for biological function. See, e.g., Ogawa et al. (2000) J. Am. Chem. Soc. 122:8803. However, both bases act as a chain terminator for further replication. A mutant DNA polymerase has been recently evolved that can be used to replicate the PICS self pair. In addition, a 7AI self pair can be replicated. See, e.g., Tae et al. (2001) J. Am. Chem. Soc. 123:7439. A novel metallobase pair, Dipic:Py, has also been developed, which forms a stable pair upon binding Cu(II).

See Meggers et al. (2000) J. Am. Chem. Soc. 122:10714. Because extended codons and unnatural codons are intrinsically orthogonal to natural codons, the methods of the invention can take advantage of this property to generate orthogonal tRNAs for them.

A translational bypassing system can also be used to incorporate a heavy atom-containing amino acid or other unnatural amino acid into a desired polypeptide. In a translational bypassing system, a large sequence is inserted into a gene but is not translated into protein. The sequence contains a structure that serves as a cue to induce the ribosome to hop over the sequence and resume translation downstream of the insertion.

Unnatural Amino Acids

As used herein, an unnatural amino acid refers to any amino acid, modified amino acid, or amino acid analog other than selenocysteine and/or pyrrolysine and the following twenty genetically encoded alpha-amino acids: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine. The generic structure of an alpha-amino acid is illustrated by Formula I:

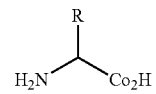

An unnatural amino acid is typically any structure having Formula I wherein the R group is any substituent other than one used in the twenty natural amino acids. See e.g., Biochemistry by L. Stryer, 3$^{rd}$ ed. 1988, Freeman and Company, New York, for structures of the twenty natural amino acids. Note that the unnatural amino acids of the invention can be naturally occurring compounds other than the twenty alpha-amino acids above (or, of course, can be artificially produced synthetic compounds).

Because the unnatural amino acids of the invention typically differ from the natural amino acids in side chain, the unnatural amino acids form amide bonds with other amino acids, e.g., natural or unnatural, in the same manner in which they are formed in naturally occurring proteins. However, the unnatural amino acids have side chain groups that distinguish them from the natural amino acids.

Figure 6:
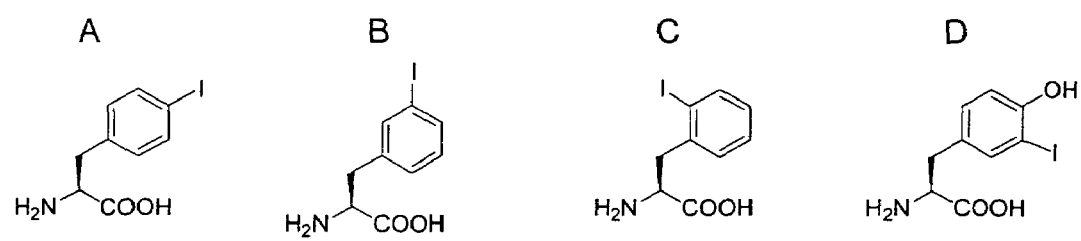
FIG. 6 provides examples of structures of heavy-atom containing amino acids that can be incorporated into proteins using an orthogonal tRNA/synthetase system e.g, in vivo for the purpose of protein structure determination. Panel A depicts p-iodo-L-phenylalanine (iodoPhe), Panel B L-3-iodophenylalanine, Panel C L-2-iodophenylalanine, and Panel D L-3-iodotyrosine.

Of particular interest in incorporating unnatural amino acids into proteins is to have the ability to incorporate a heavy atom-containing amino acid, typically, an amino acid in which R in Formula I comprises a heavy atom. Suitable heavy atoms include, but are not limited to, I, Br, U, Hg, Ag, Pt, Pb, Au, Pd, Ir, Os, Cd, Ba, Xe, Te, and Se. Preferred heavy atom-containing amino acids include brominated and iodinated amino acids, for example, p-iodo-L-phenylalanine (also known as iodoPhe or L-4-iodophenylalanine; FIG. 6 Panel A), L-3-iodophenylalanine (FIG. 6 Panel B), L-2-iodophenylalanine (FIG. 6 Panel C), L-3-iodotyrosine (FIG. 6 Panel D), L-2-iodotyrosine, p-bromo-L-phenylalanine (also known as bromoPhe or L-4-bromophenylalanine), L-3-bromophenylalanine, L-2-bromophenylalanine, L-3-bromotyrosine, and L-2-bromotyrosine. Other heavy atom-containing amino acids include Phe and Tyr substituted with a heavy atom other than I or Br, as well as other natural and unnatural amino acids substituted with any heavy atom.

In other unnatural amino acids, for example, R in Formula I optionally comprises an alkyl-, aryl-, acyl-, keto-, azido-, hydroxyl-, hydrazine, cyano-, halo-, hydrazide, alkenyl, alkynyl, ether, thiol, seleno-, sulfonyl-, borate, boronate, phospho, phosphono, phosphine, heterocyclic, enone, imine, aldehyde, ester, thioacid, hydroxylamine, amine, and the like, or any combination thereof. Other unnatural amino acids of interest include, but are not limited to, amino acids comprising a photoactivatable cross-linker, spin-labeled amino acids, fluorescent amino acids, metal binding amino acids, metal-containing amino acids, radioactive amino acids, amino acids with novel functional groups, amino acids that covalently or noncovalently interact with other molecules, photocaged and/or photoisomerizable amino acids, biotin or biotin-analog containing amino acids, keto containing amino acids, glycosylated amino acids, amino acids comprising polyethylene glycol or polyether, chemically cleavable or photocleavable amino acids, amino acids with an elongated side chain as compared to natural amino acids (e.g., polyethers or long chain hydrocarbons, e.g., greater than about 5, greater than about 10 carbons, etc.), carbon-linked sugar-containing amino acids, redox-active amino acids, amino thioacid containing amino acids, and amino acids containing one or more toxic moiety. In some embodiments, the unnatural amino acids have a photoactivatable cross-linker. In one embodiment, the unnatural amino acids have a saccharide moiety attached to the amino acid side chain and/or other carbohydrate modification.

In addition to unnatural amino acids that contain novel side chains, unnatural amino acids also optionally comprise modified backbone structures, e.g., as illustrated by the structures of Formula II and III:

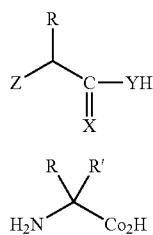

wherein Z typically comprises OH, $NH_2$, SH, NH—R', or S—R'; X and Y, which can be the same or different, typically comprise S or O, and R and R', which are optionally the same or different, are typically selected from the same list of constituents for the R group described above for the unnatural amino acids having Formula I as well as hydrogen. For example, unnatural amino acids of the invention optionally comprise substitutions in the amino or carboxyl group as illustrated by Formulas II and III. Unnatural amino acids of this type include, but are not limited to, α-hydroxy acids, α-thioacids α-aminothiocarboxylates, e.g., with side chains corresponding to the common twenty natural amino acids or unnatural side chains. In addition, substitutions at the α-carbon optionally include L, D, or α-α-disubstituted amino acids such as D-glutamate, D-alanine, D-methyl-O-tyrosine, aminobutyric acid, and the like. Other structural alternatives include cyclic amino acids, such as proline analogs as well as 3, 4, 6, 7, 8, and 9 membered ring proline analogs, β and γ amino acids such as substituted β-alanine and γ-amino butyric acid. Additional unnatural amino acid structures of the invention include homo-beta-type structures, e.g., where there is, e.g., a methylene or amino group sandwiched adjacent to the alpha carbon, e.g., isomers of homo-beta-tyrosine, alpha-hydrazino-tyrosine. See, e.g.,

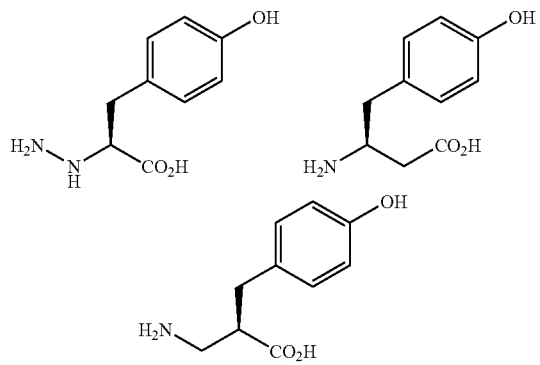

Many unnatural amino acids are based on natural amino acids, such as tyrosine, glutamine, phenylalanine, and the like. For example, tyrosine analogs include para-substituted tyrosines, ortho-substituted tyrosines, and meta substituted tyrosines, wherein the substituted tyrosine comprises an acetyl group, a benzoyl group, an amino group, a hydrazine, an hydroxyamine, a thiol group, a carboxy group, an isopropyl group, a methyl group, a $C_6$-$C_{20}$ straight chain or branched hydrocarbon, a saturated or unsaturated hydrocarbon, an O-methyl group, a polyether group, a nitro group, or the like. In addition, multiply substituted aryl rings are also contemplated. Glutamine analogs of the invention include, but are not limited to, α-hydroxy derivatives, γ-substituted derivatives, cyclic derivatives, and amide substituted glutamine derivatives. Example phenylalanine analogs include, but are not limited to, para-substituted phenylalanines, ortho-substituted phenyalanines, and meta-substituted phenylalanines, wherein the substituent comprises a hydroxy group, a methoxy group, a methyl group, an allyl group, an aldehyde or keto group, or the like. Specific examples of unnatural amino acids include, but are not limited to, homoglutamine, a 3,4-dihydroxy-L-phenylalanine, a p-acetyl-L-phenylalanine, a p-propargyloxyphenylalanine, O-methyl-L-tyrosine, an L-3-(2-naphthyl)alanine, a 3-methyl-phenylalanine, an O-4-allyl-L-tyrosine, a 4-propyl-L-tyrosine, a tri-O-acetyl-GlcNAcβ-serine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-amino-L-phenylalanine, and an isopropyl-L-phenylalanine, and the like.

Chemical Synthesis of Unnatural Amino Acids

Many of the unnatural amino acids provided above are commercially available, e.g., from Sigma (USA) or Aldrich (Milwaukee, Wis., USA). For example, brominated and iodinated phenylalanines and tyrosines are available from Sigma, Synthetech, Inc. (on the world wide web at synthetech.com) and Advanced Asymmetrics, Inc. (advancedasymmetrics.com). Those that are not commercially available are optionally synthesized as provided in various publications or using standard methods known to those of skill in the art. For organic synthesis techniques, see, e.g., *Organic Chemistry* by Fessendon and Fessendon, (1982, Second Edition, Willard Grant Press, Boston Mass.); *Advanced Organic Chemistry* by March (Third Edition, 1985, Wiley and Sons, New York); and *Advanced Organic Chemistry* by Carey and Sundberg (Third Edition, Parts A and B, 1990, Plenum Press, New York). Additional publications describing the synthesis of unnatural amino acids include, e.g., WO 2002/085923 entitled "In vivo incorporation of Unnatural Amino Acids;" Matsoukas et al.

(1995) J. Med. Chem. 38:4660-4669; King, F. E. and Kidd, D. A. A. (1949) "A New Synthesis of Glutamine and of γ-Dipeptides of Glutamic Acid from Phthylated Intermediates" J. Chem. Soc. 3315-3319; Friedman, O. M. and Chatterrji, R. (1959) "Synthesis of Derivatives of Glutamine as Model Substrates for Anti-Tumor Agents" J. Am. Chem. Soc. 81:3750-3752; Craig, J. C. et al. (1988) "Absolute Configuration of the Enantiomers of 7-Chloro-4[[4-(diethylamino)-1-methylbutyl]amino]quinoline (Chloroquine)" J. Org. Chem. 53:1167-1170; Azoulay, M., Vilmont, M. and Frappier, F. (1991) "Glutamine analogues as Potential Antimalarials" Eur. J. Med. Chem. 26:201-5; Koskinen, A. M. P. and Rapoport, H. (1989) "Synthesis of 4-Substituted Prolines as Conformationally Constrained Amino Acid Analogues" J. Org. Chem. 54:1859-1866; Christie, B. D. and Rapoport, H. (1985) "Synthesis of Optically Pure Pipecolates from L-Asparagine. Application to the Total Synthesis of (+)-Apovincamine through Amino Acid Decarbonylation and Iminium Ion Cyclization" J. Org. Chem. 1989:1859-1866; Barton et al., (1987) "Synthesis of Novel a-Amino-Acids and Derivatives Using Radical Chemistry: Synthesis of L- and D-a-Amino-Adipic Acids, L-a-aminopimelic Acid and Appropriate Unsaturated Derivatives" Tetrahedron Lett. 43:4297-4308; and, Subasinghe et al. (1992) "Quisqualic acid analogues: synthesis of beta-heterocyclic 2-aminopropanoic acid derivatives and their activity at a novel quisqualate-sensitized site" J. Med. Chem. 35:4602-7. See also International Aplication No. PCT/US03/41346, entitled "Protein Arrays," filed on Dec. 22, 2003.

Cellular Uptake of Unnatural Amino Acids

Unnatural amino acid uptake by a cell is one issue that is typically considered when designing and selecting unnatural amino acids, e.g., for incorporation into a protein. For example, the high charge density of α-amino acids suggests that these compounds are unlikely to be cell permeable. Natural amino acids are taken up into the cell via a collection of protein-based transport systems often displaying varying degrees of amino acid specificity. A rapid screen can be done which assesses which unnatural amino acids, if any, are taken up by cells. See, e.g., toxicity assays in, e.g., International application No. PCT/US03/41346, entitled "Protein Arrays," filed on Dec. 22, 2003; and Liu, D. R. and Schultz, P. G. (1999) "Progress toward the evolution of an organism with an expanded genetic code" PNAS United States 96:4780-4785. Although uptake is easily analyzed with various assays, an alternative to designing unnatural amino acids that are amenable to cellular uptake pathways is to provide biosynthetic pathways to create amino acids in vivo.

Biosynthesis of Unnatural Amino Acids

Many biosynthetic pathways already exist in cells for the production of amino acids and other compounds. While a biosynthetic method for a particular unnatural amino acid may not exist in nature, e.g., in a cell, the invention provides such methods. For example, biosynthetic pathways for unnatural amino acids are optionally generated in host cell by adding new enzymes or modifying existing host cell pathways. Additional new enzymes are optionally naturally occurring enzymes or artificially evolved enzymes. For example, the biosynthesis of p-aminophenylalanine (as presented in an example in WO 2002/085923, supra) relies on the addition of a combination of known enzymes from other organisms. The genes for these enzymes can be introduced into a cell by transforming the cell with a plasmid comprising the genes. The genes, when expressed in the cell, provide an enzymatic pathway to synthesize the desired compound. Examples of the types of enzymes that are optionally added are provided in the examples below. Additional enzyme sequences are found, e.g., in Genbank. Artificially evolved enzymes are also optionally added into a cell in the same manner. In this manner, the cellular machinery and resources of a cell are manipulated to produce unnatural amino acids.

Indeed, any of a variety of methods can be used for producing novel enzymes for use in biosynthetic pathways, or for evolution of existing pathways, for the production of unnatural amino acids, in vitro or in vivo. Many available methods of evolving enzymes and other biosynthetic pathway components can be applied to the present invention to produce unnatural amino acids (or, indeed, to evolve synthetases to have new substrate specificities or other activities of interest). For example, DNA shuffling is optionally used to develop novel enzymes and/or pathways of such enzymes for the production of unnatural amino acids (or production of new synthetases), in vitro or in vivo. See, e.g., Stemmer (1994) "Rapid evolution of a protein in vitro by DNA shuffling" Nature 370(4):389-391; and, Stemmer, (1994) "DNA shuffling by random fragmentation and reassembly: In vitro recombination for molecular evolution" Proc. Natl. Acad. Sci. USA., 91:10747-10751. A related approach shuffles families of related (e.g., homologous) genes to quickly evolve enzymes with desired characteristics. An example of such "family gene shuffling" methods is found in Crameri et al. (1998) "DNA shuffling of a family of genes from diverse species accelerates directed evolution" Nature, 391(6664): 288-291. New enzymes (whether biosynthetic pathway components or synthetases) can also be generated using a DNA recombination procedure known as "incremental truncation for the creation of hybrid enzymes" ("ITCHY"), e.g., as described in Ostermeier et al. (1999) "A combinatorial approach to hybrid enzymes independent of DNA homology" Nature Biotech 17:1205. This approach can also be used to generate a library of enzyme or other pathway variants which can serve as substrates for one or more in vitro or in vivo recombination methods. See, also, Ostermeier et al. (1999) "Combinatorial Protein Engineering by Incremental Truncation" Proc. Natl. Acad. Sci. USA 96: 3562-67, and Ostermeier et al. (1999),"Incremental Truncation as a Strategy in the Engineering of Novel Biocatalysts" Biological and Medicinal Chemistry 7:2139-44. Another approach uses exponential ensemble mutagenesis to produce libraries of enzyme or other pathway variants that are, e.g., selected for an ability to catalyze a biosynthetic reaction relevant to producing an unnatural amino acid (or a new synthetase). In this approach, small groups of residues in a sequence of interest are randomized in parallel to identify, at each altered position, amino acids which lead to functional proteins. Examples of such procedures, which can be adapted to the present invention to produce new enzymes for the production of unnatural amino acids (or new synthetases) are found in Delegrave and Youvan (1993) Biotechnology Research 11:1548-1552. In yet another approach, random or semi-random mutagenesis using doped or degenerate oligonucleotides for enzyme and/or pathway component engineering can be used, e.g., by using the general mutagenesis methods of e.g., Arkin and Youvan (1992) "Optimizing nucleotide mixtures to encode specific subsets of amino acids for semi-random mutagenesis" Biotechnology 10:297-300; or Reidhaar-Olson et al. (1991) "Random mutagenesis of protein sequences using oligonucleotide cassettes" Methods Enzymol. 208:564-86. Yet another approach, often termed a "non-stochastic" mutagenesis, which uses polynucleotide reassembly and site-saturation mutagenesis can be used to produce enzymes and/or pathway components, which can then be screened for an ability to perform one or more synthetase or biosynthetic pathway function (e.g., for the production of unnatural amino acids in vivo). See, e.g., Short "Non-Stochastic Generation of Genetic Vaccines and Enzymes" WO 00/46344.

An alternative to such mutational methods involves recombining entire genomes of organisms and selecting resulting progeny for particular pathway functions (often referred to as "whole genome shuffling"). This approach can be applied to the present invention, e.g., by genomic recombination and selection of an organism (e.g., an E. coli or other cell) for an ability to produce an unnatural amino acid (or intermediate thereof). For example, methods taught in the following publications can be applied to pathway design for the evolution of existing and/or new pathways in cells to produce unnatural amino acids in vivo: Patnaik et al. (2002) "Genome shuffling of lactobacillus for improved acid tolerance" Nature Biotechnology 20(7):707-712; and Zhang et al. (2002) "Genome shuffling leads to rapid phenotypic improvement in bacteria" Nature 415:644-646.

Other techniques for organism and metabolic pathway engineering, e.g., for the production of desired compounds are also available and can also be applied to the production of unnatural amino acids. Examples of publications teaching useful pathway engineering approaches include: Nakamura and White (2003) "Metabolic engineering for the microbial production of 1,3 propanediol" Curr. Opin. Biotechnol. 14(5):454-9; Berry et al. (2002) "Application of Metabolic Engineering to improve both the production and use of Biotech Indigo" J. Industrial Microbiology and Biotechnology 28:127-133; Banta et al. (2002) "Optimizing an artificial metabolic pathway: Engineering the cofactor specificity of Corynebacterium 2,5-diketo-D-gluconic acid reductase for use in vitamin C biosynthesis" Biochemistry 41(20):6226-36; Selivonova et al. (2001) "Rapid Evolution of Novel Traits in Microorganisms" Applied and Environmental Microbiology 67:3645, and many others.

Regardless of the method used, typically, the unnatural amino acid produced with an engineered biosynthetic pathway of the invention is produced in a concentration sufficient for efficient protein biosynthesis, e.g., a natural cellular amount, but not to such a degree as to significantly affect the concentration of other cellular amino acids or to exhaust cellular resources. Typical concentrations produced in vivo in this manner are about 10 mM to about 0.05 mM. Once a cell is engineered to produce enzymes desired for a specific pathway and an unnatural amino acid is generated, in vivo selections are optionally used to further optimize the production of the unnatural amino acid for both ribosomal protein synthesis and cell growth.

Orthogonal Components for Incorporating Heavy Atom-Containing Amino Acids

The invention provides compositions for incorporating a heavy atom-containing amino acid (e.g., a brominated or iodinated amino acid, e.g., iodoPhe or bromoPhe) into a growing polypeptide chain in response to a selector codon, e.g., a stop codon, a nonsense codon, a four or more base codon, etc., e.g., in vivo or in vitro. For example, the invention provides orthogonal-tRNAs (O-tRNAs), orthogonal aminoacyl-tRNA synthetases (O-RSs), and pairs thereof. These pairs can be used to incorporate heavy atom-containing amino acids into growing polypeptide chains.

A composition of the invention includes an orthogonal aminoacyl-tRNA synthetase (O-RS), where the O-RS preferentially aminoacylates an O-tRNA with a brominated or iodinated amino acid. In certain embodiments, the O-RS comprises an amino acid sequence comprising SEQ ID NO:3 or 4, or a conservative variation thereof. In some embodiments, the O-RS comprises an amino acid sequence encoded by a polynucleotide sequence comprising SEQ ID NO:1 or 2, or a complement thereof. In certain embodiments of the invention, the O-RS preferentially aminoacylates the O-tRNA with the brominated or iodinated amino acid with an efficiency of at least 50% (e.g., at least 60%, at least 75%, at least 80%, or at least 90% or more) of the efficiency with which a polypeptide comprising an amino acid sequence of SEQ ID NO:3 or 4 preferentially aminoacylates the O-tRNA with the brominated or iodinated amino acid. O-RS of the invention can specifically exclude O-RS comprising an amino acid sequence of any of SEQ ID NOs:6-9. In certain embodiments, the O-RS has an amino acid sequence that is at least 90% identical to that of a naturally occurring tyrosyl aminoacyl-tRNA synthetase (TyrRS) and comprises two or more (e.g., three or more, four or more, or five) amino acids selected from the group consisting of: Leu at a position corresponding to Tyr32 of M. jannaschii TyrRS, Ser or Glu at a position corresponding to Glu107 of M. jannaschii TyrRS, Pro at a position corresponding to Asp158 of M. jannaschii TyrRS, Leu or Arg at a position corresponding to Ile159 of M. jannaschii TyrRS, and Glu or Arg at a position corresponding to Leu162 of M. jannaschii TyrRS.

A composition that includes an O-RS can optionally further include an orthogonal tRNA (O-tRNA), where the O-tRNA recognizes a selector codon. Typically, an O-tRNA of the invention includes at least about, e.g., a 45%, a 50%, a 60%, a 75%, a 80%, or a 90% or more suppression efficiency in the presence of a cognate synthetase in response to a selector codon as compared to the O-tRNA comprising or encoded by a polynucleotide sequence as set forth in the sequence listing and examples herein. In one embodiment, the suppression efficiency of the O-RS and the O-tRNA together is, e.g., 5 fold, 10 fold, 15 fold, 20 fold, 25 fold or more greater than the suppression efficiency of the O-tRNA lacking the O-RS.

A composition that includes an O-RS can optionally include a cell (e.g., a non-eukaryotic cell, such as an E. coli cell and the like, or a eukaryotic cell), and/or a translation system.

A cell (e.g., a non-eukaryotic cell, or a eukaryotic cell) comprising a translation system is also provided by the invention, where the translation system includes an orthogonal tRNA (O-tRNA), an orthogonal aminoacyl-tRNA synthetase (O-RS), and a brominated or iodinated amino acid. The O-tRNA recognizes a first selector codon, and the O-RS preferentially aminoacylates the O-tRNA with the brominated or iodinated amino acid. In one embodiment, the O-tRNA comprises or is encoded by a polynucleotide sequence as set forth in SEQ ID NO:5, or a conservative variant thereof. In one embodiment, the O-RS comprises an amino acid sequence as set forth in any one of SEQ ID NOs:3-4, or a conservative variation thereof. In some embodiments, the O-RS comprises an amino acid sequence encoded by a polynucleotide sequence comprising SEQ ID NO:1 or 2, or a complement thereof. In certain embodiments of the invention, the O-RS preferentially aminoacylates the O-tRNA with the brominated or iodinated amino acid with an efficiency of at least 50% (e.g., at least 60%, at least 75%, at least 80%, or at least 90% or more) of the efficiency of a polypeptide comprising an amino acid sequence of SEQ ID NO:3 or 4. O-RS of the invention can specifically exclude O-RS comprising an amino acid sequence of any of SEQ ID NOs:6-9. In certain embodiments, the O-RS has an amino acid sequence that is at least 90% identical to that of a naturally occurring tyrosyl aminoacyl-tRNA synthetase (TyrRS) and comprises two or more (e.g., three or more, four or more, or five) amino acids selected from the group consisting of: Leu at a position corresponding to Tyr32 of M. jannaschii TyrRS, Ser or Glu at a position corresponding to Glu107 of *M. jannaschii* TyrRS, Pro at a position corresponding to Asp158 of *M. jannaschii* TyrRS, Leu or Arg at a position corresponding to Ile159 of *M. jannaschii* TyrRS, and Glu or Arg at a position corresponding to Leu162 of *M. jannaschii* TyrRS.

Optionally, a cell of the invention includes a nucleic acid that comprises a polynucleotide that encodes a polypeptide of interest, where the polynucleotide comprises a selector codon that is recognized by the O-tRNA. A cell of the invention can optionally further comprise an additional different O-tRNA/O-RS pair and a second unnatural amino acid, e.g., where this O-tRNA recognizes a second selector codon and this O-RS preferentially aminoacylates the O-tRNA with the second unnatural amino acid amino acid.

In certain embodiments, a cell of the invention (e.g., an *E. coli* cell) includes the orthogonal aminoacyl-tRNA synthetase (O-RS), an orthogonal-tRNA (O-tRNA), and a brominated or iodinated amino acid. The orthogonal tRNA recognizes a selector codon, and the orthogonal aminoacyl-tRNA synthetase preferentially aminoacylates the orthogonal tRNA with the brominated or iodinated amino acid. The O-RS and O-tRNA are each typically encoded by one or more nucleic acids in the cell. Optionally, the cell also includes a nucleic acid that encodes a polypeptide of interest, where the polynucleotide comprises the selector codon that is recognized by the O-tRNA. The cell can also include the protein encoded by the target nucleic acid, which protein comprises the brominated or iodinated amino acid.

In certain embodiments of the invention, an O-tRNA of the invention comprises or is encoded by a polynucleotide sequence as set forth in the sequence listing or examples herein, or a conservative variant thereof. In certain embodiments of the invention, an O-RS comprises an amino acid sequence as set forth in the sequence listing, or a conservative variation thereof. In one embodiment, the O-RS or a portion thereof is encoded by a polynucleotide sequence encoding an amino acid sequence as set forth in the sequence listing or examples herein, or a complementary polynucleotide sequence thereof.

The O-tRNA and/or the O-RS of the invention can be derived from any of a variety of organisms (e.g., eukaryotic and/or non-eukaryotic organisms).

Polynucleotides are also a feature of the invention. A nucleic acid of the invention includes a polynucleotide sequence of SEQ ID NO: 1 or 2, or a complementary polynucleotide sequence thereof. A polynucleotide of the invention also includes an artificial (e.g., man-made, and not naturally occurring) polynucleotide comprising a polynucleotide sequence encoding a polypeptide as set forth in the sequence listing herein, and/or is complementary to that polynucleotide sequence. A polynucleotide of the invention can also include a nucleic acid that hybridizes to a polynucleotide described above, under highly stringent conditions, over substantially the entire length of the nucleic acid. Artificial polynucleotides that are, e.g., at least 80%, at least 90%, at least 95%, at least 98% or more identical to any of the above and/or a polynucleotide comprising a conservative variation of any the above are also included in polynucleotides of the invention.

Vectors comprising a polynucleotide of the invention are also a feature of the invention. For example, a vector of the invention can include a plasmid, a cosmid, a phage, a virus, an expression vector, and/or the like. A cell comprising a vector of the invention is also a feature of the invention.

Methods for identifying an orthogonal-aminoacyl-tRNA synthetase that charges a heavy atom-containing amino acid (e.g., a brominated or iodinated amino acid) onto an O-tRNA are also provided. For example, methods include subjecting to selection a population of cells of a first species, where the cells each comprise: 1) a member of a plurality of aminoacyl-tRNA synthetases (RSs), (e.g., the plurality of RSs can include mutant RSs, RSs derived from a species other than a first species or both mutant RSs and RSs derived from a species other than a first species); 2) the orthogonal-tRNA (O-tRNA) (e.g., from one or more species); and 3) a polynucleotide that encodes a positive selection marker and comprises at least one selector codon, or a polynucleotide that encodes a negative selection marker and comprises at least one selector codon. The heavy atom-containing amino acid (e.g., the brominated or iodinated amino acid) is typically supplied during each round of positive selection and not provided during each round of negative selection.

Cells (e.g., a host cell) are positively selected or screened for those that show an enhancement in suppression efficiency compared to cells lacking or having a reduced amount of the member of the plurality of RSs. These selected/screened cells comprise an active RS that aminoacylates the O-tRNA. In addition, cells are negatively selected or screened, such that the selected/screened cells comprise an RS that does not aminoacylate the O-tRNA with an endogenous amino acid. An orthogonal aminoacyl-tRNA synthetase identified by the method is also a feature of the invention.

Nucleic Acid and Polypeptide Sequence and Variants

As described above and below, the invention provides for nucleic acid polynucleotide sequences, e.g., O-tRNAs and O-RSs, and polypeptide amino acid sequences, e.g., O-RSs, and, e.g., compositions, kits, systems, and methods comprising said sequences. Examples of said sequences, e.g., O-tRNAs and O-RSs, are disclosed herein (see the sequence listing and examples herein). However, one of skill in the art will appreciate that the invention is not limited to those exact sequences, e.g., as in the Examples and listing. One of skill will appreciate that the invention also provides, e.g., many related and unrelated sequences with the functions described herein, e.g., encoding an appropriate O-tRNA or an O-RS.

The invention provides polypeptides (O-RSs) and polynucleotides, e.g., O-tRNA, polynucleotides that encode O-RSs or portions thereof, oligonucleotides used to isolate aminoacyl-tRNA synthetase clones, etc. Polynucleotides of the invention include those that encode proteins or polypeptides of interest of the invention with one or more selector codon. In addition, polynucleotides of the invention include, e.g., a polynucleotide comprising a nucleotide sequence as set forth in the sequence listing and a polynucleotide that is complementary to or that encodes a polynucleotide sequence thereof. A polynucleotide of the invention also includes a polynucleotide that encodes a polypeptide of the invention. Similarly, an artificial nucleic acid that hybridizes to a polynucleotide indicated above under highly stringent conditions over substantially the entire length of the nucleic acid (and is other than a naturally polynucleotide) is a polynucleotide of the invention. An artificial polynucleotide is a polynucleotide that is man made and is not naturally occurring.

A polynucleotide of the invention also includes an artificial polynucleotide that is, e.g., at least 75%, at least 80%, at least 90%, at least 95%, at least 98% or more identical to that of a naturally occurring tRNA (but is other than a naturally occurring tRNA) or any tRNA or coding nucleic acid thereof in a listing or example herein. A polynucleotide also includes an artificial polynucleotide that is, e.g., at least 75%, at least 80%, at least 90%, at least 95%, at least 98% or more identical to that of a naturally occurring tRNA.

In certain embodiments, a vector (e.g., a plasmid, a cosmid, a phage, a virus, etc.) comprises a polynucleotide of the invention. In one embodiment, the vector is an expression vector. In certain embodiments, the expression vector includes a promoter operably linked to one or more of the polynucleotides of the invention. In some embodiments, a cell comprises a vector that includes a polynucleotide of the invention.

One of skill will also appreciate that many variants of the disclosed sequences are included in the invention. For example, conservative variations of the disclosed sequences that yield a functionally similar sequence are included in the invention. Unique subsequences of the sequences disclosed herein, as determined by, e.g., standard sequence comparison techniques, are also included in the invention.

Conservative Variations

Owing to the degeneracy of the genetic code, "silent substitutions" (i.e., substitutions in a nucleic acid sequence which do not result in an alteration in an encoded polypeptide) are an implied feature of every nucleic acid sequence which encodes an amino acid. Similarly, "conservative amino acid substitutions," in which one or a few amino acids in an amino acid sequence are substituted with different amino acids with highly similar properties, are also readily identified as being highly similar to a disclosed construct. Such conservative variations (or conservative variants) of each disclosed sequence are a feature of the present invention.

"Conservative variants" or "conservative variations" of a particular nucleic acid sequence refers to those nucleic acids which encode identical or essentially identical amino acid sequences, or, where the nucleic acid does not encode an amino acid sequence, to essentially identical sequences. One of skill will recognize that individual substitutions, deletions or additions which alter, add or delete a single amino acid or a small percentage of amino acids (typically less than 5%, more typically less than 4%, 2% or 1%) in an encoded sequence are "conservatively modified variations" where the alterations result in the deletion of an amino acid, addition of an amino acid, or substitution of an amino acid with a chemically similar amino acid. Thus, "conservative variants" or "conservative variations" of a listed polypeptide sequence of the present invention include substitutions of a small percentage, typically less than 5%, more typically less than 2% or 1%, of the amino acids of the polypeptide sequence with an amino acid of the same conservative substitution group. Finally, the addition of sequences which do not alter the encoded activity of a nucleic acid molecule, such as the addition of a non-functional sequence, is a conservative variation of the basic nucleic acid.

Conservative substitution tables providing functionally similar amino acids are well known in the art, where one amino acid residue is substituted for another amino acid residue having similar chemical properties (e.g., aromatic side chains or positively charged side chains), and therefore does not substantially change the functional properties of the polypeptide molecule. The following sets forth example groups that contain natural amino acids of like chemical properties, where substitution within a group is a "conservative substitution".

| Nonpolar and/or Aliphatic Side Chains | Polar, Uncharged Side Chains | Aromatic Side Chains | Positively Charged Side Chains | Negatively Charged Side Chains |
|---|---|---|---|---|
| Glycine | Serine | Phenylalanine | Lysine | Aspartate |
| Alanine | Threonine | Tyrosine | Arginine | Glutamate |
| Valine | Cysteine | Tryptophan | Histidine | |
| Leucine | Methionine | | | |
| Isoleucine | Asparagine | | | |
| Proline | Glutamine | | | |

Nucleic Acid Hybridization

Comparative hybridization can be used to identify nucleic acids of the invention, such as those in the sequence listing herein, including conservative variations of nucleic acids of the invention, and this comparative hybridization method is a one method of distinguishing nucleic acids of the invention from unrelated nucleic acids. In addition, target nucleic acids which hybridize to a nucleic acid represented by those of the sequence listing under high, ultra-high and ultra-ultra high stringency conditions are a feature of the invention. Examples of such nucleic acids include those with one or a few silent or conservative nucleic acid substitutions as compared to a given nucleic acid sequence.

A test nucleic acid is said to specifically hybridize to a probe nucleic acid when it hybridizes at least ½ as well to the probe as to the perfectly matched complementary target, i.e., with a signal to noise ratio at least ½ as high as hybridization of the probe to the target under conditions in which the perfectly matched probe binds to the perfectly matched complementary target with a signal to noise ratio that is at least about 5×-10× as high as that observed for hybridization to any of the unmatched target nucleic acids.

Nucleic acids "hybridize" when they associate, typically in solution. Nucleic acids hybridize due to a variety of well characterized physico-chemical forces, such as hydrogen bonding, solvent exclusion, base stacking, and the like. An extensive guide to the hybridization of nucleic acids is found in Tijssen (1993) *Laboratory Techniques in Biochemistry and Molecular Biology—Hybridization with Nucleic Acid Probes* part I chapter 2, "Overview of principles of hybridization and the strategy of nucleic acid probe assays," (Elsevier, New York), as well as in Ausubel, infra. Hames and Higgins (1995) *Gene Probes* 1 IRL Press at Oxford University Press, Oxford, England, (Hames and Higgins 1) and Hames and Higgins (1995) *Gene Probes* 2 IRL Press at Oxford University Press, Oxford, England (Hames and Higgins 2) provide details on the synthesis, labeling, detection and quantification of DNA and RNA, including oligonucleotides.

An example of stringent hybridization conditions for hybridization of complementary nucleic acids which have more than 100 complementary residues on a filter in a Southern or northern blot is 50% formalin with 1 mg of heparin at 42° C., with the hybridization being carried out overnight. An example of stringent wash conditions is a 0.2×SSC wash at 65° C. for 15 minutes (see, Sambrook, infra for a description of SSC buffer). Often the high stringency wash is preceded by a low stringency wash to remove background probe signal. An example low stringency wash is 2×SSC at 40° C. for 15 minutes. In general, a signal to noise ratio of 5× (or higher) than that observed for an unrelated probe in the particular hybridization assay indicates detection of a specific hybridization.

"Stringent hybridization wash conditions" in the context of nucleic acid hybridization experiments such as Southern and northern hybridizations are sequence dependent, and are different under different environmental parameters. An extensive guide to the hybridization of nucleic acids is found in Tijssen (1993), supra and in Hames and Higgins, 1 and 2. Stringent hybridization and wash conditions can easily be determined empirically for any test nucleic acid. For example, in determining stringent hybridization and wash conditions, the hybridization and wash conditions are gradually increased (e.g., by increasing temperature, decreasing salt concentration, increasing detergent concentration and/or increasing the concentration of organic solvents such as formalin in the hybridization or wash) until a selected set of criteria are met. For example, in highly stringent hybridization and wash conditions, the hybridization and wash conditions are gradually increased until a probe binds to a perfectly matched complementary target with a signal to noise ratio that is at least 5× as high as that observed for hybridization of the probe to an unmatched target.

"Very stringent" conditions are selected to be equal to the thermal melting point ($T_m$) for a particular probe. The $T_m$ is the temperature (under defined ionic strength and pH) at which 50% of the test sequence hybridizes to a perfectly matched probe. For the purposes of the present invention, generally, "highly stringent" hybridization and wash conditions are selected to be about 5° C. lower than the $T_m$ for the specific sequence at a defined ionic strength and pH.

"Ultra high-stringency" hybridization and wash conditions are those in which the stringency of hybridization and wash conditions are increased until the signal to noise ratio for binding of the probe to the perfectly matched complementary target nucleic acid is at least 10× as high as that observed for hybridization to any of the unmatched target nucleic acids. A target nucleic acid which hybridizes to a probe under such conditions, with a signal to noise ratio of at least ½ that of the perfectly matched complementary target nucleic acid is said to bind to the probe under ultra-high stringency conditions.

Similarly, even higher levels of stringency can be determined by gradually increasing the hybridization and/or wash conditions of the relevant hybridization assay. For example, those in which the stringency of hybridization and wash conditions are increased until the signal to noise ratio for binding of the probe to the perfectly matched complementary target nucleic acid is at least 10×, 20×, 50×, 100×, or 500× or more as high as that observed for hybridization to any of the unmatched target nucleic acids. A target nucleic acid which hybridizes to a probe under such conditions, with a signal to noise ratio of at least ½ that of the perfectly matched complementary target nucleic acid is said to bind to the probe under ultra-ultra-high stringency conditions.

Nucleic acids which do not hybridize to each other under stringent conditions are still substantially identical if the polypeptides which they encode are substantially identical. This occurs, e.g., when a copy of a nucleic acid is created using the maximum codon degeneracy permitted by the genetic code.

Unique Subsequences

In one aspect, the invention provides a nucleic acid that comprises a unique subsequence in a nucleic acid selected from the sequences of the O-tRNAs and O-RSs disclosed herein. The unique subsequence is unique as compared to a nucleic acid corresponding to any previously known tRNA or RS nucleic acid sequence. Alignment can be performed using, e.g., BLAST set to default parameters. Any unique subsequence is useful, e.g., as a probe to identify the nucleic acids of the invention.

Similarly, the invention includes a polypeptide which comprises a unique subsequence in a polypeptide selected from the sequences of O-RSs disclosed herein. Here, the unique subsequence is unique as compared to a polypeptide corresponding to any previously known RS sequence.

The invention also provides target nucleic acids which hybridize under stringent conditions to a unique coding oligonucleotide which encodes a unique subsequence in a polypeptide selected from the sequences of O-RSs, wherein the unique subsequence is unique as compared to a polypeptide corresponding to any of the control polypeptides (e.g., parental sequences from which synthetases of the invention were derived, e.g., by mutation). Unique sequences are determined as noted above.

Sequence Comparison, Identity, and Homology

The terms "identical" or percent "identity," in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the sequence comparison algorithms described below (or other algorithms available to persons of skill) or by visual inspection.

The phrase "substantially identical," in the context of two nucleic acids or polypeptides (e.g., DNAs encoding an O-tRNA or O-RS, or the amino acid sequence of an O-RS) refers to two or more sequences or subsequences that have at least about 60%, about 80%, about 90-95%, about 98%, or about 99% or more nucleotide or amino acid residue identity, when compared and aligned for maximum correspondence, as measured using a sequence comparison algorithm or by visual inspection. Such "substantially identical" sequences are typically considered to be "homologous," without reference to actual ancestry. Preferably, the "substantial identity" exists over a region of the sequences that is at least about 50 residues in length, more preferably over a region of at least about 100 residues, and most preferably, the sequences are substantially identical over at least about 150 residues, or over the full length of the two sequences to be compared.

Proteins and/or protein sequences are "homologous" when they are derived, naturally or artificially, from a common ancestral protein or protein sequence. Similarly, nucleic acids and/or nucleic acid sequences are homologous when they are derived, naturally or artificially, from a common ancestral nucleic acid or nucleic acid sequence. For example, any naturally occurring nucleic acid can be modified by any available mutagenesis method to include one or more selector codon. When expressed, this mutagenized nucleic acid encodes a polypeptide comprising one or more unnatural amino acid, e.g., one or more iodinated or brominated amino acid. The mutation process can, of course, additionally alter one or more standard codon, thereby changing one or more standard amino acid in the resulting mutant protein as well. Homology is generally inferred from sequence similarity between two or more nucleic acids or proteins (or sequences thereof). The precise percentage of similarity between sequences that is useful in establishing homology varies with the nucleic acid and protein at issue, but as little as 25% sequence similarity is routinely used to establish homology. Higher levels of sequence similarity, e.g., 30%, 40%, 50%, 60%, 70%, 80%, 90%, 95%, or 99% or more, can also be used to establish homology. Methods for determining sequence similarity percentages (e.g., BLASTP and BLASTN using default parameters) are described herein and are generally available.

For sequence comparison and homology determination, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith and Waterman (1981) Adv. Appl. Math. 2:482, by the homology alignment algorithm of Needleman and Wunsch, J. (1970) Mol. Biol. 48:443, by the search for similarity method of Pearson and Lipman (1988) Proc. Nat'l. Acad. Sci. USA 85:2444, by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information (on the world wide web at ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff and Henikoff (1989) Proc. Natl. Acad. Sci. USA 89:10915).

In addition to calculating percent sequence identity, the BLAST algorithm also performs a statistical analysis of the similarity between two sequences (see, e.g., Karlin and Altschul (1993) Proc. Nat'l. Acad. Sci. USA 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

Mutagenesis and Other Molecular Biology Techniques

Polynucleotides and polypeptides of the invention and used in the invention can be manipulated using molecular biological techniques. General texts which describe molecular biological techniques include Berger and Kimmel, *Guide to Molecular Cloning Techniques, Methods in Enzymology* volume 152 Academic Press, Inc., San Diego, Calif. ("Berger"); Sambrook et al., *Molecular Cloning—A Laboratory Manual* (3rd Ed.), Vol. 1-3, Cold Spring Harbor Laboratory, Cold Spring Harbor, N.Y., 2001 ("Sambrook") and *Current Protocols in Molecular Biology*, F. M. Ausubel et al., eds., *Current Protocols*, a joint venture between Greene Publishing Associates, Inc. and John Wiley and Sons, Inc., (supplemented through 2004) ("Ausubel")). These texts describe mutagenesis, the use of vectors, promoters and many other relevant topics related to, e.g., the generation of genes that include selector codons for production of proteins that include unnatural amino acids and to generation of orthogonal tRNAs, orthogonal synthetases, and pairs thereof.

Various types of mutagenesis are used in the invention, e.g., to mutate tRNA molecules, to produce libraries of tRNAs, to produce libraries of synthetases, and/or to insert selector codons that encode an unnatural amino acid in a protein or polypeptide of interest. They include, but are not limited to, site-directed mutagenesis, random point mutagenesis, homologous recombination, DNA shuffling or other recursive mutagenesis methods, chimeric construction, mutagenesis using uracil containing templates, oligonucleotide-directed mutagenesis, phosphorothioate-modified DNA mutagenesis, mutagenesis using gapped duplex DNA or the like, or any combination thereof. Additional suitable methods include point mismatch repair, mutagenesis using repair-deficient host strains, restriction-selection and restriction-purification, deletion mutagenesis, mutagenesis by total gene synthesis, double-strand break repair, and the like. Mutagenesis, e.g., involving chimeric constructs, is also included in the present invention. In one embodiment, mutagenesis can be guided by known information about the naturally occurring molecule or altered or mutated naturally occurring molecule, e.g., sequence, sequence comparisons, physical properties, crystal structure, or the like.

Host cells are genetically engineered (e.g., transformed, transduced or transfected) with the polynucleotides of the invention or constructs which include a polynucleotide of the invention, e.g., a vector of the invention, which can be, for example, a cloning vector or an expression vector. For example, the coding regions for the orthogonal tRNA, the orthogonal tRNA synthetase, and the protein to be derivatized are operably linked to gene expression control elements that are functional in the desired host cell. Typical vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both (e.g., shuttle vectors) and selection markers for both prokaryotic and eukaryotic systems. Vectors are suitable for replication and/or integration in prokaryotes, eukaryotes, or preferably both. See Giliman and Smith (1979) Gene 8:81; Roberts, et al. (1987) Nature, 328: 731; Schneider, B., et al. (1995) Protein Expr. Purif. 6435:10; Ausubel, Sambrook, Berger (all supra). The vector can be, for example, in the form of a plasmid, a bacterium, a virus, a naked polynucleotide, or a conjugated polynucleotide. The vectors are introduced into cells and/or microorganisms by standard methods including electroporation (From et al.

(1985) Proc. Natl. Acad. Sci. USA 82, 5824, infection by viral vectors, high velocity ballistic penetration by small particles with the nucleic acid either within the matrix of small beads or particles or on the surface (Klein et al. (1987) Nature 327:70-73), and/or the like.

A catalog of bacteria and bacteriophages useful for cloning is provided, e.g., by the ATCC, e.g., *The ATCC Catalogue of Bacteria and Bacteriophage* (1996) Gherna et al. (eds) published by the ATCC. Additional basic procedures for sequencing, cloning and other aspects of molecular biology and underlying theoretical considerations are also found in Sambrook (supra), Ausubel (supra), and in Watson et al. (1992) *Recombinant DNA Second Edition* Scientific American Books, NY. In addition, essentially any nucleic acid (and virtually any labeled nucleic acid, whether standard or non-standard) can be custom or standard ordered from any of a variety of commercial sources, such as the Midland Certified Reagent Company (Midland, Tex. mcrc.com), The Great American Gene Company (Ramona, Calif. available on the world wide web at genco.com), ExpressGen Inc. (Chicago, Ill. available on the world wide web at expressgen.com), Operon Technologies Inc. (Alameda, Calif.) and many others.

The engineered host cells can be cultured in conventional nutrient media modified as appropriate for such activities as, for example, screening steps, activating promoters or selecting transformants. These cells can optionally be cultured into transgenic organisms. Other useful references, e.g. for cell isolation and culture (e.g., for subsequent nucleic acid isolation or protein expression and/or purification) include Freshney (2000) *Culture of Animal Cells, a Manual of Basic Technique*, fourth edition, Wiley-Liss, New York and the references cited therein; Higgins and Hames (eds) (1999) *Protein Expression: A Practical Approach*, Practical Approach Series, Oxford University Press; Shuler et al. (eds) (1994) *Baculovirus Expression Systems and Biopesticides*, Wiley-Liss; Payne et al. (1992) *Plant Cell and Tissue Culture in Liquid Systems* John Wiley and Sons, Inc. New York, N.Y.; Gamborg and Phillips (eds) (1995) *Plant Cell, Tissue and Organ Culture*; Fundamental Methods Springer Lab Manual, Springer-Verlag (Berlin Heidelberg New York) and Atlas and Parks (eds) *The Handbook of Microbiological Media* (1993) CRC Press, Boca Raton, Fla.

Proteins and Polypeptides of Interest

Proteins or polypeptides of interest, e.g., having at least one heavy atom-containing amino acid (e.g., at least one brominated or iodinated amino acid such as bromoPhe or iodoPhe), are a feature of the invention, as are polypeptides comprising two or more different unnatural amino acids. Optionally, a protein of the invention will include a post-translational modification. An excipient (e.g., a pharmaceutically acceptable excipient), or more typically, a crystallization solution (containing, e.g., one or more buffers, salts, precipitation reagents, cryoprotectants, or the like) can also be present with the protein.

Methods of producing a protein in a cell (e.g., a non-eukaryotic cell, such as an *E. coli* cell or the like, or a eukaryotic cell) with a heavy atom-containing amino acid (e.g., a brominated or iodinated amino acid, e.g., bromoPhe or iodoPhe) at a specified position are also a feature of the invention. For example, the methods can include providing a cell comprising a nucleic acid that comprises at least one selector codon and that encodes the protein, an orthogonal tRNA that functions in the cell and recognizes the selector codon, and an orthogonal aminoacyl-tRNA synthetase. The O-RS comprises an amino acid sequence that is at least 90% identical to that of a naturally occurring tyrosyl aminoacyl-tRNA synthetase (TyrRS) and comprises two or more (e.g., three or more, four or more, or five) amino acids selected from the group consisting of: leucine at a position corresponding to Tyr32 of *M. jannaschii* TyrRS, serine or glutamate at a position corresponding to Glu107 of *M. jannaschii* TyrRS, proline at a position corresponding to Asp158 of *M. jannaschii* TyrRS, leucine or arginine at a position corresponding to Ile159 of *M. jannaschii* TyrRS, and glutamate or arginine at a position corresponding to Leu162 of *M. jannaschii* TyrRS. The cell is grown in an appropriate medium. The brominated or iodinated amino acid (or other heavy atom-containing amino acid) is provided and incorporated into the specified position in the protein during translation of the nucleic acid with the at least one selector codon, thereby producing the protein. A protein produced by this method is also a feature of the invention.

The invention also provides compositions that include proteins, where the proteins comprise, e.g., a heavy atom-containing amino acid (e.g., a brominated or iodinated amino acid, e.g., bromoPhe or iodoPhe). In certain embodiments, the protein comprises an amino acid sequence that is at least 75% identical to that of a known protein, e.g., a therapeutic protein, a diagnostic protein, an industrial enzyme, or portion thereof. Optionally, the protein comprises a protein crystal.

The compositions of the invention and compositions made by the methods of the invention optionally are present in a cell. The O-tRNA/O-RS pairs or individual components of the invention can then be used in a host system's translation machinery, which results in a heavy atom-containing amino acid being incorporated into a protein. International application No. PCT/US2004/011786, filed Apr. 16, 2004, entitled "Expanding the Eukaryotic Genetic Code," and WO 2002/085923, entitled "In vivo incorporation of unnatural amino acids" describe this process, and are incorporated herein by reference. For example, when an O-tRNA/O-RS pair is introduced into a host, e.g., *Escherichia coli*, the pair leads to the in vivo incorporation of a heavy atom-containing amino acid, e.g., a synthetic amino acid, such as a brominated or iodinated derivative of a tyrosine or phenylalanine, which can be exogenously added to the growth medium, into a protein in response to a selector codon. Optionally, the compositions of the present invention can be in an in vitro translation system, or in an in vivo system(s).

A cell of the invention provides the ability to synthesize proteins that comprise unnatural amino acids in large useful quantities. In one aspect, the composition optionally includes, e.g., at least 10 micrograms, at least 50 micrograms, at least 75 micrograms, at least 100 micrograms, at least 200 micrograms, at least 250 micrograms, at least 500 micrograms, at least 1 milligram, at least 10 milligrams, at least 50 milligrams, or at least 100 milligrams or more of the protein that comprises a heavy atom-containing amino acid (e.g., a brominated or iodinated amino acid) or multiple unnatural amino acids, or an amount that can be achieved with in vivo protein production methods (details on recombinant protein production and purification are provided herein). In another aspect, the protein is optionally present in the composition at a concentration of, e.g., at least 10 micrograms of protein per liter, at least 50 micrograms of protein per liter, at least 75 micrograms of protein per liter, at least 100 micrograms of protein per liter, at least 200 micrograms of protein per liter, at least 250 micrograms of protein per liter, at least 500 micrograms of protein per liter, at least 1 milligram of protein per liter, or at least 10 milligrams of protein per liter or more, in, e.g., a cell lysate, a buffer, a pharmaceutical buffer, or other liquid suspension (e.g., in a volume of, e.g., anywhere from about 1 nL to about 100 L). The production of large quantities (e.g., greater that that typically possible with other methods, e.g., in vitro translation) of a protein in a cell including at least one heavy atom-containing amino acid (e.g., at least one brominated or iodinated amino acid) is a feature of the invention.

The incorporation of a heavy atom-containing amino acid (e.g., a brominated or iodinated amino acid) can be done to facilitate solution of a protein's three-dimensional structure by x-ray crystallography, e.g., as described herein. Thus, as noted, the heavy atom amino acid-containing protein is optionally part of a protein crystal.

In one aspect of the invention, a composition includes at least one protein with at least one. e.g., at least two, at least three, at least four, at least five, at least six, at least seven, at least eight, at least nine, or at least ten or more unnatural amino acids, e.g., heavy atom-containing amino acids and/or other unnatural amino acids. The unnatural amino acids can be the same or different, e.g., there can be 1, 2, 3, 4, 5, 6, 7, 8, 9, or 10 or more different sites in the protein that comprise 1, 2, 3, 4, 5, 6, 7, 8, 9, or 10 or more different unnatural amino acids. In another aspect, a composition includes a protein with at least one, but fewer than all, of a particular amino acid present in the protein substituted with the heavy atom-containing amino acid. For a given protein with more than one unnatural amino acid, the unnatural amino acids can be identical or different (e.g., the protein can include two or more different types of unnatural amino acids, or can include two of the same unnatural amino acid). For a given protein with more than two unnatural amino acids, the unnatural amino acids can be the same, different or a combination of a multiple unnatural amino acid of the same kind with at least one different unnatural amino acid.

Essentially any protein (or portion thereof) that includes an unnatural amino acid, or that encodes multiple different unnatural amino acids (and any corresponding coding nucleic acid, e.g., which includes one or more selector codons) can be produced using the compositions and methods herein. No attempt is made to identify the hundreds of thousands of known proteins, any of which can be modified to include one or more unnatural amino acid, e.g., by tailoring any available mutation methods to include one or more appropriate selector codon in a relevant translation system. Common sequence repositories for known proteins include GenBank EMBL, DDBJ and the NCBI. Other repositories can easily be identified by searching the internet.

Typically, the proteins are, e.g., at least 60%, at least 70%, at least 75%, at least 80%, at least 90%, at least 95%, or at least 99% or more identical to any available protein (e.g., a therapeutic protein, a diagnostic protein, an industrial enzyme, or portion thereof, and the like), and they comprise one or more unnatural amino acid. Essentially any protein whose structure is of interest can be modified to include a heavy atom-containing amino acid. Examples of therapeutic, diagnostic, and other proteins that can be modified to comprise one or more heavy atom-containing amino acids can be found, but are not limited to, those in International application No. PCT/US2004/011786, filed Apr. 16, 2004, entitled "Expanding the Eukaryotic Genetic Code;" and, WO 2002/085923, entitled "In vivo incorporation of unnatural amino acids." Examples of therapeutic, diagnostic, and other proteins that can be modified to comprise one or more heavy atom-containing amino acids include, but are not limited to, e.g., Alpha-1 antitrypsin, Angiostatin, Antihemolytic factor, antibodies (further details on antibodies are found below), Apolipoprotein, Apoprotein, Atrial natriuretic factor, Atrial natriuretic polypeptide, Atrial peptides, C—X—C chemokines (e.g., T39765, NAP-2, ENA-78, Gro-a, Gro-b, Gro-c, IP-10, GCP-2, NAP-4, SDF-1, PF4, MIG), Calcitonin, CC chemokines (e.g., Monocyte chemoattractant protein-1, Monocyte chemoattractant protein-2, Monocyte chemoattractant protein-3, Monocyte inflammatory protein-1 alpha, Monocyte inflammatory protein-1 beta, RANTES, 1309, R83915, R91733, HCC1, T58847, D31065, T64262), CD40 ligand, C-kit Ligand, Collagen, Colony stimulating factor (CSF), Complement factor 5a, Complement inhibitor, Complement receptor 1, cytokines, (e.g., epithelial Neutrophil Activating Peptide-78, GROα/MGSA, GROβ, GROγ, MIP-1α, MIP-1δ, MCP-1), Epidermal Growth Factor (EGF), Erythropoietin ("EPO"), Exfoliating toxins A and B, Factor IX, Factor VII, Factor VIII, Factor X, Fibroblast Growth Factor (FGF), Fibrinogen, Fibronectin, G-CSF, GM-CSF, Glucocerebrosidase, Gonadotropin, growth factors, Hedgehog proteins (e.g., Sonic, Indian, Desert), Hemoglobin, Hepatocyte Growth Factor (HGF), Hirudin, Human serum albumin, Insulin, Insulin-like Growth Factor (IGF), interferons (e.g., IFN-α, IFN-β, IFN-γ), interleukins (e.g., IL-1, IL-2, IL-3, IL-4, IL-5, IL-6, IL-7, IL-8, IL-9, IL-10, IL11, IL-12, etc.), Keratinocyte Growth Factor (KGF), Lactoferrin, leukemia inhibitory factor, Luciferase, Neurturin, Neutrophil inhibitory factor (NIF), oncostatin M, Osteogenic protein, Parathyroid hormone, PD-ECSF, PDGF, peptide hormones (e.g., Human Growth Hormone), Pleiotropin, Protein A, Protein G, Pyrogenic exotoxins A, B, and C, Relaxin, Renin, SCF, Soluble complement receptor I, Soluble I-CAM 1, Soluble interleukin receptors (IL-1, 2, 3, 4, 5, 6, 7, 9, 10, 11, 12, 13, 14, 15), Soluble TNF receptor, Somatomedin, Somatostatin, Somatotropin, Streptokinase, Superantigens, i.e., Staphylococcal enterotoxins (SEA, SEB, SEC1, SEC2, SEC3, SED, SEE), Superoxide dismutase (SOD), Toxic shock syndrome toxin (TSST-1), Thymosin alpha 1, Tissue plasminogen activator, Tumor necrosis factor beta (TNF beta), Tumor necrosis factor receptor (TNFR), Tumor necrosis factor-alpha (TNF alpha), Vascular Endothelial Growth Factor (VEGEF), Urokinase and many others.

One class of proteins that can be made using the compositions and methods for in vivo incorporation of heavy atom-containing amino acids described herein includes transcriptional modulators or a portion thereof. Example transcriptional modulators include genes and transcriptional modulator proteins that modulate cell growth, differentiation, regulation, or the like. Transcriptional modulators are found in prokaryotes, viruses, and eukaryotes, including fungi, plants, yeasts, insects, and animals, including mammals, providing a wide range of therapeutic targets. It will be appreciated that expression and transcriptional activators regulate transcription by many mechanisms, e.g., by binding to receptors, stimulating a signal transduction cascade, regulating expression of transcription factors, binding to promoters and enhancers, binding to proteins that bind to promoters and enhancers, unwinding DNA, splicing pre-mRNA, polyadenylating RNA, and degrading RNA.

One class of proteins of the invention (e.g., proteins with one or more heavy atom-containing amino acids) include expression activators such as cytokines, inflammatory molecules, growth factors, their receptors, and oncogene products, e.g., interleukins (e.g., IL-1, IL-2, IL-8, etc.), interferons, FGF, IGF-I, IGF-II, FGF, PDGF, TNF, TGF-α, TGF-β, EGF, KGF, SCF/c-Kit, CD40L/CD40, VLA-4/VCAM-1, ICAM-1/LFA-1, and hyalurin/CD44; signal transduction molecules and corresponding oncogene products, e.g., Mos, Ras, Raf, and Met; and transcriptional activators and suppressors, e.g., p53, Tat, Fos, Myc, Jun, Myb, Rel, and steroid hormone receptors such as those for estrogen, progesterone, testosterone, aldosterone, the LDL receptor ligand and corticosterone.

Enzymes (e.g., industrial enzymes) or portions thereof with at least one heavy atom-containing amino acid are also provided by the invention. Examples of enzymes include, but are not limited to, e.g., amidases, amino acid racemases, acylases, dehalogenases, dioxygenases, diarylpropane peroxidases, epimerases, epoxide hydrolases, esterases, isomerases, kinases, glucose isomerases, glycosidases, glycosyl transferases, haloperoxidases, monooxygenases (e.g., p450s), lipases, lignin peroxidases, nitrile hydratases, nitrilases, proteases, phosphatases, subtilisins, transaminase, and nucleases.

Many of these proteins are commercially available (see, e.g., the Sigma BioSciences 2004 catalog and price list), and the corresponding protein sequences and genes and, typically, many variants thereof, are well-known (see, e.g., Genbank). Any of them can be modified by the insertion of one or more heavy atom-containing amino acid or other unnatural amino acid according to the invention, e.g., to facilitate determination of the protein's structure A variety of other proteins can also be modified to include one or more heavy atom-containing amino acid. For example, the invention can include substituting one or more natural amino acids in one or more vaccine proteins with a heavy atom-containing amino acid, e.g., in proteins from infectious fungi, e.g., *Aspergillus, Candida* species; bacteria, particularly *E. coli*, which serves a model for pathogenic bacteria, as well as medically important bacteria such as *Staphylococci* (e.g., *aureus*), or *Streptococci* (e.g., *pneumoniae*); protozoa such as sporozoa (e.g., *Plasmodia*), rhizopods (e.g., *Entamoeba*) and flagellates (*Trypanosoma, Leishmania, Trichomonas, Giardia*, etc.); viruses such as (+) RNA viruses (examples include Poxviruses e.g., vaccinia; Picornaviruses, e.g. polio; Togaviruses, e.g., *rubella*; Flaviviruses, e.g., HCV; and Coronaviruses), (−) RNA viruses (e.g., Rhabdoviruses, e.g., VSV; Paramyxovimses, e.g., RSV; Orthomyxovimses, e.g., influenza; Bunyaviruses; and Arenaviruses), dsDNA viruses (Reoviruses, for example), RNA to DNA viruses, i.e., Retroviruses, e.g., HIV and HTLV, and certain DNA to RNA viruses such as Hepatitis B.

Agriculturally related proteins such as insect resistance proteins (e.g., the Cry proteins), starch and lipid production enzymes, plant and insect toxins, toxin-resistance proteins, Mycotoxin detoxification proteins, plant growth enzymes (e.g., Ribulose 1,5-Bisphosphate Carboxylase/Oxygenase, "RUBISCO"), lipoxygenase (LOX), and Phosphoenolpyruvate (PEP) carboxylase are also suitable targets for heavy atom-containing amino acid or other unnatural amino acid modification.

In certain embodiments, the protein or polypeptide of interest (or portion thereof) in the methods and/or compositions of the invention is encoded by a nucleic acid. Typically, the nucleic acid comprises at least one selector codon, at least two selector codons, at least three selector codons, at least four selector codons, at least five selector codons, at least six selector codons, at least seven selector codons, at least eight selector codons, at least nine selector codons, or ten or more selector codons.

Genes coding for proteins or polypeptides of interest can be mutagenized using methods well-known to one of skill in the art and described herein under "Mutagenesis and Other Molecular Biology Techniques" to include, e.g., one or more selector codon for the incorporation of a heavy atom-containing amino acid. For example, a nucleic acid for a protein of interest is mutagenized to include one or more selector codon, providing for the insertion of the one or more heavy atom-containing amino acids. The invention includes any such variant, e.g., mutant, versions of any protein, e.g., including at least one heavy atom-containing amino acid. Similarly, the invention also includes corresponding nucleic acids, i.e., any nucleic acid with one or more selector codon that encodes one or more heavy atom-containing amino acid.

To make a protein that includes a heavy atom-containing amino acid, one can use host cells and organisms that are adapted for the in vivo incorporation of the heavy atom-containing amino acid via orthogonal tRNA/RS pairs. Host cells are genetically engineered (e.g., transformed, transduced or transfected) with one or more vectors that express the orthogonal tRNA, the orthogonal tRNA synthetase, and a vector that encodes the protein to be derivatized. Each of these components can be on the same vector, or each can be on a separate vector, or two components can be on one vector and the third component on a second vector. The vector can be, for example, in the form of a plasmid, a bacterium, a virus, a naked polynucleotide, or a conjugated polynucleotide.

Defining Polypeptides by Immunoreactivity

Because the polypeptides of the invention provide a variety of new polypeptide sequences (e.g., comprising heavy atom-containing amino acids in the case of proteins synthesized in the translation systems herein, or, e.g., in the case of the novel synthetases, novel sequences of standard amino acids), the polypeptides also provide new structural features which can be recognized, e.g., in immunological assays. The generation of antisera which specifically bind the polypeptides of the invention, as well as the polypeptides which are bound by such antisera, are a feature of the invention. The term "antibody," as used herein, includes, but is not limited to a polypeptide substantially encoded by an immunoglobulin gene or immunoglobulin genes, or fragments thereof which specifically bind and recognize an analyte (antigen). Examples include polyclonal, monoclonal, chimeric, and single chain antibodies, and the like. Fragments of immunoglobulins, including Fab fragments and fragments produced by an expression library, including phage display, are also included in the term "antibody" as used herein. See, e.g., Paul (1999) *Fundamental Immunology*, 4th Ed., Raven Press, New York, for antibody structure and terminology.

In order to produce antisera for use in an immunoassay, one or more of the immunogenic polypeptides is produced and purified as described herein. For example, recombinant protein can be produced in a recombinant cell. An inbred strain of mice (used in this assay because results are more reproducible due to the virtual genetic identity of the mice) is immunized with the immunogenic protein(s) in combination with a standard adjuvant, such as Freund's adjuvant, and a standard mouse immunization protocol (see, e.g., Harlow and Lane (1988) *Antibodies, A Laboratory Manual*, Cold Spring Harbor Publications, New York, for a standard description of antibody generation, immunoassay formats and conditions that can be used to determine specific immunoreactivity. Additional details on proteins, antibodies, antisera, etc. can be found in U.S. Ser. No. 60/479,931, 60/463,869, and 60/496,548 entitled "Expanding the Eukaryotic Genetic Code;" WO 2002/085923, entitled "In vivo Incorporation of Unnatural Amino Acids," patent application entitled "Glycoprotein synthesis" filed Jan. 16, 2003, U.S. Ser. No. 60/441,450, and International Application No. PCT/US03/41346, entitled "Protein Arrays," filed on Dec. 22, 2003.

Use of O-tRNA, O-RS, and O-tRNA/O-RS Pairs

The compositions of the invention and compositions made by the methods of the invention optionally are in a cell. The O-tRNA/O-RS pairs or individual components of the invention can then be used in a host system's translation machinery, which results in a heavy atom-containing amino acid being incorporated into a protein. The patent application "In vivo Incorporation of Unnatural Amino Acids" WO 2002/085923 by Schultz, et al. describes this process and is incorporated herein by reference. For example, when an O-tRNA/O-RS pair is introduced into a host, e.g., *Escherichia coli*, the pair leads to the in vivo incorporation of a heavy atom-containing amino acid, which can be exogenously added to the growth medium, into a protein, e.g., any protein whose structure is of interest, in response to a selector codon, e.g., an amber nonsense codon. Optionally, the compositions of the invention can be in an in vitro translation system, or in an in vivo system(s). Proteins with the heavy atom-containing amino acid can be used to facilitate studies on protein structure, function, and the like.

Kits

Kits are also a feature of the invention. For example, a kit for producing a protein with a brominated or iodinated amino acid at a specified position is provided, where the kit includes a cell comprising an orthogonal tRNA that functions in the cell and recognizes a selector codon and an orthogonal aminoacyl-tRNA synthetase, packaged in one or more containers. The orthogonal aminoacyl-tRNA synthetase includes an amino acid sequence that is at least 90% identical to that of a naturally occurring tyrosyl aminoacyl-tRNA synthetase (TyrRS) and that comprises two or more (e.g., three or more, four or more, or five) amino acids selected from the group consisting of: leucine at a position corresponding to Tyr32 of *M. jannaschii* TyrRS, serine or glutamate at a position corresponding to Glu107 of *M. jannaschii* TyrRS, proline at a position corresponding to Asp158 of *M. jannaschii* TyrRS, leucine or arginine at a position corresponding to Ile159 of *M. jannaschii* TyrRS, and glutamate or arginine at a position corresponding to Leu162 of *M. jannaschii* TyrRS. For example, the O-RS can comprise an amino acid sequence of SEQ ID NO:3 or 4 or a conservative variant thereof. In one class of embodiments, the kit further includes the brominated or iodinated amino acid (e.g., bromoPhe or iodoPhe). In another class of embodiments, the kit further comprises instructional materials for producing the protein, an appropriate cell growth medium, reagents for introducing a target nucleic acid encoding the protein of interest and including the selector codon into the cell, and/or the like. Any composition, system or device of the invention can also be associated with appropriate packaging materials (e.g., containers, etc.) for production in kit form.

Protein Structure Determination

As noted, site-specific, efficient incorporation of heavy atom-containing amino acids (e.g., iodoPhe or bromoPhe) into proteins facilitates solution of protein structures by x-ray crystallography. Derivatization of proteins with heavy atoms is commonly used to permit phase determination, for example, by multiple isomorphous replacement (MIR), single isomorphous replacement (SIR), multiwavelength anomalous dispersion (MAD), or single wavelength anomalous dispersion (SAD) methods. Site-specific incorporation of heavy atoms, e.g., using the methods and compositions of the present invention, provides flexibility in choosing derivatization site(s) and heavy atom type and numbers. Heavy atom incorporation using the methods and compositions of the invention can be used to facilitate determination of the structure of essentially any protein, but can be particularly advantageous for proteins with few methionines, in which incorporation of selenomethionine is difficult, or for which other methods of determining initial phases are unsatisfactory, or when access to a synchrotron is not available.

Thus, one general class of embodiments provides methods of determining a protein structure. In the methods, a protein with a heavy atom-containing amino acid at a specified position is provided by expressing the protein in a translation system that includes an orthogonal tRNA and an orthogonal aminoacyl-tRNA synthetase which preferentially aminoacylates the orthogonal tRNA with the heavy atom-containing amino acid. The protein including the heavy atom-containing amino acid is crystallized, thereby creating a heavy atom-containing protein crystal. Diffraction data is collected from the heavy atom-containing protein crystal and used to determine the structure, e.g., by MIR, SIR, MAD, SAD, or a combination thereof.

For example, in a preferred class of embodiments, SAD phasing is used. In this class of embodiments, the structure of the protein is determined by a process that comprises collecting diffraction data from the heavy atom-containing protein crystal at a single wavelength and measuring anomalous differences between Friedel mates, which result from the presence of the heavy atom in the crystal. In brief, collection of diffraction data involves measuring the intensities of a large number of reflections produced by exposure of one or more protein crystals to a beam of x-rays. Each reflection is identified by indices h, k, and l. Typically, the intensities of Friedel mates (pairs of reflections with indices h,k,l and -h,-k,-l) are the same. However, when a heavy atom is present in the protein crystal and the wavelength of the x-rays used is near an absorption edge for that heavy atom, anomalous scattering by the heavy atom results in differences between the intensities of certain Friedel mates. These anomalous differences can be used to calculate phases that, in combination with the measured intensities, permit calculation of an electron density map into which a model of the protein structure can be built.

The protein can be expressed in an in vivo or in vitro translation system, e.g., as described herein. In certain embodiments, the orthogonal aminoacyl-tRNA synthetase comprises an amino acid sequence of SEQ ID NO:3 or SEQ ID NO:4 or a conservative variant thereof. Similarly, the orthogonal-tRNA can comprise a polynucleotide sequence of SEQ ID NO:5 or a conservative variant thereof.

The heavy atom-containing amino acid can be essentially any of those described herein. For example, the heavy atom-containing amino acid can be a brominated or iodinated amino acid, e.g., L-2-iodophenylalanine, L-3-iodophenylalanine, L-2-iodotyrosine, L-3-iodotyrosine, L-2-bromophenylalanine, L-3-bromophenylalanine, L-2-bromotyrosine, or L-3-bromotyrosine. In a preferred class of embodiments, the brominated or iodinated amino acid is L-4-bromophenylalanine or L-4-iodophenylalanine.

The wavelength at which diffraction data is collected can be essentially any convenient wavelength. For example, data can be conveniently collected using an in-house generator with a copper anode at the CuKα wavelength of 1.5418 Å. It is worth noting that iodine is preferred over bromine as the heavy atom for use at this wavelength, since the anomalous signal from bromine is negligible at this wavelength. Alternatively or in addition, data can be collected at any of a variety of wavelengths at a synchrotron or other tunable source. For example, data is optionally collected at a wavelength selected to maximize anomalous signal from the particular heavy atom incorporated in the protein, minimize radiation damage to the protein crystal, and/or the like.

In another class of embodiments, MAD phasing is used. In this class of embodiments, the structure of the protein is determined by a process that comprises collecting diffraction data from the heavy atom-containing protein crystal at two or more wavelengths and measuring dispersive differences between data collected at different wavelengths. For example, data is optionally collected at two wavelengths, e.g., at the point of inflection of the absorption curve of the heavy atom and at a remote wavelength away from the absorption edge, e.g., utilizing a synchrotron as the radiation source.

Techniques for structure determination, including phasing by SAD, MIR, and MAD, are well known. See, e.g., Stout and Jensen (1989) *X-ray structure determination: a practical guide, 2nd Edition* Wiley Publishers, New York; Ladd and Palmer (1993) *Structure determination by X-ray crystallography, 3rd Edition* Plenum Press, New York; Blundell and Johnson (1976) *Protein Crystallography* Academic Press, New York; Glusker and Trueblood (1985) *Crystal structure analysis: A primer, 2nd Ed.* Oxford University Press, New York; *International Tables for Crystallography, Vol. F. Crystallography of Biological Macromolecules*; McPherson (2002) *Introduction to Macromolecular Crystallography* Wiley-Liss; McRee and David (1999) *Practical Protein Crystallography, Second Edition* Academic Press; Drenth (1999) *Principles of Protein X-Ray Crystallography* (Springer Advanced Texts in Chemistry) Springer-Verlag. MAD phasing is also reviewed, e.g., in Fanchon and Hendrickson (1991) Chapter 15 of *Crystallographic Computing. Volume 5* IUCr/Oxford University Press and Murthy (1996) Chapter 5 of *Crystallographic Methods and Protocols* Humana Press. Further examples of SAD phasing are described in the examples herein and in, e.g., Dauter et al. (2000) "Novel approach to phasing proteins: derivatization by short cryo-soaking with halides" Acta Cryst.D56:232-237; Dauter (2002) "New approaches to high-throughput phasing" Curr. Opin. Structural Biol. 12:674-678; Chen et al. (1991) "Crystal structure of a bovine neurophysin-II dipeptide complex at 2.8 Å determined from the single-wavelength anomalous scattering signal of an incorporated iodine atom" Proc. Natl Acad. Sci. USA, 88:4240-4244; and Gavira et al. (2002) "Ab initio crystallographic structure determination of insulin from protein to electron density without crystal handling" Acta Cryst.D58:1147-1154.

In addition, a variety of programs to facilitate data collection, phase determination, model building and refinement, and the like are publicly available. Examples include, but are not limited to, the HKL2000 package (Otwinowski and Minor (1997) "Processing of X-ray Diffraction Data Collected in Oscillation Mode" Methods in Enzymology 276: 307-326), the CCP4 package (Collaborative Computational Project (1994) "The CCP4 suite: programs for protein crystallography" Acta Crystallogr D 50:760-763), SOLVE and RESOLVE (Terwilliger and Berendzen (1999) Acta Crystallogr D 55 (Pt 4):849-861), SHELXS and SHELXD (Schneider and Sheldrick (2002) "Substructure solution with SHELXD" Acta Crystallogr D Biol Crystallogr 58:1772-1779), Refmac5 (Murshudov et al. (1997) "Refinement of Macromolecular Structures by the Maximum-Likelihood Method" Acta Crystallogr D 53:240-255), and O (Jones et al. (1991) "Improved methods for building protein models in electron density maps and the location of errors in these models" Acta Crystallogr A 47 (Pt 2):110-119).

Proteins are typically purified prior to crystallization, e.g., from natural sources, from an in vitro translation system, from cells (e.g., bacteria, yeast, etc.) overexpressing a protein of interest (see, e.g., Ausubel, Sambrook, and Berger, all supra), or the like, by any of a number of methods well known in the art, including, e.g., ammonium sulfate or ethanol precipitation, centrifugation, acid or base extraction, column chromatography, affinity column chromatography, anion or cation exchange chromatography, phosphocellulose chromatography, high performance liquid chromatography (HPLC), gel filtration, hydrophobic interaction chromatography, hydroxylapatite chromatography, lectin chromatography, gel electrophoresis, and the like.

In addition to other references noted herein, a variety of protein purification methods are well known in the art, including, e.g., those set forth in R. Scopes (1982) *Protein Purification*, Springer-Verlag, N.Y.; Deutscher (1990) *Methods in Enzymology Vol. 182: Guide to Protein Purification*, Academic Press, Inc. N.Y.; Sandana (1997) *Bioseparation of Proteins*, Academic Press, Inc.; Bollag et al. (1996) *Protein Methods*, 2nd Edition Wiley-Liss, NY; Walker (1996) *The Protein Protocols Handbook* Humana Press, NJ; Harris and Angal (1990) *Protein Purification Applications: A Practical Approach*, IRL Press at Oxford, Oxford, England; Harris and Angal *Protein Purification Methods: A Practical Approach*, IRL Press at Oxford, Oxford, England; Scopes (1993) *Protein Purification: Principles and Practice* 3rd Edition Springer Verlag, NY; Janson and Ryden (1998) *Protein Purification: Principles, High Resolution Methods and Applications*, Second Edition, Wiley-VCH, NY; and Walker (1998) *Protein Protocols on CD-ROM*, Humana Press, NJ; and the references cited therein.

Well known techniques for refolding proteins can be used if necessary to obtain the active conformation of the protein when the protein is denatured during intracellular synthesis, isolation or purification. Methods of reducing, denaturing and renaturing proteins are well known to those of skill in the art (see the references above and Debinski, et al. (1993) J. Biol. Chem. 268:14065-14070; Kreitman and Pastan (1993) Bioconjug. Chem. 4:581-585; and Buchner, et al. (1992) Anal. Biochem. 205:263-270).

The nucleotide sequence encoding the polypeptide can optionally be fused in-frame to a sequence encoding a module (e.g., a domain or tag) that facilitates purification of the polypeptide and/or facilitates association of the fusion polypeptide with a particle, a solid support or another reagent. Such modules include, but are not limited to, metal chelating peptides such as histidine-tryptophan modules that allow purification on and/or binding to immobilized metals (e.g., a hexahistidine tag), a sequence which binds glutathione (e.g., GST), a hemagglutinin (HA) tag (corresponding to an epitope derived from the influenza hemagglutinin protein; Wilson, I., et al. (1984) Cell 37:767), maltose binding protein sequences, the FLAG epitope utilized in the FLAGS extension/affinity purification system (Immunex Corp, Seattle, Wash.), and the like. The inclusion of a protease-cleavable polypeptide linker sequence between the purification domain and the sequence of the invention is useful to permit removal of the module following, or during, purification of the polypeptide.

Conditions for crystallizing proteins to obtain diffraction-quality crystals can be determined empirically using techniques known in the art. See, e.g., McPherson (1999) *Crystallization of Biological Macromolecules* Cold Spring Harbor Laboratory, Bergfors (1999) *Protein Crystallization* International University Line, and Mullin (1993) *Crystallization* Butterworth-Heinemann.

EXAMPLES

It is understood that the examples and embodiments described herein are for illustrative purposes only and that various modifications or changes in light thereof will be suggested to persons skilled in the art and are to be included within the spirit and purview of this application. Accordingly, the following examples are offered to illustrate, but not to limit, the claimed invention.

Example 1

Production of Orthogonal Synthetase/tRNA Pair

To selectively incorporate iodoPhe (FIG. 1 Panel A) into proteins in response to an amber TAG codon, a *Methanococcus jannaschii* tRNA$_{CUA}^{Tyr}$-TyrRS pair was constructed and used. This tRNA-synthetase pair is orthogonal to all tRNA-synthetase pairs in *E. coli*, i.e., neither the *M. jannaschii* tyrosyl tRNA nor the synthetase cross-reacts with any of the endogenous tRNA or synthetases in *E. coli*. This condition ensures that iodoPhe is incorporated into proteins with high translational fidelity. To alter the specificity of the TyrRS synthetase to selectively recognize iodoPhe, a library of *M. jannaschii* TyrRS mutants was generated by randomizing five residues (Tyr32, Glu107, Asp158, Ile159 and Leu162) in the tyrosine binding pocket of TyrRS (FIG. 1 Panel B), based on the crystal structure of the homologous *B. stearothermophilus* TyrRS-tyrosyl adenylate complex (Brick et al. (1989) Structure of tyrosyl-tRNA synthetase refined at 2.3 Å resolution. Interaction of the enzyme with the tyrosyl adenylate intermediate. J Mol Biol 208:83-98). The mutant TyrRS library was then subjected to alternating positive and negative selections. The positive selection is based on the suppression of an amber mutation at a permissive site (Asp112) in the type I chloramphenicol acetyltransferase (CAT) gene in the presence of iodoPhe and the orthogonal *M. jannaschii* tyrosyl tRNA-synthetase pair. The negative selection is based on the suppression of amber mutations at permissive sites (Gln2, Asp44 and Gly65) in the toxic barnase gene in the absence of iodoPhe. Only synthetases that efficiently incorporate iodoPhe, and no endogenous amino acid, in response to the amber codon can survive both selections.

After five rounds of alternating positive and negative selections, one synthetase variant was identified that survives in 120 μg/mL of chloramphenicol in the presence of iodoPhe, but dies in 20 μg/mL of chloramphenicol in the absence of iodoPhe. When the mutant synthetase was used to suppress a Tyr7→TAG mutant of the Z-domain protein (with a C-terminal His$_6$ tag) (Wang et al. (2003) "Addition of the keto functional group to the genetic code of *Escherichia coli*" Proc Natl Acad Sci U S A 100:56-61) in the presence of iodoPhe, full-length protein was produced (FIG. 1 Panel C). In the absence of either iodoPhe or the mutant synthetase, no Z-domain protein was detected by silver staining on an SDS-PAGE gel (FIG. 1 Panel C). The selective incorporation of iodoPhe was further verified by electrospray ionization Fourier transform ion cyclotron resonance mass spectrometry (FT-ICR MS). For iodoPhe substituted Z-domain protein lacking the first methionine, the calculated and the experimental monoisotopic mass are 7902.720 Da and 7902.728 Da, respectively. The yield of iodoPhe-substituted Z-domain protein was 3.8 mg/L in minimal media. For comparison, the yield of Z-domain protein was 4.6 mg/L when the wild type *M. jannaschii* TyrRS was expressed instead of the mutant TyrRS (which results incorporation of tyrosine in the protein). The iodoPhe specific synthetase (SEQ ID NO:3, corresponding nucleotide sequence is SEQ ID NO:1; FIG. 4 Panel A) has the following mutations: Tyr32Leu, Glu107Ser, Asp158Pro, Ile159Leu and Leu162Glu. The Tyr32→Leu32 and Asp158→Pro158 mutations may disrupt the hydrogen bonds with the hydroxyl group of tyrosine to create a hydrophobic pocket that accommodates iodoPhe. From these results, we conclude that iodoPhe can be incorporated into proteins in *E. coli* site-specifically and quantitatively.

It is worth noting that this iodoPhe specific synthetase, presented in the sequence listing as SEQ ID NO:3, can also specifically charge the O-tRNA (FIG. 5) with bromoPhe. The sequence of an additional synthetase that can specifically charge the O-tRNA with either iodoPhe or bromoPhe is presented in FIG. 4 Panel B and in the sequence listing as SEQ ID NO:4 (corresponding nucleotide sequence is SEQ ID NO:2).

Example 2 iodoPhe Incorporation Enables Sad Phasing

The synthetases described in Example 1 can be used to efficiently and site-specifically incorporate p-iodo-L-phenylalanine (iodoPhe) into proteins in response to an amber TAG codon. The selective introduction of the anomalously scattering iodine atom into proteins should facilitate SAD experiments on in-house X-ray sources. To illustrate this, a Phe153→iodoPhe mutant of bacteriophage T4 lysozyme was generated and its crystal structure was successfully determined using considerably less data than for the equivalent experiment with cysteine and methionine. The iodoPhe residue, although present in the hydrophobic core of the protein, did not perturb the protein structure to any significant degree. The ability to selectively introduce this and other heavy atom containing amino acids into proteins will further facilitate the structural study of proteins.

To determine the utility of iodoPhe incorporation for SAD phasing in protein crystallography, bacteriophage T4 lysozyme was used as a model system. Cys54 and Cys97 in T4 lysozyme were mutated to Thr and Ala to enhance the stability of the protein as previously reported (Eriksson et al. (1993) "Similar hydrophobic replacements of Leu99 and Phe153 within the core of T4 lysozyme have different structural and thermodynamic consequences" J Mol Biol 229:747-769). The codon corresponding to Phe153 of T4 lysozyme, a residue in the hydrophobic core of the large lobe of T4 lysozyme, was mutated to TAG. The evolved orthogonal synthetase-tRNA pair was then used to suppress the amber codon with iodoPhe in *E. coli*. The expressed mutant T4 lysozyme was purified by cation-exchange chromatography and size-exclusion chromatography. The yield after purification was 5.7 mg/L in minimal media. Crystals were grown under the same conditions as previously reported for crystallization of T4 lysozyme and its mutants (Eriksson et al. (1993) "Similar hydrophobic replacements of Leu99 and Phe153 within the core of T4 lysozyme have different structural and thermodynamic consequences" J Mol Biol 229:747-769).

The structure of the T4 lysozyme was determined from data collected on an in-house X-ray generator at the CuKα wavelength (1.5418 Å). In all, 360° of data were collected at 100° K to a maximum resolution of 2.0 Å, with no attempt being made to collect Friedel mates on the same image or close in time. Subsequently, to establish the minimum amount of data necessary for structure determination, the dataset was split into 6 different oscillation ranges representing different values of data redundancy (Table 1). As would be expected, the incorporation of iodoPhe for Phe significantly increases the anomalous signal (δf") for T4 lysozyme. The average ratio of Bijvoet pairs (<|ΔF|>/<F>) is approximately 3% for all datasets (Table 1), in close agreement with the 4% calculated using the method of Hendrickson and Teeter ("Structure of the hydrophobic protein crambin determined directly from the anomalous scattering of sulfur" 1981, Nature 290:107-113). This is in contrast to the 0.9% computed for native T4 lysozyme with 1309 atoms and 7 sulfur atoms. In addition to an enhanced signal, the ability to place a fixed number of iodines within the hydrophobic core of a protein provides a significant advantage relative to other techniques such as iodine soaks (Dauter et al. (2000) "Novel approach to phasing proteins: derivatization by short cryo-soaking with halides" Acta Crystallogr D 56(Pt 2):232-237 and Nagem et al. (2001) "Protein crystal structure solution by fast incorporation of negatively and positively charged anomalous scatterers" Acta Crystallogr D 57:996-1002), where multiple low occupancy sites may confound substructure solution.

Figure 2A:
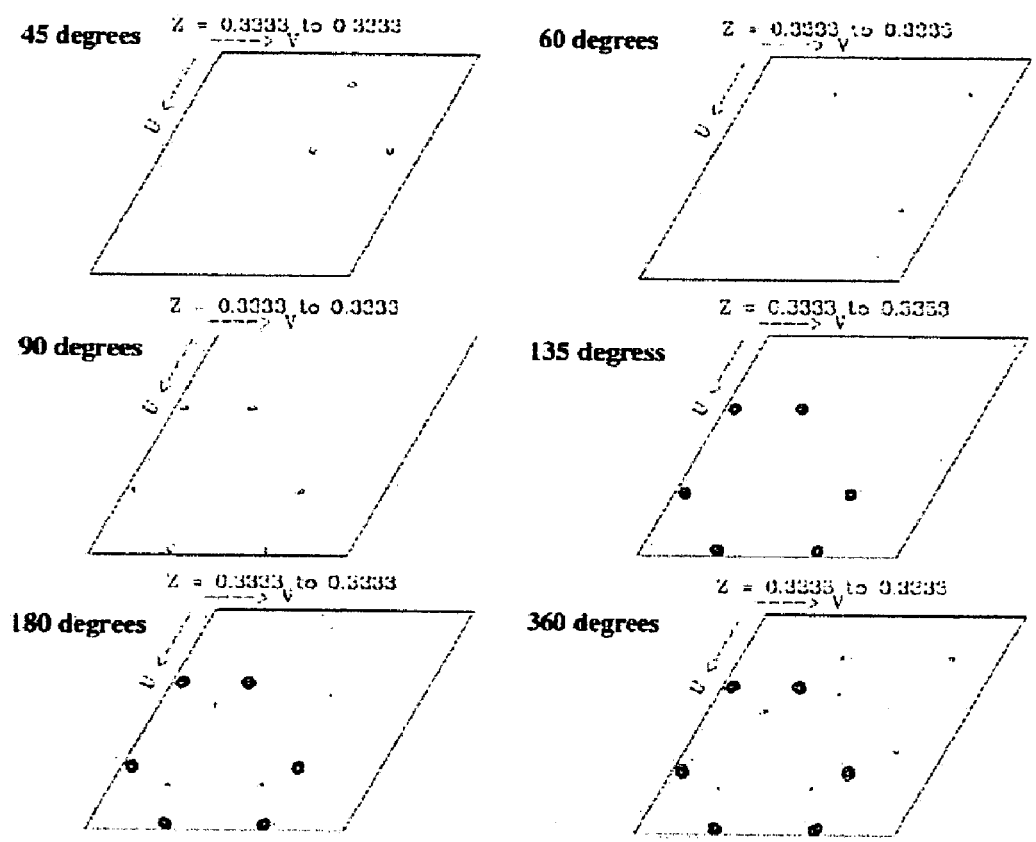
FIG. 2 shows Patterson and difference Fourier maps for the anomalous datasets. Panel A shows first Harker sections of Patterson maps of the iodoPhe incorporated crystal for 45, 60, 90, 135, 180, and 360 degrees of data collected. The iodine self peaks appear after 90° of data are collected; additional peaks present on the 180 and 360° sets are the self-peaks from $Cl^{-1}$ ions present in the crystal. The graphics were produced with FFT and NPO from the CCP4 program package. Plots are contoured at 3.0 sigma; subsequent contours are plotted in 3.0 sigma steps. Panel B shows a difference Fourier map using phases from lysozyme structure 1L63 (Nicholson et al. (1991) Biochemistry 30:9816-9828) and anomalous difference amplitudes. The iodine site as well as a number of sulfurs and ions can be clearly distinguished. The electron density map is contoured at 3σ's above the mean and was calculated with programs from the CCP4 package; the figure was produced by BobScript and Raster3D (Kraulis (1991) "MOL-SCRIPT: a program to produce both detailed and schematic plots of protein structures" J. Appl. Crystallogr. 24:946-950; Merritt and Murphy (1994) "Raster3D Version 2.0. A program for photorealistic molecular graphics" Acta Crystallogr D 50:869-873; and Esnouf (1997) "An extensively modified version of MolScript that includes greatly enhanced coloring capabilities" J Mol Graph Mode115, 132-134:112-133).
Figure 2B:
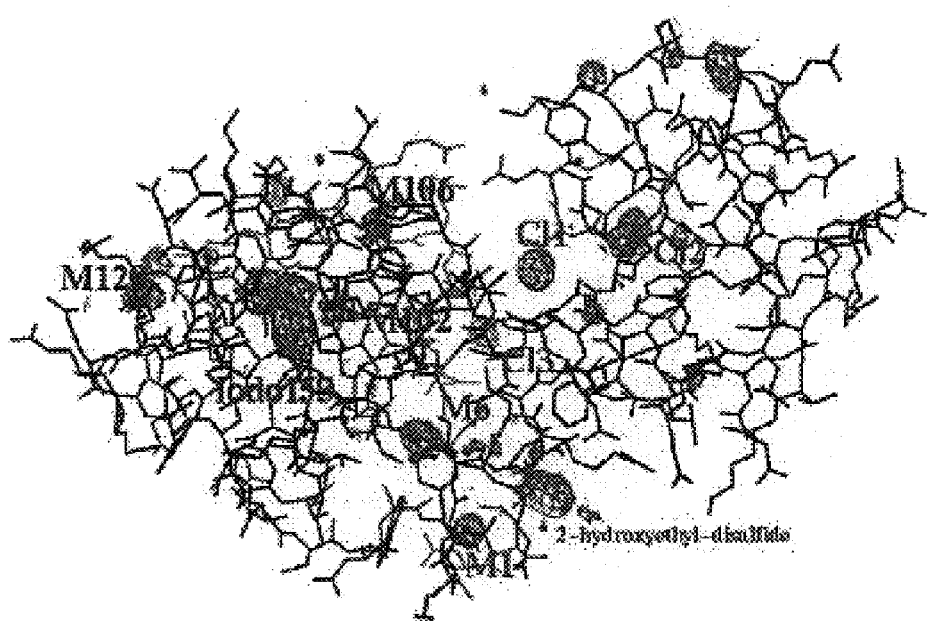

Prior to phase determination, Patterson maps and anomalous difference Fourier maps were calculated to characterize the anomalous signal. Self vectors for iodine atoms are clearly evident in Harker sections of the Patterson maps in all datasets with a mean redundancy greater than 4.4 (90°) (FIG. 2 Panel A). Above a redundancy of 9.0 (180° of data), self peaks for additional chloride ions become evident at the 3σ level, but no significant sulfur vectors were ever visible. The anomalous difference Fourier maps calculated from phases derived from a T4 lysozyme structure (PDB code 1L63; Nicholson et al. (1991) "Analysis of the interaction between charged side chains and the alpha-helix dipole using designed thermostable mutants of phage T4 lysozyme" Biochemistry 30:9816-9828) show significant density in all data sets, not only for the iodine but also for all 5 methionine sulfurs present in the protein, three putative chlorine ions, and a 2-hydroxyethyl disulfide molecule included in the crystallization conditions (FIG. 2 Panel B).

Figure 3A:
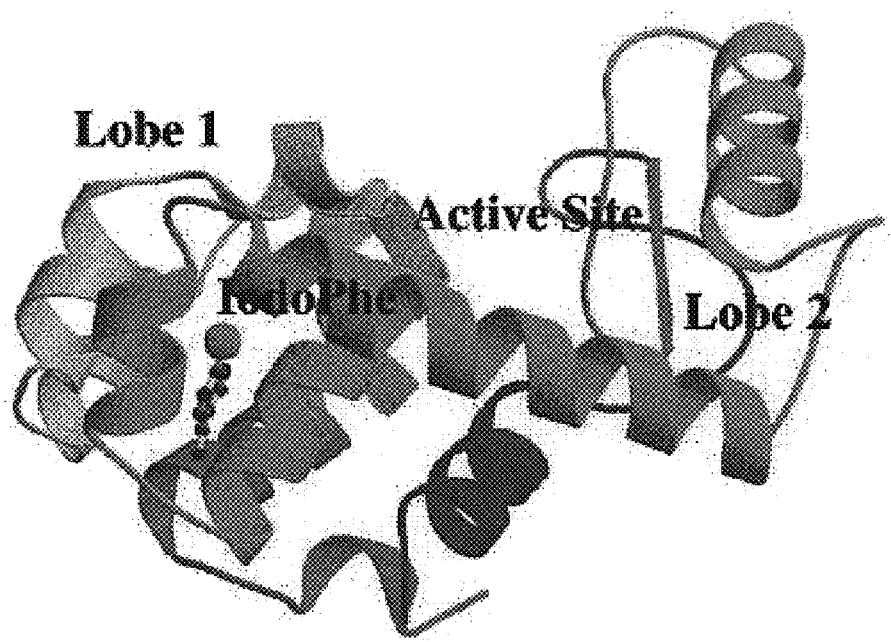
FIG. 3 illustrates structures and representative electron density of the iodoPhe. Panel A shows a ribbon diagram of T4 lysozyme with an iodoPhe at position 153. The iodoPhe is presented in a ball and stick representation. Panel B shows initial electron density around iodoPhe after phase refinement of initial phases generated by SOLVE with RESOLVE for the dataset representing 135° of data. The final refined model is shown in a ball and stick representation for comparison. Panel C shows a comparison of the hydrophobic core of native (Nicholson et al. (1991) Biochemistry 30:9816-9828) (1L63) and iodoPhe T4 lysozyme. Figures produced by Bobscript and Raster3D.
Figure 3B:
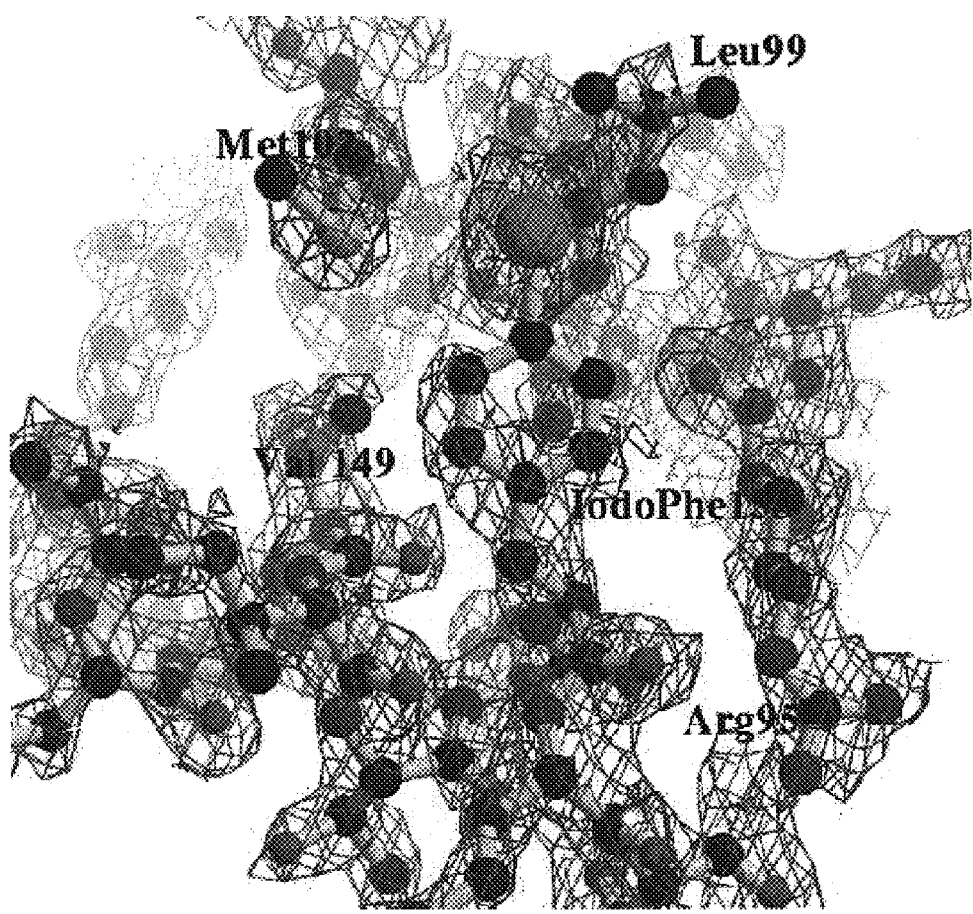
Figure 3C:
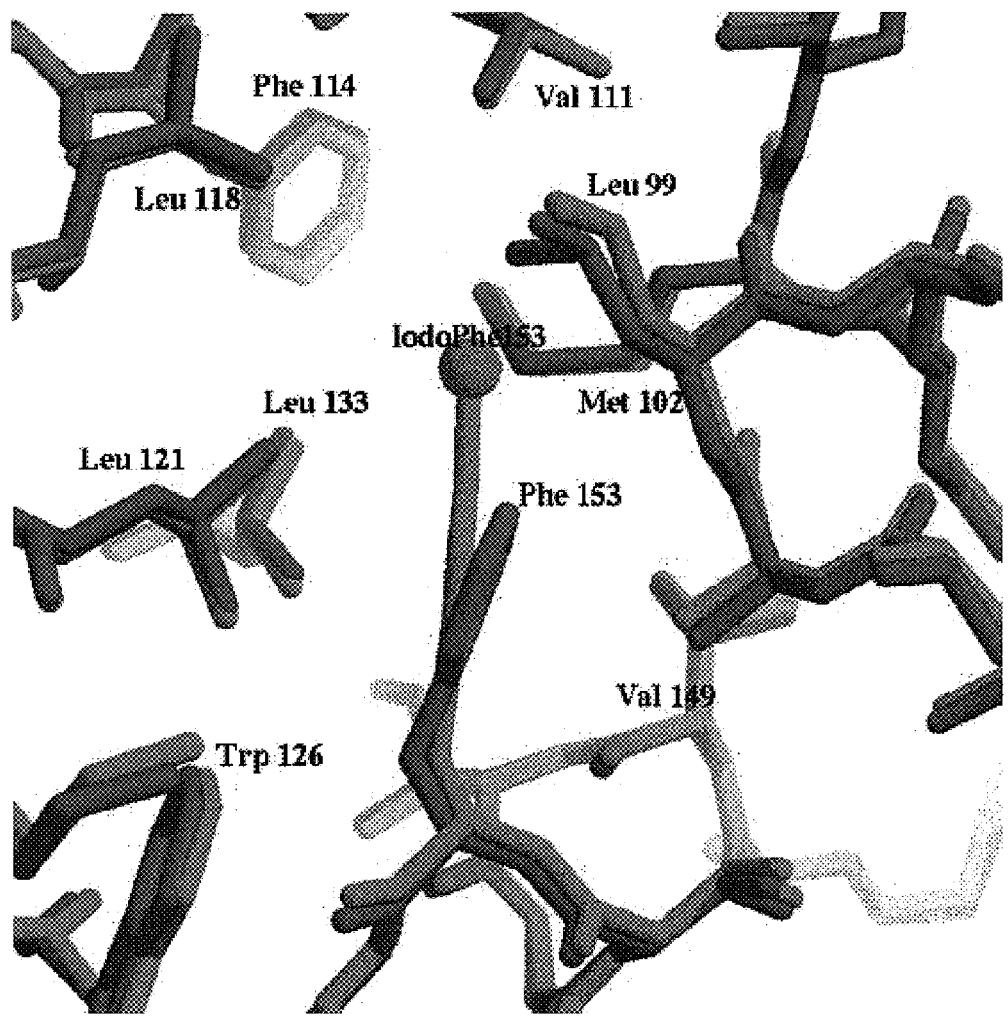

When SOLVE (Terwilliger and Berendzen (1999) "Automated MAD and MIR structure solution" Acta Crystallogr D 55 (Pt 4):849-861) was used to determine the iodine position and calculate the initial phases, only data sets with a mean redundancy greater than 6.8 (135° of data) provided suitable starting phases (FIG. 3 Panel B). This redundancy, corresponding to a $<\Delta F>/<\sigma\Delta F>$ of 2.6, is probably close to the absolute minimum signal necessary for substructure determination and phase derivation, and for this spacegroup ($P3_221$) represents just over two times the amount of data one would collect for a complete native data set (60°) or the amount of data needed for an inverse beam experiment. Additional redundancy, and thus anomalous signal, does allow faster convergence and the placement of more residues with the auto-building algorithm of RESOLVE (Terwilliger (2001) "Maximum-likelihood density modification using pattern recognition of structural motifs" Acta Crystallogr D 57:1755-1762) primarily because of the generation of better starting phases (Table 1).

The structure of the iodinated T4 lysozyme conforms to the canonical viral lysozyme structure (FIG. 3 Panels A and B; Nicholson et al. (1991) Biochemistry 30:9816-9828 and Weaver and Matthews (1987) "Structure of bacteriophage T4 lysozyme refined at 1.7 A resolution" J Mol Biol 193:189-199), a bi-lobal mixed α/β fold. Lobe 1 of the structure is entirely α-helical, whilst lobe 2 consists of an anti-parallel β-sheet inserted between 3 α-helices. The only difference between the native and modified structure is the incorporation of the iodoPhe residue at position 153 in the center of lobe 1 (FIG. 3 Panel A). As would be expected for a residue within the hydrophobic core, the iodoPhe is completely buried and makes no contact with the outside solvent (calculated with Tunneller). The iodoPhe residue is only slightly distorted relative to the native Phe 153, the chi1 angle being rotated by 23° relative to the native structure, presumably to accommodate the large iodine atom (FIG. 3 Panel C). All other residues in the protein are largely unchanged relative to the native structure. The 264 common atoms in a 10 Å sphere around the iodine atom have a root mean squared deviation (rmsd) of 1.08 Å, whilst the 164 aligned Cα atoms in the structures have an rmsd of 0.282 Å. This together with the isomorphous nature of the crystals shows that the incorporation of the iodine does not perturb the structure to any degree (FIG. 3 Panel C).

In summary, these examples describe a novel approach to preparing iodine-containing proteins for SAD phasing. It overcomes the limitations of current methods by introducing an iodine atom into proteins site-specifically and quantitatively. With T4 lysozyme, a protein of 164 amino acid residues, a single iodoPhe substitution was enough to carry out SAD phasing and solve the structure with an in-house X-ray source. Moreover, the iodine atom did not perturb the protein structure. Considerably less data was required than for the corresponding experiment using sulfur as the anomalous scatterer. Because this approach can also be used to introduce two or more iodoPhe into proteins in response to amber codons, its application to SAD phasing is not limited by the protein size. The technique will also be useful for proteins that contain few or no methionine residues where the SeMet (selenomethionine) derivatization method is not applicable. And finally, this method is also applicable to higher organisms. Indeed, Sakamoto et al. (2002) "Site-specific incorporation of an unnatural amino acid into proteins in mammalian cells" Nucleic Acids Res 30:4692-4699 and Chin et al. (2003) "An expanded eukaryotic genetic code" Science 301:964-967 have shown that 3-iodo-L-tyrosine and p-iodo-L-phenylalanine can be incorporated into proteins in response to an amber codon in mammalian cells and in yeast.

Although the model protein incorporates iodoPhe using an orthogonal tRNA system, it is not intended that the invention be limited to the use of iodoPhe. The compositions and methods for protein crystal structure determination, a taught herein, can use a variety of heavy atoms incorporated into the unnatural amino acid. Any heavy atom suitable for this purpose, as known on the art, can be incorporated into an unnatural amino acid. Furthermore, the unnatural amino acid used in these compositions and methods is not limited to phenylalanine-based structures for the in vivo synthesis of proteins comprising heavy atoms.

Expression and Purification of IodoPhe Substituted T4 Lysozyme

Plasmid pT4L153TAG was used to express an Phe153→TAG mutant cysteine-free T4 lysozyme under the control of a bacteriophage T5 promoter and $t_0$ terminator, and the tRNA$_{CUA}^{Tyr}$ gene under the control of the lpp promoter and rrnC terminator. Plasmid pBK-iodoPheRS encoded the iodoPhe specific tRNA-aminoacyl synthetase under the control of the constitutive *E. coli* GlnRS promoter and terminator. Electro-competent BL21 (DE3) cells cotransformed with pT4L153TAG and pBK-IodoPheRS were grown in minimal medium containing 1% glycerol and 0.3 mM leucine (GMML medium) with 50 µg/ml kanamycin, 34 µg/ml of chloramphenicol, and 1.0 mM p-iodo-L-phenylalanine at 37° C. When cells reached an $OD_{600}$ of 0.5, isopropyl-β-D-thiogalactopyranoside was added to a final concentration of 1 mM to induce protein expression. Cells were grown an additional 8 hours at 30° C., pelleted, and resuspended in 28 mL lysis buffer [30 mM Tris.HCl, pH 7.6, 1 tablet of Complete (protease inhibitor cocktail tablets, Roche Applied Science) for 50 mL solution]. The cells were lysed by sonication and pelleted again. The supernatant was then applied to a cation exchange column (Mono S HR 10/10 column, Amersham Biosciences) previously equilibrated with 30 mM Tris.HCl, pH 7.6. The proteins were eluted with a linear gradient from 0 to 0.28 M NaCl. Peak fractions were analysed by SDS-PAGE. Fractions from a major peak that eluted at 0.25 M NaCl were pooled together and applied to a gel filtration column (Superdex 75 HR 10/30 column, Amersham Biosciences). Proteins were eluted with 25 mM Tris.HCl, 100 mM NaCl, pH 7.6. The final purified T4 lysozyme was dialysed against 100 mM NaH$_2$PO$_4$, 0.55 M NaCl, pH 6.7 and then concentrated to 25 mg/ml for crystallization. The concentration of protein was measured by Bradford assay (BCA kit, Biorad).

Crystallization of iodoPhe Substituted T4 Lysozyme

Mutant T4 lysozyme was crystallized using the hanging-drop vapor diffusion method under conditions similar to those described for other T4 lysozyme mutants (Eriksson et al. (1993) J Mol Biol 229:747-769). The crystallization solution consisted of 2.0-2.2 M aqueous sodium/potassium phosphate buffer (pH 6.7-7.1), with 15 mM hydroxyethyl disulfide. One microliter of a 25 mg/ml protein solution was mixed with 1 µl of crystallization solution on a silanized coverslip which was inverted and placed above a reservoir containing 0.5 ml of the crystallization solution. Crystals grew in two weeks at 4° C. Prior to data collection, crystals were soaked in a cryoprotectant solution (2.3 M sodium/potassium phosphate buffer, 0.25 M NaCl, 25% glycerol) and cryo-cooled to 100°K.

Data Collection

Data was collected at 100°K on a standard in-house Rotating RU300 X-ray generator (Rigaku/MSC) incorporating Osmic mirrors and an RAXISIV++ imaging plate system at the CuKα wavelength of 1.5418 Å. The crystal was mounted in a random orientation, no attempt being made to collect Bijvoet pairs on the same image, and data was collected in 0.5 degree oscillations for a total rotation of 360° using an exposure time of 5 minutes per frame. Data were collected to a maximum resolution of 2.0 Å and reduced and scaled with the HKL2000 package (Otwinowski and Minor (1997) "Processing of X-ray Diffraction Data Collected in Oscillation Mode" Methods in Enzymology 276:307-326). Crystals belong to the trigonal space group P3$_2$21 and are isomorphous with standard T4 lysozyme crystals (Nicholson et al. (1991) Biochemistry 30:9816-9828) (Table1). To determine the minimum data needed to determine the substructure and derive initial phases, the data were split into 6 different sets constituting rotations of 360, 180, 145, 90, 60 and 45°, statistics for which are presented in Table1. Optimum completeness for the data sets was calculated using the strategy option of Mosflm (Collaborative Computational Project (1994) "The CCP4 suite: programs for protein crystallography" Acta Crystallogr D 50:760-763). Further crystallographic manipulations were performed with the CCP4 package (Collaborative Computational Project (1994) Acta Crystallogr D 50:760-763).

Structure Solution and Refinement

All substructure solution and determination of initial phases were carried out with SOLVE (Terwilliger and Berendzen (1999) Acta Crystallogr D 55 (Pt 4):849-861) using the standard SAD phasing script and local scaling of the data. This was followed by solvent flattening and auto-building using RESOLVE (Terwilliger and Berendzen (1999) Acta Crystallogr D 55 (Pt 4):849-861) with a solvent content of 50%. For the three datasets (45, 60, 90°) that SOLVE was unable to determine the iodine position, SHELXS and SHELXD (Schneider and Sheldrick (2002) "Substructure solution with SHELXD" Acta Crystallogr D Biol Crystallogr 58:1772-1779) were also tried with no success. Refinement and rebuilding of the model was carried out with all data between 30.0 and 2.0 Å, using Refmac5 (Murshudov et al. (1997) "Refinement of Macromolecular Structures by the Maximum-Likelihood Method" Acta Crystallogr D 53:240-255), incorporating a parameter file for the p-iodo-L-phenylalanine generated by PROGRG (van Aalten et al. (1996) "PRODRG, a program for generating molecular topologies and unique molecular descriptors from coordinates of small molecules" J Comput Aided Mol Des 10:255-262), and O (Jones et al. (1991) "Improved methods for building protein models in electron density maps and the location of errors in these models" Acta Crystallogr A 47 (Pt 2):110-119). Automatic water building was carried with the ARP/WARP package (Lamzin and Wilson (1993) "Automated refinement of protein models" Acta Crystallogr D 49:129-147). Subsequently, 3 water molecules were replaced by 3 putative Cl ions, added on the basis of inspection of the anomalous difference Patterson maps and the low B-factors of the waters. In addition a 2-hydroxyethyl disulfide moiety was also added as observed in the anomalous difference Fouriers and in most other T4 lysozyme structures. The final model converged at an R$_{cryst}$ and R$_{free}$ of 0.157 and 0.207, respectively, the stereochemical properties were excellent and all residues were contained within allowed regions of the Ramachandran plot (Table 1).

The structure has been deposited with the PDB and can be accessed as PDB code 1T6H.

While the foregoing invention has been described in some detail for purposes of clarity and understanding, it will be clear to one skilled in the art from a reading of this disclosure that various changes in form and detail can be made without departing from the true scope of the invention. For example, all the techniques and compositions described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

TABLE 1

SUMMARY OF DATA COLLECTION STATISTICS AND MODEL AUTOBUILDING

| Unit Cell | a = 59.67 Å, b = 59.67 Å, c = 97.57 Å, α = 90.0°, β = 90.0°, γ = 120° | | | | | |
|---|---|---|---|---|---|---|
| Space Group | P3$_2$21 | | | | | |
| Resolution (Å) | 30.0-2.0 | | | | | |
| Degrees collected (°) | 45 | 60 | 90 | 135 | 180 | 360 |
| R$_{merge}$ | 0.051 | 0.055 | 0.054 | 0.059 | 0.060 | 0.078 |
| Completeness | 0.93 | 0.97 | 0.99 | 0.98 | 0.99 | 0.99 |
| Anomalous completeness | 0.66 | 0.80 | 0.82 | 0.83 | 0.86 | 0.86 |
| Mean redundancy | 2.4 | 3.2 | 4.4 | 6.8 | 9.0 | 19.4 |
| Determined substructure | No | No | No | Yes | Yes | Yes |
| Mean FOM | — | — | — | 0.36 | 0.37 | 0.39 |
| Mean ΔF | 0.034 | 0.031 | 0.026 | 0.037 | 0.033 | 0.024 |
| Mean ΔF/σΔF | 1.45 | 1.48 | 1.50 | 2.64 | 2.77 | 6.25 |

TABLE 1-continued

SUMMARY OF DATA COLLECTION STATISTICS
AND MODEL AUTOBUILDING

| | | | | | | |
|---|---|---|---|---|---|---|
| Number of cycles autobuilding needed | — | — | — | 18 | 17 | 7 |
| No. residues built (percentage, %) | — | — | — | 138 (84) | 139 (85) | 151(92) |
| No. side chains placed (percentage, %) | — | — | — | 122(74) | 120(73) | 133(81) |
| Structure Refinement | | | | | | |
| $R_{cryst}$ ($R_{free}$) | 0.157(0.207) | | | | | |
| rmsd bonds (Å) | 0.012 | | | | | |
| rmsd angles (°) | 1.258 | | | | | |
| Mean B-factor (Å$^2$) | 17.18 | | | | | |
| No. protein atoms | 1322 | | | | | |
| No. waters | 187 | | | | | |
| No. heteroatoms | 20 | | | | | |

$R_{merge} = \Sigma |I_i - \langle I_i \rangle| / \Sigma |I_i|$ where $I_i$ is the scaled intensity of the ith measurement, and $\langle I_i \rangle$ is the mean intensity for that reflection.
$R_{cryst} = \Sigma | |F_{obs}| - |F_{calc}| | / \Sigma |F_{obs}|$ where $F_{calc}$ and $F_{obs}$ are the calculated and observed structure factor amplitudes, respectively.
$R_{free}$ = as for $R_{cryst}$, but for 4.6% of the total reflections chosen at random and omitted from refinement.

What is claimed is:

1. A translation system comprising:
   a) an orthogonal aminoacyl-tRNA synthetase comprising the amino acid sequence of SEQ ID NO:3 or SEQ ID NO:4;
   b) an orthogonal aminoacyl-tRNA synthetase comprising an amino acid sequence encoded by the polynucleotide sequence of SEQ ID NO:1 or the polynucleotide sequence of SEQ ID NO:2; or
   c) an orthogonal aminoacyl-tRNA synthetase comprising an amino acid sequence that is derived from and at least 95% identical to that of SEQ ID NO:10 and that comprises four or more amino acids selected from the group consisting of:
      i) leucine at a position corresponding to Tyr32 of SEQ ID NO:10;
      ii) serine or glutamate at a position corresponding to Glu107 of SEQ ID NO:10;
      iii) proline at a position corresponding to Asp158 of SEQ ID NO:10;
      iv) leucine or arginine at a position corresponding to Ile159 of SEQ ID NO:10; and
      v) glutamate or arginine at a position corresponding to Leu162 of SEQ ID NO:10,
   which synthetase preferentially aminoacylates an orthogonal tRNA with a brominated or iodinated amino acid wherein said brominated or iodinated amino acid is a brominated or an iodinated phenylalanine or tyrosine.

2. The translation system of claim 1, wherein the translation system comprises an isolated host cell.

3. The translation system of claim 2, wherein the cell is an *E. coli* cell.

4. The translation system of claim 2, wherein the orthogonal aminoacyl-tRNA synthetase is encoded by one or more nucleic acids in the cell.

5. The translation system of claim 1, wherein the translation system comprises an in vitro translation system.

6. The translation system of claim 1, wherein the orthogonal aminoacyl-tRNA synthetase of c) comprises five amino acids selected from the group consisting of:
   i) leucine at a position corresponding to Tyr32 of SEQ ID NO:10;
   ii) seine or glutamate at a position corresponding to Glu107 of SEQ ID NO:10;
   iii) proline at a position corresponding to Asp158 of SEQ ID NO:10;
   iv) leucine or arginine at a position corresponding to Ile159 of SEQ ID NO:10; and
   v) glutamate or arginine at a position corresponding to Leu162 of SEQ ID NO:10.

7. The translation system of claim 1, wherein the brominated or iodinated amino acid of c) is L-4-bromophenylalanine or L-4-iodophenylalanine.

8. The translation system of claim 1, wherein the brominated or iodinated amino acid of c) is L-2-iodophenylalanine, L-3-iodophenylalanine, L-2-iodotyrosine, L-3-iodotyrosine, L-2-bromophenylalanine, L-3-bromophenylalanine, L-2-bromotyrosine, or L-3-bromotyrosine.

9. The translation system of claim 1, comprising an orthogonal tRNA.

10. The translation system of claim 9, wherein the orthogonal tRNA comprises or is encoded by the polynucleotide sequence of SEQ ID NO:5.

11. The translation system of claim 9, wherein the orthogonal tRNA recognizes a selector codon that is a stop codon.

12. The translation system of claim 9, comprising a target nucleic acid that comprises a selector codon recognized by the orthogonal tRNA, which orthogonal tRNA is preferentially charged with a brominated or iodinated amino acid by the orthogonal aminoacyl-tRNA synthetase.

13. The translation system of claim 12, comprising a protein encoded by the target nucleic acid, which protein comprises the brominated or iodinated amino acid.

14. A composition comprising: an orthogonal aminoacyl-tRNA synthetase comprising the amino acid sequence of SEQ ID NO:3 or SEQ ID NO:4 or a conservative variant thereof, which conservative variant comprises conservative amino acid substitutions at less than 5% of the amino acids in SEQ ID NO:3 or SEQ ID NO:4, and which conservative variant comprises five amino acids selected from the group consisting of:
   i) leucine at a position corresponding to Tyr32 of SEQ ID NO: 10;
   ii) seine or glutamate at a position corresponding to Glu107 of SEQ ID NO:10;
   iii) proline at a position corresponding to Asp158 of SEQ ID NO:10;
   iv) leucine or arginine at a position corresponding to Ile159 of SEQ ID NO:10; and
   v) glutamate or arginine at a position corresponding to Leu162 of SEQ ID NO:10 ;
   which synthetase preferentially aminoacylates an orthogonal tRNA with a brominated or iodinated amino acid wherein said brominated or iodinated amino acid is a brominated or iodinated phenylalanine or tyrosine.

15. The composition of claim 14, comprising the orthogonal tRNA, wherein the orthogonal aminoacyl-tRNA synthetase preferentially aminoacylates the orthogonal tRNA with the brominated or iodinated amino acid.

16. The composition of claim 15, wherein the orthogonal tRNA comprises or is encoded by the polynucleotide sequence of SEQ ID NO:5.

17. The composition of claim 14, comprising an isolated host cell, wherein the orthogonal aminoacyl-tRNA synthetase is encoded by one or more nucleic acids in the cell.

18. The composition of claim 17, wherein the cell is an *E. coli* cell.

19. The composition of claim 14, comprising a translation system, which translation system comprises an isolated host cell or an in vitro translation system.

20. The composition of claim 14, comprising an isolated host cell, wherein the orthogonal aminoacyl-tRNA synthetase is encoded by one or more nucleic acids in the cell, the cell further comprising:
   the orthogonal tRNA; and
   the brominated or iodinated amino acid;
   wherein the orthogonal tRNA recognizes a selector codon, and the orthogonal aminoacyl-tRNA synthetase preferentially aminoacylates the orthogonal tRNA with the brominated or iodinated amino acid.

21. The composition of claim 20, wherein the cell comprises a target nucleic acid that encodes a protein of interest, wherein the target nucleic acid comprises the selector codon that is recognized by the orthogonal tRNA.

22. The composition of claim 21, wherein the cell comprises the protein encoded by the target nucleic acid, which protein comprises the brominated or iodinated amino acid.

23. A nucleic acid comprising:
   a) a polynucleotide sequence that encodes the amino acid sequence of SEQ ID NO:3 or SEQ ID NO:4 or a conservative variant thereof, which conservative variant comprises conservative amino acid substitutions at less than 5% of the amino acids in SEQ ID NO:3 or SEQ ID NO:4, and which conservative variant comprises five amino acids selected from the group consisting of:
   i) leucine at a position corresponding to Tyr32 of SEQ ID NO:10;
   ii) seine or glutamate at a position corresponding to Glu107 of SEQ ID NO:10;
   iii) proline at a position corresponding to Asp158 of SEQ ID NO:10;
   iv) leucine or arginine at a position corresponding to Ile159 of SEQ ID NO:10; and
   v) glutamate or arginine at a position corresponding to Leu162 of SEQ ID NO:10;
   wherein said nucleic acid encodes an aminoacyl-tRNA synthetase that preferentially aminoacylates an orthogonal tRNA with a brominated or iodinated amino acid wherein said brominated or iodinated amino acid is a brominated or iodinated phenylalanine or tyrosine; or
   b) the polynucleotide sequence of SEQ ID NO:1 or SEQ ID NO:2 or a fully complementary polynucleotide sequence thereof.

24. A vector comprising or encoding a nucleic acid of claim 23.

25. The vector of claim 24, wherein the vector is an expression vector.

26. A kit for producing a protein with a brominated or iodinated amino acid at a specified position, wherein said brominated or iodinated amino acid is a brominated or iodinated phenylalanine or tyrosine, the kit comprising:
an isolated host cell comprising:
a) an orthogonal tRNA that functions in the cell and recognizes a selector codon; and
b) an orthogonal aminoacyl-tRNA synthetase comprising an amino acid sequence that is derived from and at least 95% identical to that of SEQ ID NO:10 and that comprises four or more amino acids selected from the group consisting of:
i) leucine at a position corresponding to Tyr32 of SEQ ID NO:10;
ii) serine or glutamate at a position corresponding to Glu107 of SEQ ID NO:10;
iii) proline at a position corresponding to Asp158 of SEQ ID NO:10;
iv) leucine or arginine at a position corresponding to Ile159 of SEQ ID NO:10; and
v) glutamate or arginine at a position corresponding to Leu162 of SEQ ID NO:10,
which synthetase preferentially aminoacylates the orthogonal tRNA with the brominated or iodinated phenylalanine or tyrosine; and
the brominated or iodinated phenylalanine or tyrosine;
packaged in one or more container.

27. A method of producing a protein in a cell with a brominated or iodinated amino acid at a specified position wherein said brominated or an iodinated amino acid is a brominated or an iodinated phenylalanine or tyrosine, the method comprising:
providing an isolated host cell comprising:
a) a nucleic acid that comprises at least one selector codon and that encodes the protein;
b) an orthogonal tRNA that functions in the cell and recognizes the selector codon; and
c) an orthogonal aminoacyl-tRNA synthetase comprising an amino acid sequence that is derived from and at least 95% identical to that of SEQ ID NO:10 and that comprises four or more amino acids selected from the group consisting of:
i) leucine at a position corresponding to Tyr32 of SEQ ID NO:10;
ii) serine or glutamate at a position corresponding to Glu107 of SEQ ID NO:10;
iii) proline at a position corresponding to Asp158 of SEQ ID NO:10;
iv) leucine or arginine at a position corresponding to Ile159 of SEQ ID NO:10; and
v) glutamate or arginine at a position corresponding to Leu162 of SEQ ID NO:10,
which synthetase preferentially aminoacylates the orthogonal tRNA with the brominated or iodinated phenylalanine or tyrosine;
growing the cell in an appropriate medium;
providing the brominated or iodinated phenylalanine or tyrosine; and
incorporating the brominated or iodinated amino acid into the specified position in the protein during translation of the nucleic acid with the at least one selector codon, thereby producing the protein.

28. The method of claim 27, wherein the orthogonal aminoacyl-tRNA synthetase comprises an amino acid sequence which comprises any one of SEQ ID NOs:3-4.

29. The method of claim 27, wherein the orthogonal tRNA comprises or is encoded by a polynucleotide sequence as set forth in SEQ ID NO:5.

30. The method of claim 27, wherein the cell is a non-eukaryotic cell.

31. The method of claim 30, wherein the non-eukaryotic cell is an *E. coli* cell.

32. The method of claim 27, wherein the brominated or iodinated amino acid is L-4-bromophenylalanine or L-4-iodophenylalanine.

33. A method of providing a protein with a heavy atom-containing amino acid at a specified position, wherein said heavy atom-containing amino acid is a brominated or an iodinated phenylalanine or tyrosine for use in protein crystallographic studies, the method comprising:
expressing the protein in a translation system comprising:
an orthogonal tRNA;
the brominated or iodinated phenylalanine or tyrosine, and
an orthogonal aminoacyl-tRNA synthetase which preferentially aminoacylates the orthogonal tRNA with the brominated or iodinated phenylalanine or tyrosine, which orthogonal aminoacyl-tRNA synthetase comprises the amino acid sequence of SEQ ID NO:3 or SEQ ID NO:4 or a conservative variant thereof, which conservative variant comprises conservative amino acid substitutions at less than 5% of the amino acids in SEQ ID NO:3 or SEQ ID NO:4, and which conservative variant comprises five amino acids selected from the group consisting of:
i) leucine at a position corresponding to Tyr32 of SEQ ID NO:10;
ii) serine or glutamate at a position corresponding to Glu107 of SEQ ID NO:10;
iii) proline at a position corresponding to Asp 158 of SEQ ID NO:10;
iv) leucine or arginine at a position corresponding to Ile159 of SEQ ID NO:10; and
v) glutamate or arginine at a position corresponding to Leu162 of SEQ ID NO:10;
thereby producing a heavy-atom containing protein.

34. The method of claim 33, wherein the brominated or iodinated amino acid is L-4-bromophenylalanine or L-4-iodophenylalanine.

35. The translation system of claim 1, wherein the orthogonal aminoacyl-tRNA synthetase of c) comprises an amino acid sequence that is derived from and at least 98% identical to that of SEQ ID NO:10.

* * * * *